(12) United States Patent
Hausner et al.

(10) Patent No.: US 11,485,758 B2
(45) Date of Patent: Nov. 1, 2022

(54) BI-TERMINAL PEGYLATED INTEGRIN-BINDING PEPTIDES AND METHODS OF USE THEREOF

(71) Applicant: The Regents of the University of California, Oakland, CA (US)

(72) Inventors: Sven H. Hausner, Sacramento, CA (US); Julie L. Sutcliffe, Sebastopol, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 17/131,324

(22) Filed: Dec. 22, 2020

(65) Prior Publication Data

US 2021/0206804 A1 Jul. 8, 2021

Related U.S. Application Data

(63) Continuation of application No. 15/292,564, filed on Oct. 13, 2016, now Pat. No. 10,919,932, which is a continuation of application No. PCT/US2015/025700, filed on Apr. 14, 2015.

(60) Provisional application No. 61/979,997, filed on Apr. 15, 2014.

(51) Int. Cl.
| | |
|---|---|
| *C07K 7/06* | (2006.01) |
| *A61K 38/00* | (2006.01) |
| *A61K 47/60* | (2017.01) |
| *A61K 47/64* | (2017.01) |
| *A61K 51/08* | (2006.01) |
| *C07K 14/705* | (2006.01) |
| *A61K 31/337* | (2006.01) |

(52) U.S. Cl.
CPC ............. *C07K 7/06* (2013.01); *A61K 31/337* (2013.01); *A61K 38/00* (2013.01); *A61K 47/60* (2017.08); *A61K 47/64* (2017.08); *A61K 51/082* (2013.01); *C07K 14/70546* (2013.01); *C12N 2770/32122* (2013.01)

(58) Field of Classification Search
CPC ...... A61K 31/00; A61K 31/337; A61K 38/00; A61K 47/60; A61K 47/64; A61K 51/00; A61K 51/08; A61K 51/082; A61K 2121/00; A61K 2123/00; C07K 14/70546; C07K 7/06; C07K 14/705; C12N 2770/32111
USPC .......... 424/1.11, 1.49, 1.65, 1.69, 1.81, 1.85, 424/1.89, 9.1, 9.2; 514/1, 1.1, 19.2, 19.3, 514/19.4, 19.5, 19.6, 21.6, 21.7; 530/300, 530/328
See application file for complete search history.

(56) References Cited

U.S. PATENT DOCUMENTS

| | | | |
|---|---|---|---|
| 6,110,466 A | 8/2000 | Lomonossoff et al. | |
| 8,906,844 B2 | 12/2014 | Mezo et al. | |
| 10,919,932 B2* | 2/2021 | Hausner | A61K 38/00 |
| 11,185,601 B2* | 11/2021 | Tang | A61K 47/62 |
| 2013/0315996 A1 | 11/2013 | Steinberg et al. | |

FOREIGN PATENT DOCUMENTS

| | | |
|---|---|---|
| JP | 2009509562 A | 3/2009 |
| JP | 2013544248 A | 12/2013 |
| WO | 2002/087497 A2 | 11/2002 |
| WO | 2007/039728 A2 | 4/2007 |
| WO | 2012/065751 A1 | 5/2012 |
| WO | 2012/126441 A2 | 9/2012 |
| WO | 2012/126441 A3 | 11/2012 |
| WO | 2015/160770 A1 | 10/2015 |

OTHER PUBLICATIONS

Extended European Search Report dated Oct. 6, 2017 for EP Application No. 15779171.6, 12 pages.
"Labeling, Derivatization and Crosslinking Reagents for Biological and Related Materials with dPEG™", Quanta Biodesign, Nov. 5, 2004, 38 pages.
"PolyPure, Products; PEG amines; PEG acids and amino acids; PEG thiols and disulfides", BIOTINS, Apr. 2004, 5 pages.
Acharaya , "The 3-Dimensional Structure of Foot-and-Mouth-Disease Virus at 2.9—A Resolution", Nature, vol. 337, 1989, pp. 709-716.
Alavi et al., "Implications of PET based molecular imaging on the current and future practice of medicine ", Seminars in Nuclear Medicine, vol. 34, 2004, pp. 56-69.

(Continued)

*Primary Examiner* — D. L. Jones

(74) *Attorney, Agent, or Firm* — Kilpatrick Townsend & Stockton LLP

(57) ABSTRACT

The present invention provides bi-terminal PEGylated peptide conjugates that target an integrin such as $\alpha_v\beta_6$ integrin. In particular embodiments, the peptide conjugates of the present invention further comprise a biological agent such as an imaging agent or a therapeutic agent, e.g., covalently attached to one of the PEG moieties. The peptide conjugates of the present invention are particularly useful for imaging a tumor, organ, or tissue and for treating integrin-mediated diseases and disorders such as cancer, inflammatory diseases, autoimmune diseases, chronic fibrosis, chronic obstructive pulmonary disease (COPD), lung emphysema, and chronic wounding skin disease. Compositions and kits containing the peptide conjugates of the present invention find utility in a wide range of applications including, e.g., in vivo imaging and immunotherapy.

30 Claims, 30 Drawing Sheets

Specification includes a Sequence Listing.

(56) References Cited

OTHER PUBLICATIONS

Bates, "Transcriptional Activation of Integrin B6 During the Epithelial-Mesenchymal Transition Defines a Novel Prognostic Indicator of Aggressive Colon Carcinoma", The Journal of Clinical Investigation, vol. 115, 2005, pp. 339-347.
Beer et al., "Biodistribution and Pharmacokinetics of the avb3-Selective Tracer $^{18}$F-Galacto-RGD in Cancer Patients", The Journal of Nuclear Medicine, vol. 46, No. 8, 2005, pp. 1333-1341.
Blodgett et al., "Townsend DW. PET/CT: Form and Function", Radiology, vol. 242, 2007, pp. 360-385.
Burman et al., "Specificity of the VP1 GH Loop of Foot-and-Mouth Disease Virus For Alpha v Integrins", Journal of Virology, vol. 80, 2006, pp. 9798-9810.
Busk et al., "Characterization of the Integrin-Aipha-V-Beta-6 as a Fibronectin-Binding Protein", Journal of Biological Chemistry, vol. 267, 1992, pp. 5790-5796.
Campbell et al., "Integrin Structure, Activation, and Interactions", Cold Spring Harbor Perspectives in Biology, vol. 3, No. 3, Jan. 19, 2011, a004994, 15 pages.
Chen et al., "Long-Term Survival After Pancreatic Cancer Treatment", American Journal of Surgery, vol. 194, 2007, pp. S127-S130.
Chen et al., "MicroPET Imaging of Brain Tumor Angiogenesis With $^{18}$F-labeled PEGylated RGD Peptide", European Journal of Nuclear Medicine and Molecular Imaging, vol. 31, No. 8, 2004, pp. 1081-1089.
Chen et al., "Pegylated Arg-Giy-Asp Peptide: $^{64}$Cu Labeling and PET Imaging of Brain Tumor $A_v\beta_3$-Integrin Expression", The Journal of Nuclear medicine and Biology, vol. 45, No. 10, 2004, pp. 1776-1783.
Chen et al., "Pharmacokinetics and Tumor Retention of $^{125}$I-Labeled RGD Peptide Are Improved by PEGylation", Nuclear Medicine and Biology, vol. 31, 2004, pp. 11-19.
Currier et al., "Targeted Drug Delivery with an Integrin-Binding Knottin-Fc-MMAF Conjugate Produced by Cell-Free Protein Synthesis", Molecular Cancer Therapeutics, vol. 15, No. 6, 2016, pp. 1291-1300.
Czernin et al., "Improvements in Cancer Staging With PET/CT: Literature-Based Evidence", J Nucl Med, vol. 48, 2007, pp. 78S-88S.
Defrise et al., "Exact and Approximate Rebinning Algorithms for 3-D PET Data.", IEEE T Med Imaging, vol. 16, No. 2, Apr. 1997, pp. 145-158.
Delbeke et al., "Pancreatic Tumors: Role of Imaging in the Diagnosis, Staging, and Treatment", Journal of Hepato-Biliary-Pancreatic Surgery, vol. 11, 2004, pp. 4-10.
Dijkgraaf et al., "Effects of Linker Variation on the In Vitro and In Vivo Characteristics of an $^{111}$In-labeled RGD Peptide", Nuclear Medicine and Biology, vol. 34, Jan. 2007, pp. 29-35.
Duncan et al., "The Dawning Era of Polymer Therapeutics", Nat Rev Drug Discov, vol. 2, May 2003, pp. 347-360.
Elayadi et al., "A Peptide Selected by Biopanning Identifies the Integrin avb6 as a Prognostic Biomarker For Nonsmall Cell Lung Cancer", Cancer Res, vol. 67, 2007, pp. 5889-5895.
Ghannad et al., "Absence of avb6 Integrin Is Linked to Initiation and Progression of Periodontal Disease", American Journal of Pathology, vol. 172, No. 5, 2008, pp. 1271-1286.
Greenwald et al., "Effective Drug Delivery by PEGylated Drug Conjugates", Adv Drug Deliver Rev, vol. 55, 2003, pp. 217-250.
Hamley, "PEG-Peptide Conjugates", Biomacromolecules, vol. 15, No. 5, 2014, pp. 1543-1559.
Hancock et al., "New Micro-Testfor Detection of Incomplete Coupling Reactions in Solid-Phase Peptide-Synthesis Using 2,4,6-Trinitrobenzene-Sulphonic Acid", Anal Biochem, vol. 71, 1976, pp. 260-264.
Harris et al., "Effect of Pegylation on Pharmaceuticals. Nature Reviews Drug Discovery", Nature Reviews Drug Discovery, vol. 2, 2003, pp. 214-221.

Hausner et al., "Targeted in Vivo Imaging of Integrin $\alpha_v\beta_6$ with an Improved Radiotracer and its Relevance in a Pancreatic Tumor Model", Cancer Research, vol. 69, No. 14, Jul. 15, 2009, pp. 5843-5850.
Hausner et al., "The Effect of Bi-Terminal Pegylation of an Integrin $\alpha_v\beta_6$-Targeted 18F Peptide on Pharmacokinetics and Tumor Uptake", The Journal of Nuclear Medicine, vol. 56, No. 5, May 2015, pp. 784-790.
Hausner et al., "Use of a peptide derived from foot-and-mouth-disease-virus (FMDV) for the non-invasive imaging of human cancer: Generation and evaluation of 4-[$^{18}$F]FBA-A20FMDV2 for in vivo imaging of integrin $\alpha_v\beta_6$ expression with Positron Emission Tomography", Cancer Research, vol. 67, No. 16, Aug. 15, 2007, pp. 7833-7840.
Hazelbag et al., "Overexpression of the $A_v\beta_6$ Integrin in Cervical Squamous Cell Carcinoma Is a Prognostic Factor for Decreased Survival", Journal of Pathology, vol. 212, 2007, pp. 316-324.
Heinrich et al., "Positron Emission Tomography/Computed Tomography Influences on the Management of Resectable Pancreatic Cancer and Its Cost-Effectiveness", Annals of Surgery, vol. 242, Aug. 2005, pp. 235-243.
Hinds et al., "Effects of PEG Conjugation on Insulin Properties", Advanced Drug Delivery Reviews, vol. 54, 2002, pp. 505-530.
Jackson et al., "Structure and Receptor Binding", Virus Research, vol. 91, 2003, pp. 33-46.
Jackson et al., "The Epithelial Integrin Alpha V Beta 6 Is a Receptor for Foot-and-Mouth Disease Virus", Journal of Virology, vol. 74, 2000, pp. 4949-4956.
Keogan et al., "Diagnosis of Pancreatic Carcinoma: Role of FDG PET", American Journal of Roentgenology, vol. 171, 1998, pp. 1565-1570.
King et al., "Facile Formation of Dynamic Hydrogel Microspheres for Triggered Growth Factor Delivery", Acta Biomaterialia, vol. 7, No. 3, Mar. 2011, pp. 975-985.
Koopman et al., "Antibody-Mediated Blockade of Integrin $\alpha_v\beta_6$ Inhibits Tumor Progression in Vivo by a Transforming Growth Factor-β-Regulated Mechanism", Cancer Research, American Association for Cancer Research, vol. 68, Issue 2, Jan. 15, 2008, pp. 561-570.
Kraft et al., "Definition of an Unexpected Ligand Recognition Motif for aαvβ6 Integrin", Journal of Biological Chemistry, vol. 274, No. 4, 1999, pp. 1979-1985.
Li et al., "$\alpha_v\beta_6$-Fyn Signaling Promotes Oral Cancer Progression", Journal of Biological Chemistry, vol. 278, 2003, pp. 41646-41653.
Li et al., "Identification of Pancreatic Cancer Stem Cells", Cancer Research, vol. 67, No. 3, 2007, pp. 1030-1037.
Liu, "Radiolabeled Multimeric Cyclic RGD Peptides as Integrin avb3 Targeted Radiotracers for Tumor Imaging", Molecular Pharmaceuticals, vol. 3, No. 5, 2005, pp. 472-487.
Logan et al., "Structure of a Major Immunogenic Site on Foot-and-Mouth-Disease Virus", Nature, vol. 362, 1993, pp. 566-568.
Marik et al., "Solid-Phase Synthesis of 2-[$^{18}$F]Fluoropropionyl Peptides", Bioconjugate Chemistry, vol. 17, 2006, pp. 1017-1021.
Miller et al., "Bioactive Hydrogels made from Step-Growth Derived PEG-Peptide Macromers", Biomaterials, vol. 31, No. 13, May 2010, pp. 3736-3743.
Paira et al., "Fluorescent Amphiphilic PEG-Peptide-PEG Triblock Conjugate Micelles for Cell Imaging", Macromolecular Bioscience, vol. 14, No. 7, 2014, pp. 929-935.
Parsons et al., "Preoperative Evaluation of Pancreatic Cancer", Journal of Hepato-Biliary-Pancreatic Surgery, vol. 15, 2008, pp. 429-435.
Qi et al., "High-Resolution 3D Bayesian Image Reconstruction Using The MicroPET Small-Animal Scanner", Phys Med Bioi, vol. 43, 1998, pp. 1001-1013.
Roberts et al., "Chemistry for Peptide and Protein PEGylation", Advanced Drug Delivery Reviews, vol. 54, 2002, pp. 459-476.
Rose et al., "(18)Fluorodeoxyglucose Positron Emission Tomography in the Management of Patients With Suspected Pancreatic Cancer", Annals of Surgery, vol. 229, 1999, pp. 729-738.
Ruoslathi, "RGD and Other Recognition Sequences for Integrins", Annual Review of Cell and Developmental Biology, vol. 12, 1996, pp. 697-715.

(56) References Cited

OTHER PUBLICATIONS

Schöder et al., "Screening for Cancer With PET and PET/CT: Potential and Limitations", J Nucl Med, vol. 48, 2007, p. 4S-18S.

Sheppard et al., "Complete Amino-Acid-Sequence of a Novel Integrin BetaSubunit (Beta-6) Identified in Epithelial-Cells Using the Polymerase Chain-Reaction", Journal of Biological Chemistry, vol. 265, No. 20, 1990, pp. 11502-11507.

Sipos et al., "Immunohistochemical Screening for Beta(6)-Integrin Subunit Expression in Adenocarcinomas Using a Novel Monoclonal Antibody Reveals Strong Up-Regulation in Pancreatic Ductal Adenocarcinomas In Vivo and In Vitro", Histopathology, vol. 45, 2004, pp. 226-236.

Sutcliffe-Goulden et al., "Rapid Solid Phase Synthesis and Biodistribution of $^{18}$F-labelled Linear Peptides", European Journal of Nuclear Medicine and Molecular Imaging, vol. 29, 2002, pp. 754-759.

Verdaguer et al., "Flexibility of the Major Antigenic Loop of Foot-and-Mouth Disease Virus Bound to a Fab Fragment of a Neutralising Antibody: Structure and Neutralisation", Virology, vol. 255, 1999, pp. 260-268.

Veronese et al., "PEGylation, Successful Approach To Drug Delivery", Drug Discovery Today, vol. 10, No. 21, 2005, pp. 1451-1458.

Webster et al., "PEGylated Proteins: Evaluation of Their Safety in the Absence of Definitive Metabolism Studies", Drug Metabolism and Disposition, Epub, vol. 35, No. 1, 2007, pp. 9-16.

Weinacker et al., "Role of the Integrin $\alpha_v\beta_6$ in Cell Attachment to Fibronectin-Heterologous Expression of Intact and Secreted Forms of the Receptor", J Biol Chem, vol. 269, No. 9, 1994, pp. 6940-6948.

Zasadny et al., "Standardized Uptake Values of Normal-Tissues at PET with 2-[$^{18}$F]-Fluoro-2-Deoxy-D-Glucose-Variations with Body-Weight and a Method for Correction", Radiology, vol. 189, 1993, pp. 847-850.

\* cited by examiner

| Tracer | 5 | | 5R | | Relative % change of Mean (or value) vs. 5 (% ID/g [5] = 100%) (ratio [5] = 100 %) |
|---|---|---|---|---|---|
| Structure | 18FFBA-PEG28-A20FMOV2-PEG28 | | 18FFBA-PEG28-A20FMOV2 K18R-PEG28 | | |
| Model | DX3 pair in female nu/nu mouse | | DX3 pair in female nu/nu mouse | | |
| Time point | 2 hours | | 2 hours | | |
| Organ | Mean | SD | Mean | SD | |
| Urine | 348,758 | 164.277 | 106.913 | 13.124 | -69 |
| Blood | 0.305 | 0.121 | 0.104 | 0.017 | -66 |
| Gall Bladder | 6.637 | 2.647 | 11.480 | 7.200 | 73 |
| Liver | 0.298 | 0.124 | 0.094 | 0.017 | -69 |
| Heart | 0.875 | 0.164 | 0.502 | 0.175 | -43 |
| Lung | 1.737 | 0.963 | 1.831 | 0.327 | 5 |
| Spleen | 0.072 | 0.032 | 0.054 | 0.025 | -25 |
| Kidney | 33.319 | 2.750 | 12.388 | 2.999 | -63 |
| Pancreas | 0.333 | 0.092 | 0.135 | 0.054 | -60 |
| Stomach | 9.222 | 0.396 | 4.576 | 0.439 | -50 |
| Sm Intestine | 2.561 | 0.537 | 1.231 | 0.194 | -52 |
| Bladder | 2.396 | 0.365 | 1.367 | 0.439 | -43 |
| Skin | 1.100 | 0.360 | 0.833 | 0.166 | -24 |
| Muscle | 0.726 | 0.111 | 0.528 | 0.099 | -27 |
| Bone | 0.608 | 0.061 | 0.587 | 0.082 | -4 |
| Tail | 0.565 | 0.370 | 0.413 | 0.084 | -27 |
| Lg Intestine | 6.299 | 0.759 | 3.975 | 1.001 | -37 |
| Brain | 0.006 | 0.002 | 0.003 | 0.002 | -42 |
| Tumor (+) | 1.416 | 0.356 | 1.756 | 0.399 | 24 |
| Tumor (-) | 0.233 | 0.031 | 0.179 | 0.084 | -23 |
| | (%ID/g bars for 1, 2, 4 h-excl. urine) | | (%ID/g bars for 1, 2, 4 h-excl. urine) | | vs 5 (same organ & time) |
| Uptake ratios | | | | | |
| Organ 1/Organ 2 | | | | | |
| TUM(+)/TUM(-) | 6.08 | | 9.85 | | 62 |
| TUM(+)/Blood | 4.64 | | 16.83 | | 262 |
| TUM(+)/Kidney | 0.04 | | 0.14 | | 233 |
| TUM(+)/Liver | 4.74 | | 18.68 | | 294 |
| TUM(+)/Muscle | 1.95 | | 3.33 | | 70 |
| TUM(+)/Pancreas | 4.25 | | 13.01 | | 206 |
| | | | | | vs 5 (same organs & time) |

*FIG. 29*

BI-TERMINAL PEGYLATED INTEGRIN-BINDING PEPTIDES AND METHODS OF USE THEREOF

CROSS-REFERENCE TO RELATED APPLICATIONS

The present application is a continuation of U.S. application Ser. No. 15/292,564, filed Oct. 13, 2016, which is a continuation of International Application No. PCT/US2015/025700, filed Apr. 14, 2015, which claims priority to U.S. Provisional Application No. 61/979,997, filed Apr. 15, 2014, the contents of which are herein incorporated by reference in their entirety for all purposes.

STATEMENT AS TO RIGHTS TO INVENTIONS MADE UNDER FEDERALLY SPONSORED RESEARCH AND DEVELOPMENT

This invention was made with Government support under Grant No. DE-SC0002061, awarded by the Department of Energy, and Grant No. 1RC4EB012836-01, awarded by the National Institutes of Health. The Government has certain rights in this invention.

REFERENCE TO A SEQUENCE LISTING

The Sequence Listing written in file SL_070772-218020US-1214861.txt created on Oct. 12, 2020, 29,132 bytes, machine format IBM-PC, MS-Windows operating system, is hereby incorporated by reference in its entirety for all purposes.

BACKGROUND OF THE INVENTION

Integrins are a large family of cell-surface receptors responsible for mediating cell-cell and cell-extracellular matrix (ECM) adhesion. There are at least 24 different integrins, each a heterodimer composed of an $\alpha$ and $\beta$ subunit, whose expression is determined by several factors including tissue type, stage of development, and various tissue pathologies such as inflammation and cancer. Although they do not possess any intrinsic enzymatic activity, subsequent to ligand binding, integrins translate extracellular cues into intracellular signals by bringing into juxtaposition a complex of cytoplasmic structural and signaling molecules that then interact and determine the cellular response. As integrins are involved in most elements of cell behavior including motility, proliferation, invasion, and survival, their roles in disease have been widely reported. In fact, some integrins are thought to play an active role in promoting certain diseases including cancer. For example, $\alpha_v\beta_3$ integrin has been implicated in promoting the invasive phenotype of melanoma and glioblastoma, owing to its multiple abilities including upregulating pro-invasive metalloproteinases as well as providing pro-migratory and survival signals. As $\alpha_v\beta_3$ is also upregulated on endothelial cells of angiogenic blood vessels and may provide similar signals for the development of neo-vessels in cancer, such data have led many pharmaceutical and academic centers to develop antagonists of $\alpha_v\beta_3$ for therapeutic purposes, many of which have been peptides or peptidomimetics. Thus, understanding the structural basis of integrin-ligand interactions would aid in the design of improved integrin antagonists.

The $\alpha_v\beta_6$ integrin receptor is expressed only on epithelial cells. This integrin is involved in both normal and pathological tissue processes. For example, $\alpha_v\beta_6$ is upregulated by epithelial cells during wound healing and inflammation. It is likely that the ability of $\alpha_v\beta_6$ to locally activate TGF-$\beta$ by binding to its protective pro-peptide, the latency associated peptide (LAP), explains the function of this integrin in these transient pathologies. Thus, TGF-$\beta$ can suppress inflammatory responses and epithelial proliferation, indicating that $\alpha_v\beta_6$ serves as a negative control to dampen-down these processes. However, chronic inflammation can lead to an excess of $\alpha_v\beta_6$-dependent activation of TGF-$\beta$, resulting in fibrosis in the lung of experimental animals. As a result, some pathologies that result in fibrosis in humans may also involve $\alpha_v\beta_6$-dependent TGF-$\beta$ activation. Constitutive $\alpha_v\beta_6$ overexpression in the skin of mice results in chronic wounds appearing on a significant number of transgenic animals. As such, chronic wounds associated with human diseases (e.g., certain forms of epidermolysis bullosa) may also be promoted or exacerbated by upregulation of $\alpha_v\beta_6$ expressed by wound keratinocytes.

Recently, it has become clear that the $\alpha_v\beta_6$ integrin is a major new target in cancer. Although $\alpha_v\beta_6$ is epithelial-specific, it is weak or undetectable in most resting epithelial tissues but is strongly upregulated in many types of cancer, often at the invasive front. For example, $\alpha_v\beta_6$ is highly upregulated in oral squamous cell carcinoma (OSCC), pancreatic cancer, ovarian cancer, and colon cancer. It has been shown that $\alpha_v\beta_6$ can promote carcinoma invasion by upregulating metalloproteinases and promoting increased motility such that survival of carcinoma cells is promoted by upregulation of Akt. These data indicate that $\alpha_v\beta_6$ actively promotes the invasive phenotype. It has also been shown that high expression of $\alpha_v\beta_6$ correlates with a significant reduction in median survival by colon cancer patients.

In addition, $\alpha_v\beta_6$ integrin has been identified as a receptor for foot-and-mouth disease virus (FMDV) in vitro by binding through an RGD motif in the viral capsid protein, VP1. Structural studies have revealed that one of the modes by which FMDV binds to cells is via a small 31-amino acid containing loop on its protein-shell. This FMDV loop binds to $\alpha_v\beta_6$ with high selectivity and specificity. PCT Publication No. WO 07/039728 describes a radiolabeled $\alpha_v\beta_6$-targeting peptide, A20FMDV2, consisting of 20 core amino acids of the FMDV loop, which bound to immobilized human $\alpha_v\beta_6$ with high specificity and selectivity in competitive ELISA binding assays. The ability of radiolabeled A20FMDV2 to image $\alpha_v\beta_6$-expressing human tumors was also assessed using PET in an athymic nu/nu mouse model. However, these in vivo studies showed rapid metabolism of the radiolabeled $\alpha_v\beta_6$-targeting peptide. In fact, by one hour, radioactivity in the urine was distributed about equally between three metabolites and no unmetabolized peptide was detected. Washout of radioactivity from the $\alpha_v\beta_6$-expressing tumor was observed as well. In particular, the percent injected dose of peptide per gram of tumor (% ID/g) was 0.66, 0.28, and 0.06 at 1, 2, and 4 hours post injection, respectively.

In view of the foregoing, there is a need in the art for tumor targeting agents which not only provide high tumor selectivity and specificity for $\alpha_v\beta_6$-expressing tumors, but are also capable of having increased metabolic stability and retention in $\alpha_v\beta_6$-expressing tumors. The present invention satisfies this need and provides related advantages as well.

BRIEF SUMMARY OF THE INVENTION

The present invention provides bi-terminal PEGylated peptide conjugates that target an integrin such as $\alpha_v\beta_6$ integrin. In particular embodiments, the peptide conjugates of the present invention further comprise a biological agent such as an imaging agent or a therapeutic agent, e.g., covalently attached to one of the PEG moieties. The peptide conjugates of the present invention are particularly useful for imaging a tumor, organ, or tissue and for treating integrin-mediated diseases and disorders such as cancer, inflammatory diseases, autoimmune diseases, chronic fibrosis, chronic obstructive pulmonary disease (COPD), lung emphysema, and chronic wounding skin disease. Compositions and kits containing the peptide conjugates of the present invention find utility in a wide range of applications including, e.g., in vivo imaging and immunotherapy.

In one aspect, the present invention provides a conjugate comprising:
(a) a peptide that binds to an integrin;
(b) a first polyethylene glycol (PEG) moiety covalently attached to the amino-terminus of the peptide; and
(c) a second PEG moiety covalently attached to the carboxyl-terminus of the peptide.

In some embodiments, the peptide comprises an amino acid sequence selected from the group consisting of RGD, LDV, and GFOGER (SEQ ID NO:1), wherein 0 is hydroxyproline. In other embodiments, the integrin is $\alpha_v\beta_3$ integrin, $\alpha_{IIb}\beta_3$ integrin, or $\alpha_v\beta_6$ integrin. In preferred embodiments, the integrin is $\alpha_v\beta_6$ integrin. In certain embodiments, the $\alpha_v\beta_6$ integrin-binding peptide comprises the amino acid sequence RGDLX$_1$X$_2$X$_3$ (SEQ ID NO:2), wherein X$_1$ and X$_2$ are independently selected amino acids and X$_3$ is L or I. In certain embodiments, X$_1$ is Q, X$_2$ is V, and X$_3$ is L. In particular embodiments, the peptide comprises the amino acid sequence RGDLX$_1$X$_2$X$_3$AQX$_6$, wherein X$_6$ is K or R (SEQ ID NO: 3). In certain instances, X$_6$ is R. In other embodiments, the $\alpha_v\beta_6$ integrin-binding peptide comprises the amino acid sequence RSDLTPLFX$_7$, wherein X$_7$ is absent or is any amino acid (SEQ ID NO: 4). In certain instances, X$_7$ is absent (i.e., the peptide comprises the amino acid sequence RSDLTPLF (SEQ ID NO: 4)). In certain other instances, X$_7$ is K (i.e., the peptide comprises the amino acid sequence RSDLTPLFK (SEQ ID NO: 4)). In preferred embodiments, the peptide comprises or consists of an amino acid sequence selected from the group consisting of NAVPNLRGDLQVLAQKVART (A20FMDV2) (SEQ ID NO: 5) and NAVPNLRGDLQVLAQRVART (A20FMDV2 K16R) (SEQ ID NO: 5). In alternative embodiments, the peptide is a peptidomimetic that binds to the target integrin, e.g., $\alpha_v\beta_6$ integrin.

In other embodiments, the peptide binds to the integrin and a receptor that is co-expressed with the integrin. In certain instances, the receptor that is co-expressed with the integrin is C-X-C chemokine receptor type 4 (CXCR4). In further embodiments, the peptide is between about 8 and about 45 amino acids in length. In certain instances, the peptide is 20 amino acids in length.

In some embodiments, the first PEG moiety and the second PEG moiety each have a molecular weight of less than about 5000 daltons (Da), e.g., less than about 3000 Da. In preferred embodiments, the first PEG moiety and the second PEG moiety are monodisperse PEG moieties having a defined chain length. Non-limiting examples of PEG moieties having a defined chain length include small, monodisperse PEG molecules having greater than about 95% oligomer purity. In certain instances, the first PEG moiety and the second PEG moiety are independently selected from the group consisting of PEG$_{11}$, PEG$_{12}$ (PEG 800), PEG$_{28}$ (PEG 1500), and (PEG$_{28}$)$_2$ (PEG 1500×2). In particular embodiments, the first PEG moiety and the second PEG moiety are the same. In preferred embodiments, the first PEG moiety and the second PEG moiety are both PEG$_{28}$ (PEG 1500).

In certain embodiments, the conjugate further comprises an imaging agent or a therapeutic agent covalently attached to the peptide, the first PEG moiety, and/or the second PEG moiety. In particular embodiments, the imaging agent or therapeutic agent is covalently attached to the first PEG moiety. In certain instances, the imaging agent or therapeutic agent is covalently attached as the most N-terminal moiety in the conjugate.

In some embodiments, the imaging agent is selected from the group consisting of a radionuclide, biotin, a fluorophore, a fluorescent protein, an antibody, horseradish peroxidase, alkaline phosphatase, and combinations thereof. In certain embodiments, the radionuclide is selected from the group consisting of $^{11}$C, $^{13}$N, $^{15}$O, $^{18}$F, $^{19}$F, $^{61}$Cu, $^{62}$Cu, $^{64}$Cu, $^{67}$Cu, $^{68}$Ga, $^{124}$I, $^{125}$I, and $^{131}$I. In certain instances, the radionuclide is attached via a prosthetic group to the peptide, the first PEG moiety, or the second PEG moiety. In some instances, the radionuclide is attached via a prosthetic group as the most N-terminal moiety in the conjugate.

In some embodiments, the therapeutic agent is selected from the group consisting of a radionuclide, a pro-apoptotic peptide, a nanoparticle, a chemotherapeutic agent, a nanodroplet, a liposomal drug, a cytokine, and combinations thereof. In certain embodiments, the therapeutic agent is a radionuclide selected from the group consisting of $^{90}$Y and $^{177}$Lu. In certain instances, the radionuclide is attached via a chelating agent to the peptide, the first PEG moiety, or the second PEG moiety. In some instances, the radionuclide is attached via a chelating agent as the most N-terminal moiety in the conjugate.

In other embodiments, the therapeutic agent is a pro-apoptotic peptide comprising the amino acid sequence $_D$(KLAKLAK)$_2$ (SEQ ID NO: 6). In certain instances, the pro-apoptotic peptide is attached via a glycine linker to the peptide, the first PEG moiety, or the second PEG moiety. In particular instances, the pro-apoptotic peptide is attached, e.g., via a glycine linker, to the first PEG moiety.

In yet other embodiments, the therapeutic agent is a nanoparticle comprising a telodendrimer scaffold or other micelle-based nanocarrier system. In particular embodiments, the telodendrimer scaffold is PEG$^{5K}$CA$_8$. In certain instances, the nanoparticle is loaded with a chemotherapeutic agent. Non-limiting examples of chemotherapeutic agents include paclitaxel (PTX) and other cytotoxic chemotherapeutic agents described herein.

In certain embodiments, the conjugate further comprises an albumin binding motif covalently attached to the peptide, the first PEG moiety, or the second PEG moiety. In particular embodiments, the albumin binding motif is 4-(4-iodophenyl)butyric acid (IPA) or a homolog thereof with a shorter alkyl chain such as, e.g., 4-(4-iodophenyl)propionic acid or 4-(4-iodophenyl)acetic acid. In certain instances, the albumin binding motif is covalently attached to the first and/or second PEG moiety via a linker such as a glutamic acid (E) linker or other suitable linker (e.g., amino acid or peptide linker) known to one of skill in the art. In certain embodiments, the albumin binding motif is ε-(4-(4-iodophenyl)butyl amide)lysine-glutamic acid ("K(IPA)E"), which corresponds to IPA that is covalently attached to the side-chain of the lysine residue of a lysine-glutamic acid peptide linker. In some embodiments, the K(IPA)E albumin binding motif is covalently attached to the first PEG moiety. In other embodiments, the imaging agent or therapeutic agent is covalently attached (e.g., via a prosthetic group, a chelating agent, or a linker) to an albumin binding motif that is covalently attached to the first PEG moiety.

In another aspect, the present invention provides a composition comprising a bi-terminal PEGylated peptide conjugate described herein or a plurality thereof. In particular embodiments, the plurality of conjugates contains monodisperse PEG moieties having a defined chain length (e.g., greater than about 95% oligomer purity). In certain instances, the first PEG moiety and the second PEG moiety in each of the plurality of conjugates are independently selected from the group consisting of $PEG_{11}$, $PEG_{12}$ (PEG 800), $PEG_{28}$ (PEG 1500), and $(PEG_{28})_2$ (PEG 1500×2). In particular embodiments, the first PEG moiety and the second PEG moiety in each of the plurality of conjugates are the same. In preferred embodiments, the first PEG moiety and the second PEG moiety in each of the plurality of conjugates are both $PEG_{28}$ (PEG 1500).

In some embodiments, the present invention provides multimeric peptide conjugates wherein a plurality of the conjugates are linked to each other. In particular embodiments, the multimeric conjugate is a dimer or a tetramer of the plurality of conjugates. In certain embodiments, the multimeric peptide conjugates are formed via linkage between the second PEG moiety of each conjugate. In some instances, the conjugates are linked to each other at the second PEG moiety via at least one lysine residue. In other embodiments, the composition further comprises a pharmaceutical carrier or excipient.

In yet another aspect, the present invention provides a kit for imaging or therapy, the kit comprising:
  (a) a bi-terminal PEGylated peptide conjugate described herein or a composition thereof (e.g., a plurality or multimer of conjugates); and
  (b) directions for use of the conjugate or the composition in imaging or therapy.

In a further aspect, the present invention provides a method for the in vivo imaging of a target tissue, the method comprising:
  (a) administering to a subject in need of such imaging, a bi-terminal PEGylated peptide conjugate described herein or a composition thereof (e.g., a plurality or multimer of conjugates), wherein an imaging agent is covalently attached to the peptide, the first PEG moiety, or the second PEG moiety; and
  (b) detecting the conjugate to determine where the conjugate is concentrated in the subject.

In some embodiments, the target tissue is a cancerous tissue or an organ. Non-limiting examples of cancerous tissues include cancerous tissues or tumors associated with pancreatic cancer, breast cancer, colorectal cancer, prostate cancer, cervical cancer, and oral squamous cell carcinoma. In preferred embodiments, the peptide conjugate is administered for imaging a tumor such as a pancreatic tumor.

In other embodiments, the peptide conjugate is detected by Magnetic Resonance Imaging (MM), Magnetic Resonance Spectroscopy (MRS), Single Photon Emission Computerized Tomography (SPECT), Positron Emission Tomography (PET), or optical imaging. In yet other embodiments, the conjugate is detected for the diagnosis or prognosis of a disease or disorder mediated by the integrin. In certain embodiments, the disease or disorder is associated with the expression, overexpression, and/or activation of the integrin. In preferred embodiments, the disease or disorder is an $\alpha_v\beta_6$ integrin-mediated disease or disorder.

In a related aspect, the present invention provides a method for treating an integrin-mediated disease or disorder in a subject in need thereof, the method comprising:
administering to the subject a therapeutically effective amount of a bi-terminal PEGylated peptide conjugate described herein or a composition thereof (e.g., a plurality or multimer of conjugates), wherein a therapeutic agent is covalently attached to the peptide, the first PEG moiety, or the second PEG moiety.

In certain embodiments, the disease or disorder is associated with the expression, overexpression, and/or activation of the integrin. Non-limiting examples of integrin-mediated diseases or disorders include cancer, inflammatory diseases, autoimmune diseases, chronic fibrosis, chronic obstructive pulmonary disease (COPD), lung emphysema, and chronic wounding skin disease. In particular embodiments, the disease or disorder is an $\alpha_v\beta_6$ integrin-mediated disease or disorder. In some instances, the $\alpha_v\beta_6$ integrin-mediated disease or disorder is a cancer selected from the group consisting of pancreatic cancer, breast cancer, colorectal cancer, prostate cancer, cervical cancer, and oral squamous cell carcinoma.

Other objects, features, and advantages of the present invention will be apparent to one of skill in the art from the following detailed description and figures.

BRIEF DESCRIPTION OF THE DRAWINGS

Figure 17:
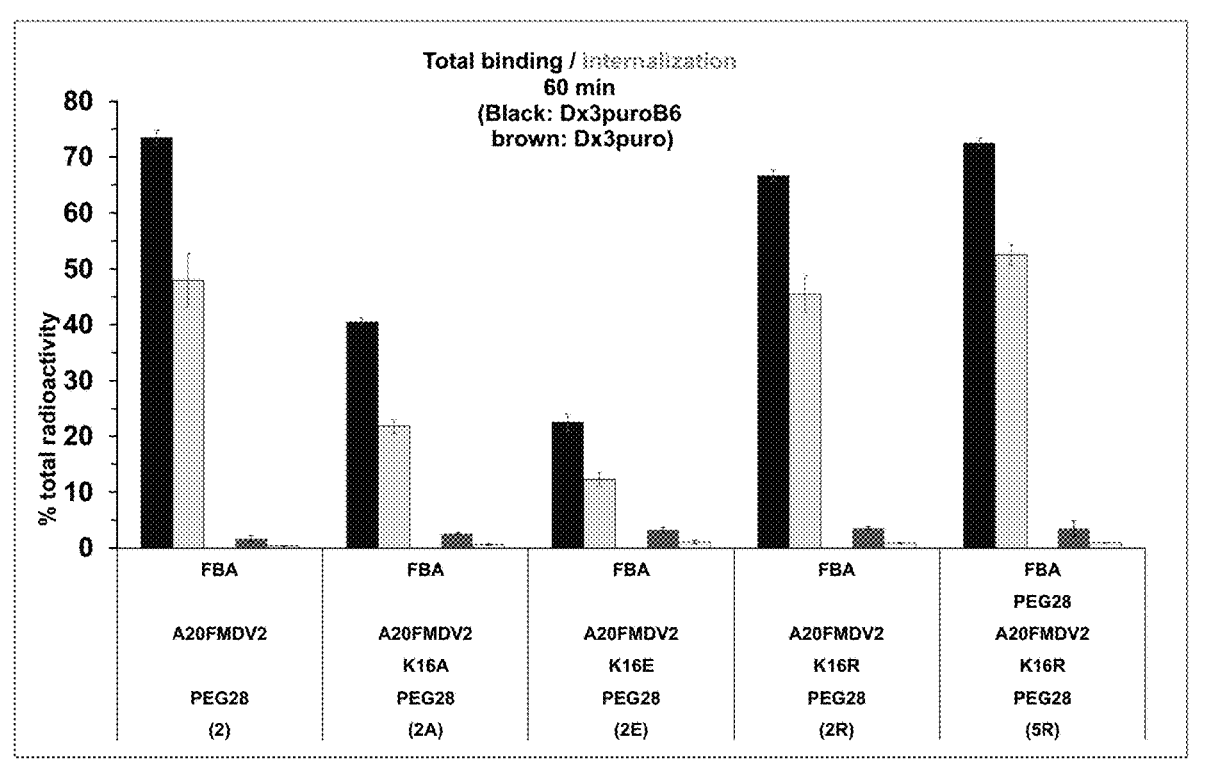

FIG. 17 shows binding and internalization of monoPEGylated and diPEGylated radiotracers with lysine substitutions in vitro using the integrin $\alpha_v\beta_6$-expressing DX3puroβ6 cell line and its non-expressing DX3puro control. The plots, displaying fraction of total radioactivity, represent quadruplicate experiments with $3.75 \times 10^6$ cells for each radiotracer/cell line after a 60 minute incubation period. Filled columns: percentage of total radioactivity detected in the cell sample (black: total bound; gray: internalized); bars: S.D.

FIG. 29 shows biodistribution data for 5 and 5R in paired DX3puroβ6/DX3puro mouse model 2 h after injection. Organ uptake is listed as % ID/g±S.D. (n=3/radiotracer/time point; with the exception of the $\alpha_v\beta_6$-positive target DX3puroβ6 tumor, low uptake is desirable). Also listed is the difference (relative % change) between 5R and 5 for each organ (with the exception of the $\alpha_v\beta_6$-positive target DX3puroβ6 tumor, a decrease is desirable) and uptake ratios between the $\alpha_v\beta_6$-positive DX3puroβ6 tumor and various organs (higher ratios are desirable).

DETAILED DESCRIPTION OF THE INVENTION

I. Introduction

Figure 1:
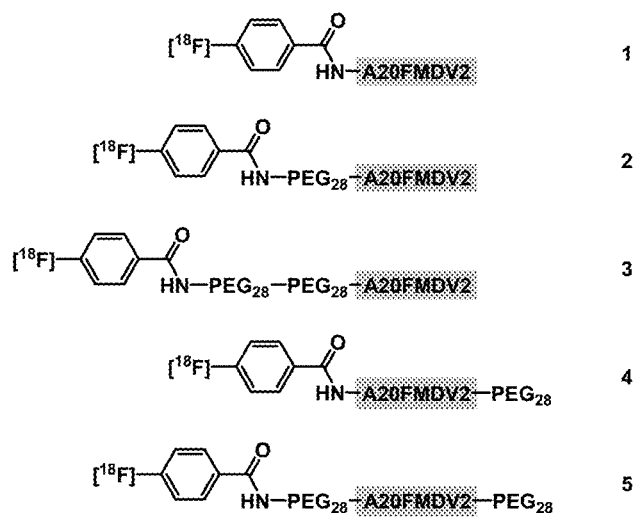
FIG. 1 shows the structures of exemplary PEGylation variations that were evaluated in the studies described herein. All compounds were obtained as C-terminal amides.
Figure 2:
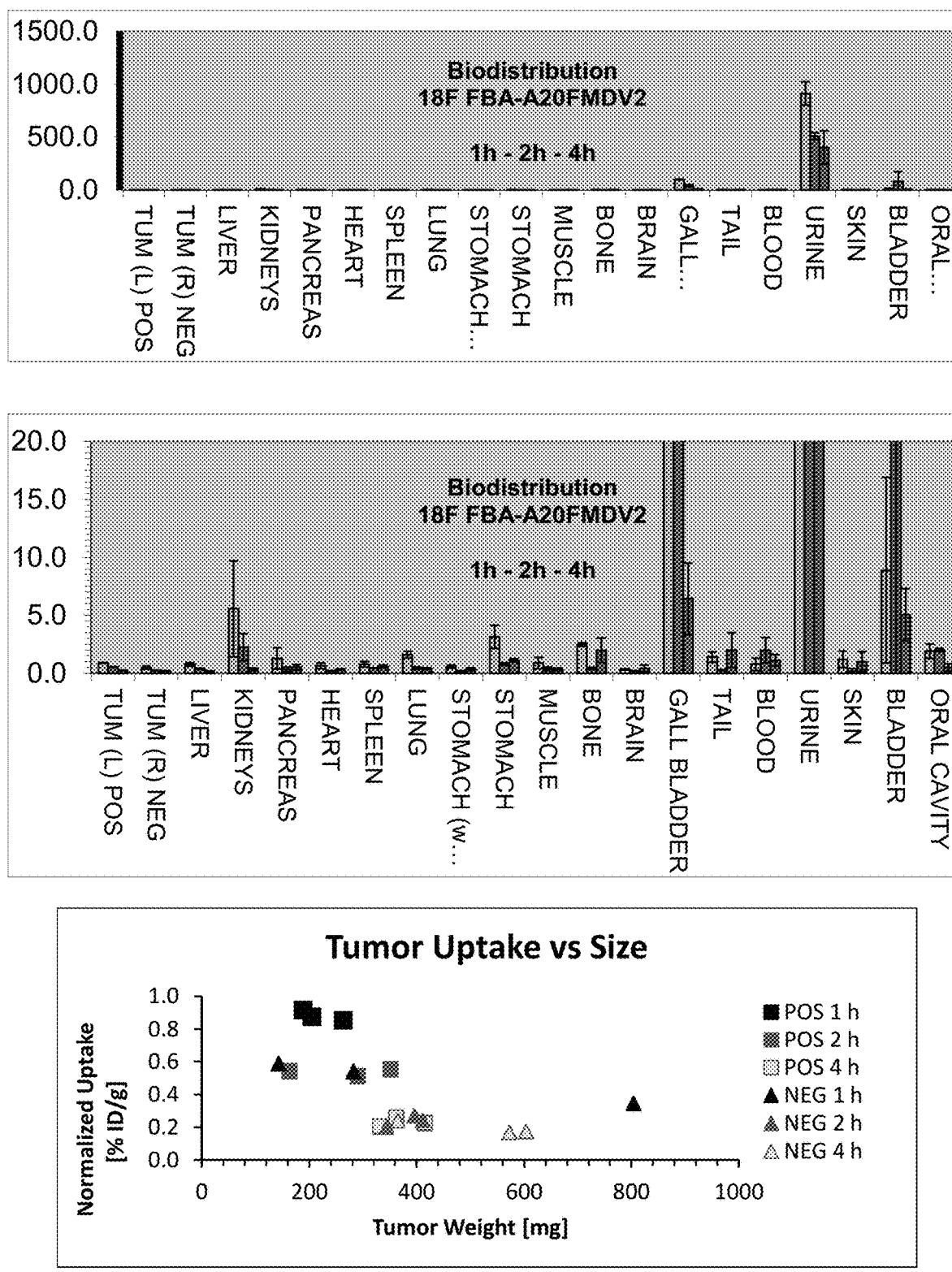
FIG. 2 shows biodistribution data for compound 1 (18F-FBA-A20FMDV2) in integrin $\alpha_v\beta_6$-expressing DX3puroβ6 tumors and non-expressing DX3puro control tumors.
Figure 3:
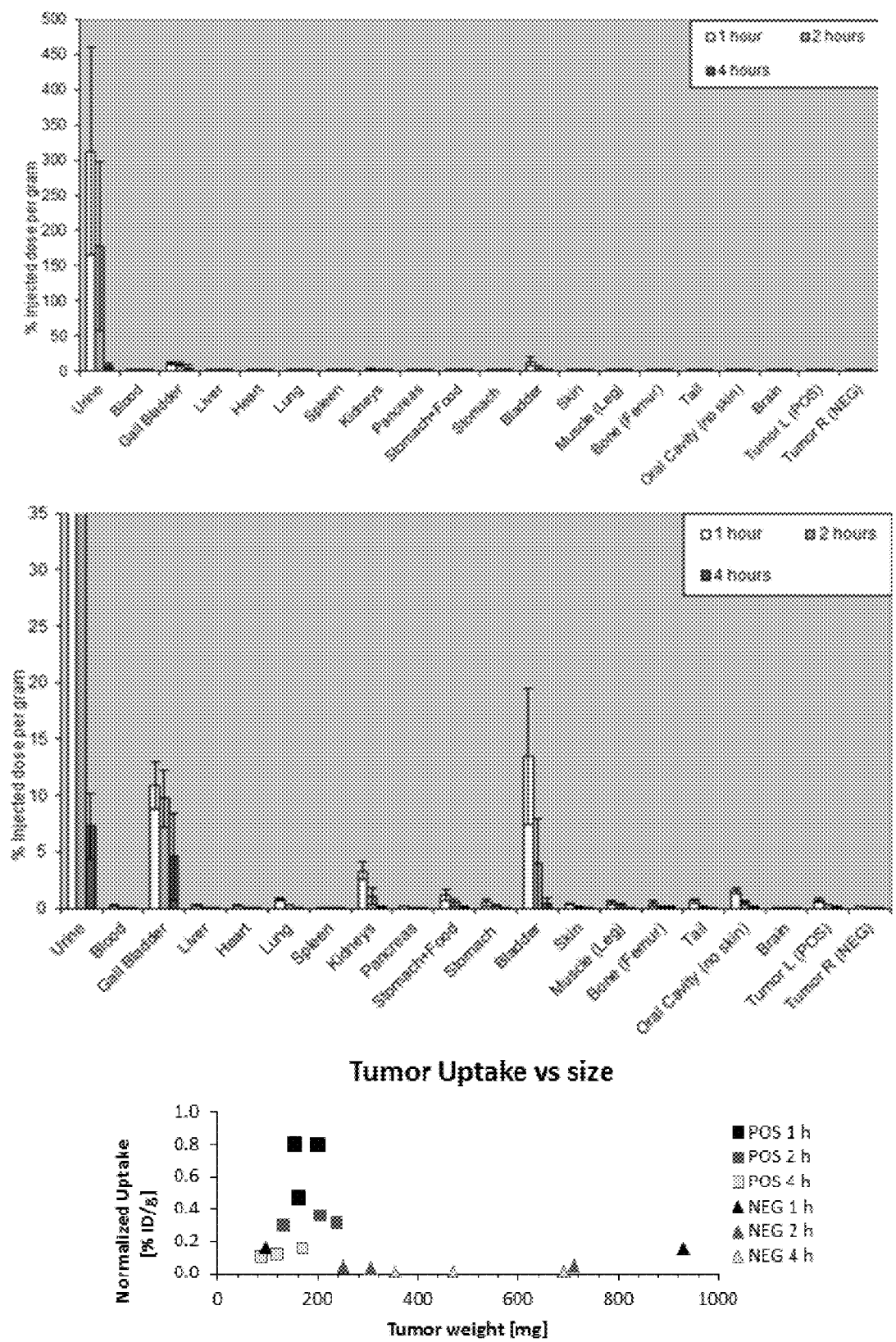
FIG. 3 shows biodistribution data for compound 1 (18F-FBA-A20FMDV2) in BxPC-3 (and MIA PaCa-2) tumors.
Figure 4:
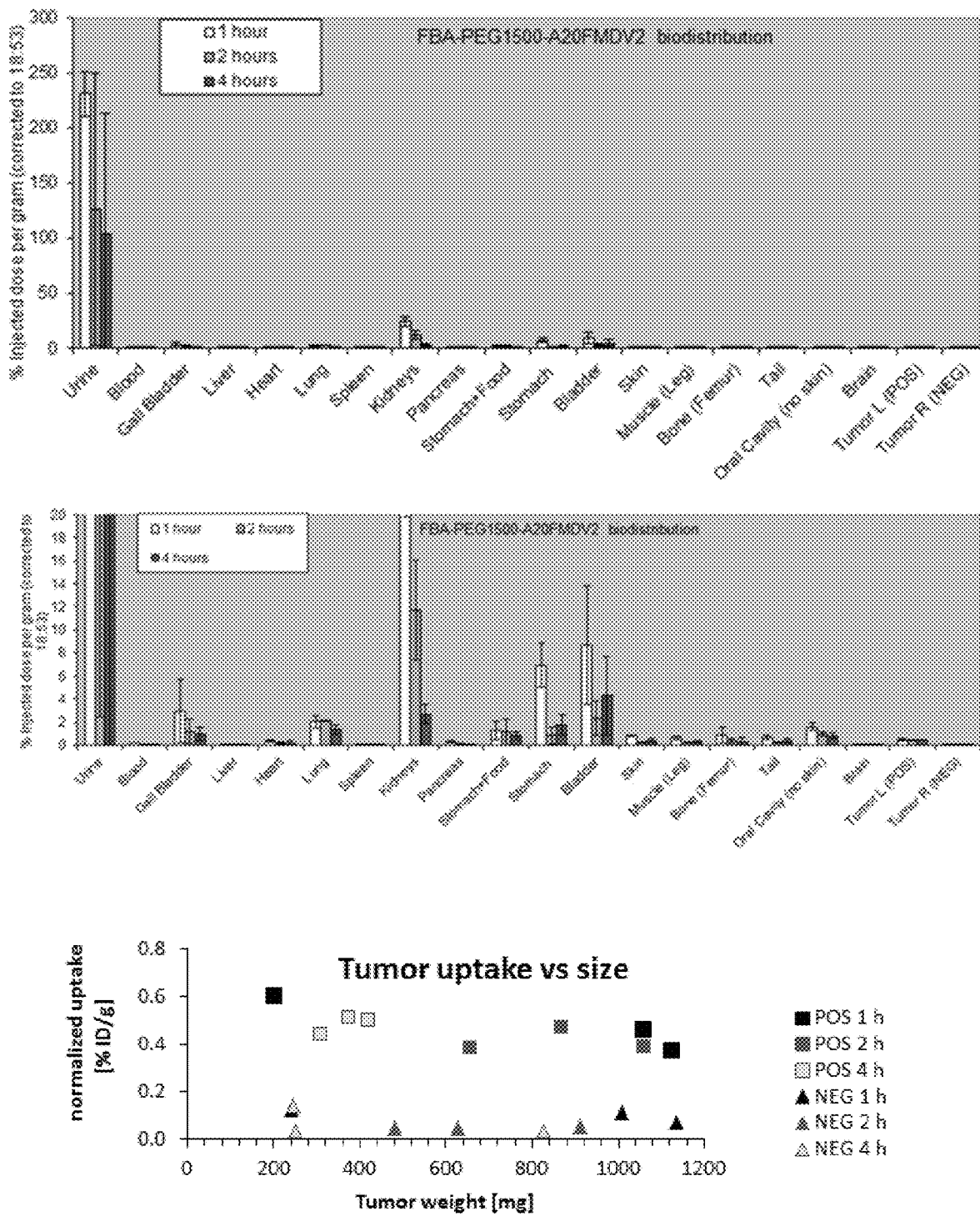
FIG. 4 shows biodistribution data for compound 2 (18F-FBA-PEG28-A20FMDV2) in DX3puroβ6 and Dx3puro tumors.
Figure 5:
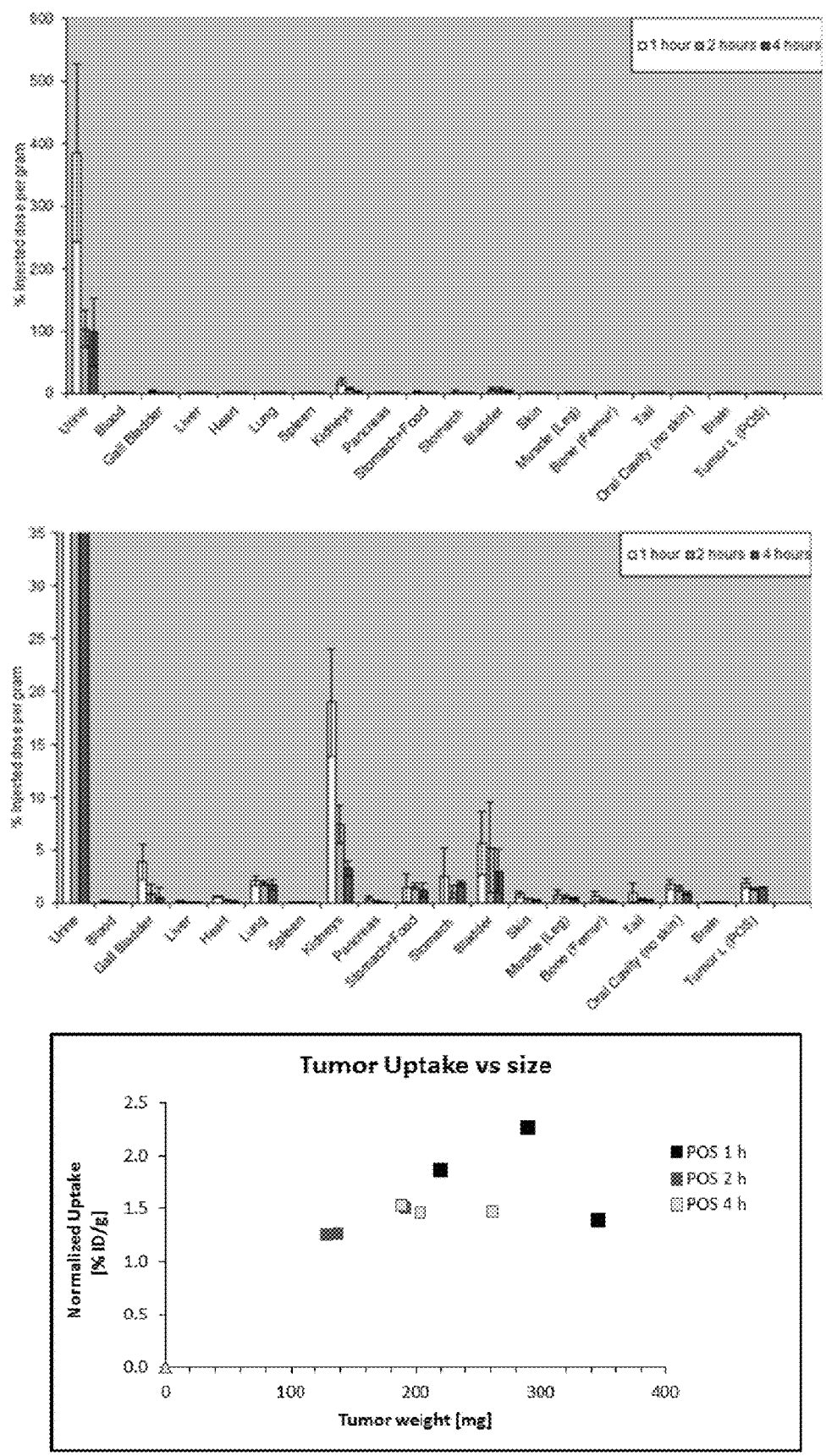
FIG. 5 shows biodistribution data for compound 2 (18F-FBA-PEG28-A20FMDV2) in BxPC-3 tumors.
Figure 6:
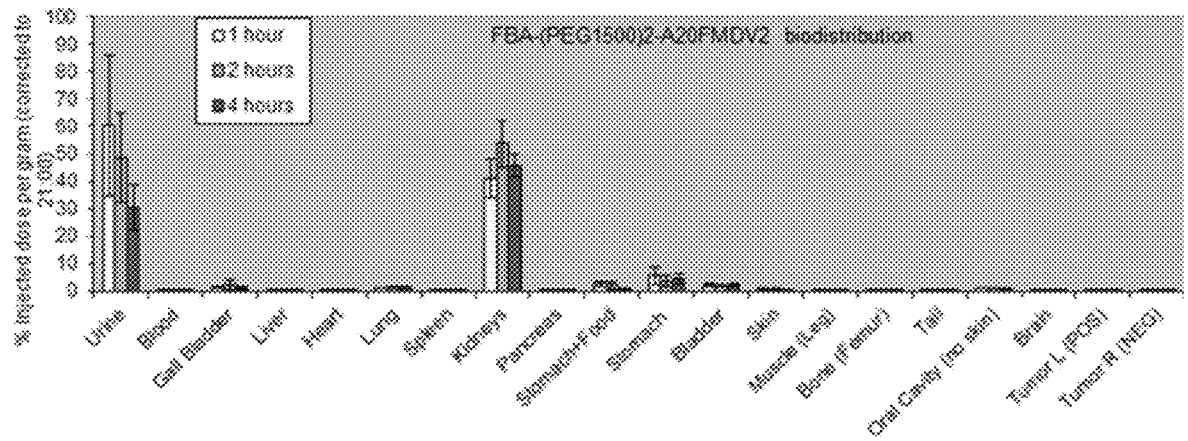
FIG. 6 shows biodistribution data for compound 3 (18F-FBA-PEG28-PEG28-A20FMDV2) in DX3puroβ6 and Dx3puro tumors.
Figure 6:
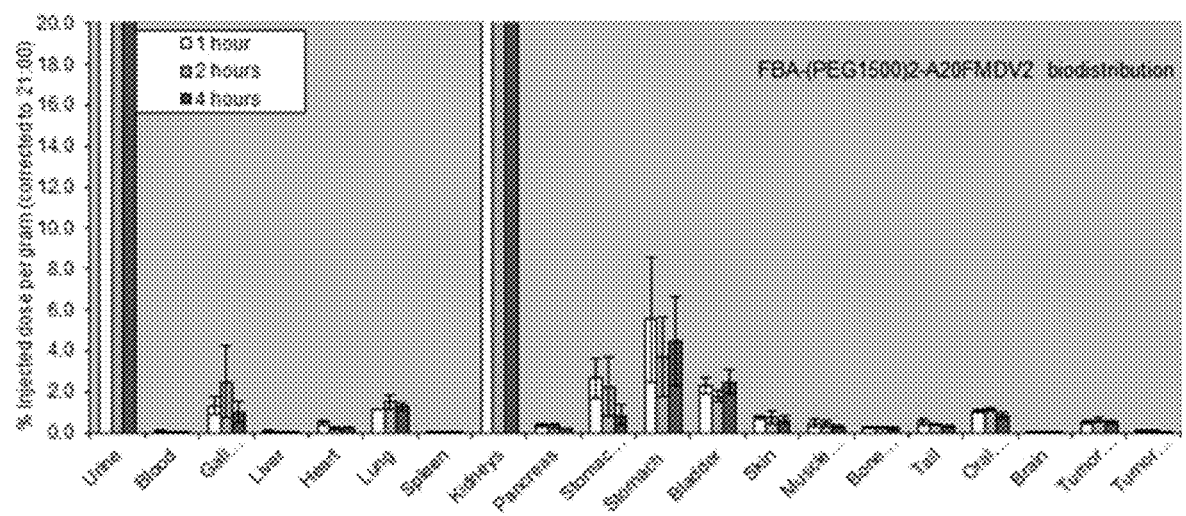
Figure 6:
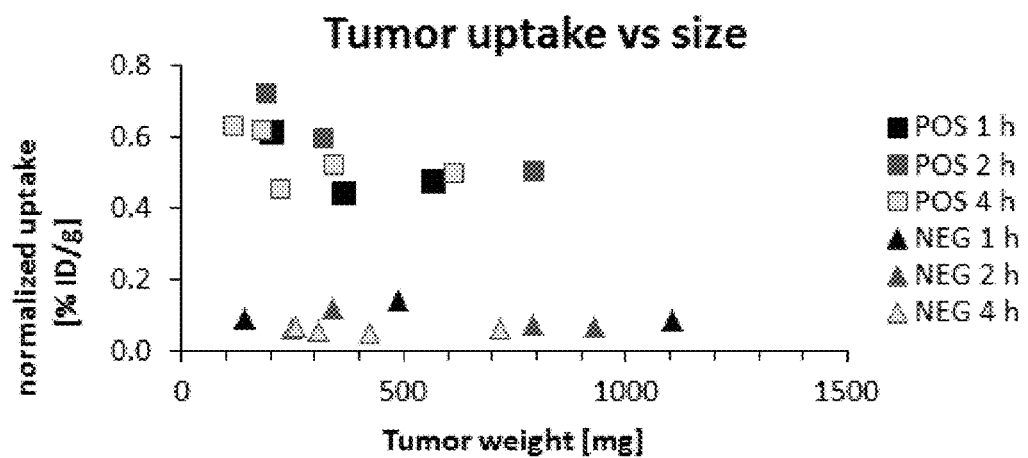
Figure 7:
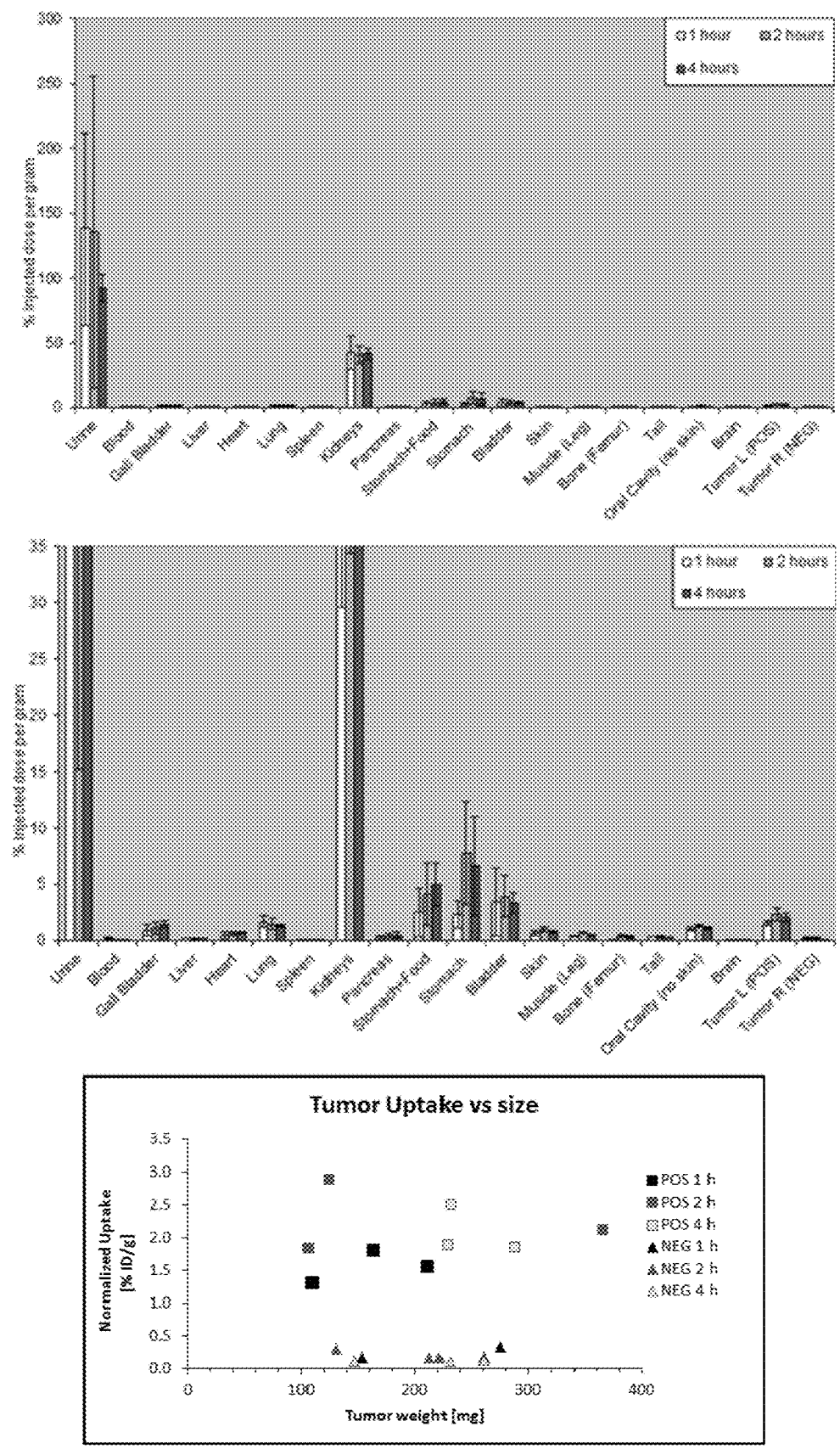
FIG. 7 shows biodistribution data for compound 3 (18F-FBA-PEG28-PEG28-A20FMDV2) in BxPC-3 (and MIA PaCa-2) tumors.

The present invention is based in part upon the surprising discovery that both the size and location of the PEG moiety on the integrin-binding peptide significantly affect the targeting and pharmacokinetic characteristics of the resulting peptide conjugate. In particular, Examples 1 and 2 illustrate that bi-terminal PEGylation (i.e., attaching PEG units at both the N- and C-termini of the peptide) was able to confer superior targeting characteristics and in vivo pharmacokinetics on the exemplary $\alpha_v\beta_6$ integrin-binding A20FMDV2 peptide and variants thereof (e.g., K16R variant). Notably, the bi-terminal PEGylated A20FMDV2 and A20FMDV2 (K16R) peptides showed greatly improved pharmacokinetic profiles beyond what was predicted from individual N- or C-terminal PEGylation. In fact, the two PEG units acted synergistically to achieve greatly improved stability alongside high $\alpha_v\beta_6(+)$-tumor uptake and retention. These effects were achieved with relatively small monodisperse PEG chains, e.g., PEG chains with an exactly defined number of ethylene glycol repeating units 'n', at the N- and at the C-terminus (e.g., MW <~3000), compared to PEG units commonly used for medical purposes (e.g., MW=~5000 to ~50,000).

As illustrated in Example 3, the present invention further provides novel molecular imaging and therapeutic agents with improved affinities and pharmacokinetics based on modifying the bi-terminal PEGylated peptide conjugates described herein with pro-apoptotic peptides, therapeutic radionuclides, micelle-based nanocarriers, multimerization, and/or the addition of blood albumin binding motifs to further improve the affinity, in vivo stability, targeting capabilities, and/or clearance behavior of the peptide conjugates.

Moreover, the results presented in Example 4 demonstrate that bi-terminal PEGylation of an integrin-binding peptide as short as 8 amino acids with even shorter PEG units (e.g., $PEG_{11}$) imparts advantageous properties to the peptide such as high selectively, improved serum stability, radiolabeling yields, and lipophilicity when compared to the parent peptide sequence, a cyclic version of the peptide, and individual N- or C-terminal PEGylated versions of the peptide. As such, bi-terminal PEGylated peptide conjugates of the present invention having short peptide sequences (e.g., about 8 amino acids in length) and short PEG units (e.g., $PEG_{11}$) have desirable targeting and pharmacokinetic characteristics that make them suitable for in vivo imaging and therapy.

The bi-terminal PEGylated peptide conjugates of the present invention can be prepared using standard methods. Only relatively short PEG polymers are needed, allowing synthesis on solid phase. This ensures straightforward preparation and purification. The peptide conjugate is obtained as a single compound of precise composition and molecular mass, compared to other PEGylated compounds which may display positional isomerism and contain mixtures of PEG chains with an average length.

Taken together, the imaging and targeting of integrin (e.g., $\alpha_v\beta_6$) expression in tumors with the peptide conjugates of the present invention result in the detection and treatment of otherwise overlooked tumors, and also serve as a prognostic indicator of cancer in a non-invasive way.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The term "conjugate" is intended to include a chemical compound that has been formed by the joining or attachment of two or more compounds. In particular, a conjugate of the present invention includes a "bi-terminal PEGylated peptide conjugate" comprising an integrin-binding peptide covalently attached to a first polyethylene glycol (PEG) moiety at the amino-terminus of the peptide and a second PEG moiety at the carboxyl-terminus of the peptide. The conjugate of the present invention can further comprise an imaging agent or a therapeutic agent covalently attached to the peptide, the first PEG moiety, or the second PEG moiety.

The terms "integrin-binding peptide" and "peptide that binds to an integrin" refer to the binding/interaction of a peptide motif in the conjugate which shows the capacity of specific interaction with a specific integrin or a specific group of integrins. In certain embodiments, the terms refer to the ability of a peptide or a portion thereof to interact with and/or bind to a target integrin and without cross-reacting with molecules of similar sequences or structures. In some instances, a peptide specifically binds to a target integrin when it binds to the target integrin with a substantially lower dissociation constant (i.e., tighter binding) than a molecule of similar sequence or structure. For example, in certain instances, a specific binding occurs when the peptide binds to the target integrin with an about 2, 3, 4, 5, 6, 8, 10, 15, 20, 25, 30, 40, 50, 100, or 1000-fold or greater affinity than a related molecule. The binding of the peptide to a site on the target integrin may occur via intermolecular forces such as ionic bonds, hydrogen bonds, hydrophobic interactions, dipole-dipole bonds, and/or Van der Waals forces. Cross-reactivity may be tested, for example, by assessing binding of the peptide under conventional conditions to the target integrin as well as to a number of more or less (e.g., structurally and/or functionally) closely related molecules. These methods may include, without limitation, binding studies, blocking and competition studies with closely related molecules, FACS analysis, surface plasmon resonance (e.g., with BIAcore), analytical ultracentrifugation, isothermal titration calorimetry, fluorescence anisotropy, fluorescence spectroscopy, radiolabeled ligand binding assays, and combinations thereof.

As used herein, the term "PEGylation" refers to the process of covalently coupling a polyethylene glycol (PEG) molecule to another molecule, e.g., a peptide, polypeptide, protein, antibody, and the like, which is then referred to as "PEGylated." As a non-limiting example, an integrin-binding peptide may be PEGylated at both the amino-terminus and the carboxyl terminus with monodisperse PEG molecules having a defined chain length to generate the bi-terminal PEGylated peptide conjugates of the invention. Monodisperse PEG molecules typically comprise discrete molecular weights with an exactly defined number of repeating ethylene glycol units. PEG moieties suitable for use in the present invention are commercially available from Polypure AS (Oslo, Norway), which supplies monodisperse PEG molecules and PEG derivatives thereof consisting of substantially one oligomer only (e.g., greater than about 90%, 91%, 92%, 93%, 94%, 95%, 96%, 97%, 98%, or 99% oligomer purity). In particular embodiments, the integrin-binding peptide is PEGylated at both ends with a single type or mixtures of different types of monodisperse PEG moieties having a molecular weight of less than about 3000 daltons (Da), such as, e.g., $PEG_{11}$, $PEG_{12}$ (PEG 800), $PEG_{28}$ (PEG 1500), and/or $(PEG_{28})_2$ (PEG 1500×2).

A "peptidomimetic" refers to a chemical compound having a structure that is different from the general structure of an existing peptide, but that functions in a manner similar to the existing peptide, e.g., by mimicking the biological activity of that peptide. Peptidomimetics typically comprise naturally-occurring amino acids and/or unnatural amino acids, but can also comprise modifications to the peptide backbone. Peptidomimetics can exhibit increased affinity, specificity, and/or stability compared to an existing peptide.

The term "amino acid" includes naturally-occurring α-amino acids and their stereoisomers, as well as unnatural amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups.

Non-limiting examples of unnatural amino acids include 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine (Tyr(3,5-di $NO_2$)), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzylhydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo [3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl)carboxylic acid (Ahch), 1-amino-1-(4-ketocyclohexyl)carboxylic acid (Akch), 4-amino-4-carboxytetrahydropyran (Actp), 3-nitrotyrosine (Tyr(3-$NO_2$)), 1-amino-1-cyclohexane carboxylic acid (Ach), 1-amino-1-(3-piperidinyl) carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, derivatives of lysine, ornithine (Orn) and α,γ-diaminobutyric acid (Dbu), stereoisomers thereof, and combinations thereof (see, e.g., Liu et al., *Anal.*

*Biochem.*, 295:9-16 (2001)). As such, the unnatural α-amino acids are present either as unnatural L-α-amino acids, unnatural D-α-amino acids, or combinations thereof.

"Amino acid mimetics" are chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

"N-substituted glycines" are unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs. Non-limiting examples of N-substituted glycines include N-(2-aminoethyl)glycine, N-(3-aminopropyl)glycine, N-(2-methoxyethyl)glycine, N-benzylglycine, (S)—N-(1-phenylethyl)glycine, N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(p-chlorophenylethyl)glycine, and N-[2-(p-hydroxyphenylethyl)]glycine. N-substituted glycine oligomers, referred to herein as "peptoids," have been shown to be protease resistant (see, e.g., Miller et al., *Drug Dev. Res.*, 35:20-32 (1995)).

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins,* 1993).

The term "peptide" refers to a compound made up of a single chain of D- or L-amino acids or a mixture of D- and L-amino acids joined by peptide bonds. Generally, peptides are about 2 to about 50 amino acids in length. As non-limiting examples, the integrin-binding peptides present in the conjugates described herein are between about 5 to about 45 amino acids in length, between about 8 to about 45 amino acids in length, between about 8 to about 25 amino acids in length, between about 8 to about 20 amino acids in length, between about 12 to about 45 amino acids in length, between about 12 to about 30 amino acids in length, about 8 amino acids in length, or about 20 amino acids in length.

A "cyclic peptide" refers to a peptide in which the amino-terminus of the peptide or a side-chain on the peptide having a free amino group (e.g., lysine) is joined by a peptide bond to the carboxyl-terminus of the peptide or a side-chain on the peptide having a free carboxyl group (e.g., aspartic acid, glutamic acid). However, one skilled in the art will appreciate that heterodetic cyclic peptides formed by disulfide, ester, or ether bonds are also within the scope of the present invention.

The term "helix-promoting residue" includes amino acids with a conformational preference greater than 1.0 for being found in the middle of an α-helix (see, e.g., Creighton, *Proteins,* 1993; and Pace et al., *Biophysical J.,* 75:422-427 (1998)). However, non-orthodox helix-promoting combinations of amino acids are also within the scope of the invention if they enhance the specificity and/or affinity of binding to a target integrin, e.g., $\alpha_v\beta_6$ integrin.

The term "therapeutically effective amount" refers to the amount of a conjugate or composition of the present invention that is capable of achieving a therapeutic effect in a subject in need thereof. For example, a therapeutically effective amount of a conjugate or composition of the present invention can be the amount that is capable of preventing or relieving one or more symptoms associated with a disease or disorder. One skilled in the art will appreciate that the conjugates and compositions of the present invention can be co-administered with other therapeutic agents such as anticancer, anti-inflammatory, immunosuppressive, antiviral, antibiotic, and/or antifungal agents.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a conjugate or composition of the present invention for preventing or relieving one or more symptoms associated with a disease or disorder such as cancer or an inflammatory or autoimmune disease. By "co-administer" it is meant that a conjugate or composition of the present invention is administered at the same time, just prior to, or just after the administration of a second drug (e.g., anticancer agent, anti-inflammatory agent, immunosuppressive agent, antiviral agent, antibiotic, antifungal agent, etc.).

The term "radionuclide" is intended to include any nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Examples of radionuclides suitable for use in the present invention include, but are not limited to, fluorine 18 ($^{18}F$), fluorine 19 ($^{19}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$) gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$) iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth ($^{212}Bi$). As used herein, the "m" in $^{117m}Sn$ and $^{99m}Tc$ stands for the meta state. Additionally, naturally-occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$, $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{68}Ga$, $^{82}Rb$, and $^{86}Y$ are examples of positron-emitting radionuclides. $^{64}Cu$ is a beta- and positron-emitting radionuclide.

The term "subject" or "patient" typically refers to humans, but can also include other animals such as, e.g., other primates, rodents, canines, felines, equines, ovines, porcines, and the like.

III. Description of the Embodiments

The present invention provides bi-terminal PEGylated peptide conjugates that target an integrin such as $\alpha_v\beta_6$ integrin. In particular embodiments, the peptide conjugates of the present invention further comprise a biological agent such as an imaging agent or a therapeutic agent, e.g., covalently attached to one of the PEG moieties. The peptide conjugates of the present invention are particularly useful for imaging a tumor, organ, or tissue and for treating integrin-mediated diseases and disorders such as cancer, inflammatory diseases, autoimmune diseases, chronic fibrosis, chronic obstructive pulmonary disease (COPD), lung emphysema, and chronic wounding skin disease. Compositions and kits containing the peptide conjugates of the present invention find utility in a wide range of applications including, e.g., in vivo imaging and immunotherapy.

In one aspect, the present invention provides a conjugate comprising:
- (a) a peptide that binds to an integrin;
- (b) a first polyethylene glycol (PEG) moiety covalently attached to the amino-terminus of the peptide; and
- (c) a second PEG moiety covalently attached to the carboxyl-terminus of the peptide.

In some embodiments, the peptide comprises an amino acid sequence selected from the group consisting of RGD, LDV, and GFOGER (SEQ ID NO:1), wherein O is hydroxyproline. In other embodiments, the integrin is $\alpha_v\beta_3$ integrin, $\alpha_{IIb}\beta_3$ integrin, or $\alpha_v\beta_6$ integrin. In preferred embodiments, the integrin is $\alpha_v\beta_6$ integrin.

In certain embodiments, the $\alpha_v\beta_6$ integrin-binding peptide comprises the amino acid sequence RGDLX$_1$X$_2$X$_3$ (SEQ ID NO: 2), wherein X$_1$ and X$_2$ are independently selected amino acids and X$_3$ is L or I. In some instances, X$_1$ and X$_2$ are independently selected from the group consisting of Glu, Ala, Leu, Met, Gln, Lys, Arg, Val, Ile, His, Thr, Trp, Phe, and Asp. In certain embodiments, X$_1$ is Q, X$_2$ is V, and X$_3$ is L. In particular embodiments, the peptide comprises the amino acid sequence RGDLX$_1$X$_2$X$_3$AQX$_6$ (SEQ ID NO: 3), wherein X$_6$ is K or R. In certain instances, X$_6$ is R. In preferred embodiments, the $\alpha_v\beta_6$ integrin-binding peptide comprises or consists of an amino acid sequence selected from the group consisting of NAVPNLRGDLQVLAQKVART (SEQ ID NO: 5) (A20FMDV2) and NAVPNLRGDLQVLAQRVART (A20FMDV2 K16R) (SEQ ID NO: 5).

In other embodiments, the $\alpha_v\beta_6$ integrin-binding peptide comprises the amino acid sequence RSDLTPLFX$_7$ (SEQ ID NO: 4), wherein X$_7$ is absent or is any amino acid. In certain instances, X$_7$ is absent (i.e., the peptide comprises or consists of the amino acid sequence RSDLTPLF (SEQ ID NO: 4)). In certain other instances, X$_7$ is K (i.e., the peptide comprises or consists of the amino acid sequence RSDLTPLFK (SEQ ID NO: 4)).

In other embodiments, the peptide binds to the integrin and a receptor that is co-expressed with the integrin. In certain instances, the receptor that is co-expressed with the integrin is C-X-C chemokine receptor type 4 (CXCR4). In particular instances, the peptide binds to both $\alpha_v\beta_6$ integrin and CXCR4. In certain other instances, the receptor that is co-expressed with the integrin is another integrin, e.g., $\alpha_v\beta_3$ integrin co-expressed with $\alpha_v\beta_5$ integrin. In particular instances, the peptide binds to both $\alpha_v\beta_3$ integrin and $\alpha_v\beta_5$ integrin. In further embodiments, the peptide is between about 8 and about 45 amino acids in length. In certain instances, the peptide is 20 amino acids in length.

In some embodiments, the first PEG moiety and the second PEG moiety each have a molecular weight of less than about 5000 daltons (Da). In particular embodiments, the first PEG moiety and the second PEG moiety each have a molecular weight of less than about 3000 daltons (Da). In preferred embodiments, the first PEG moiety and the second PEG moiety are monodisperse PEG moieties having a defined chain length. PEG moieties having a defined chain length generally include PEG molecules of discrete molecular weights with an exactly defined number of repeating ethylene glycol units. Non-limiting examples of PEG moieties having a defined chain length include small, monodisperse PEG molecules having greater than about 90%, 91%, 92%, 93%, 94%, or 95% oligomer purity. In particular embodiments, PEG compound mixtures having an average molecular weight are not used in the conjugates of the present invention.

In certain instances, the first PEG moiety and the second PEG moiety are independently selected from the group consisting of PEG$_{11}$, PEG$_{12}$ (PEG 800), PEG$_{28}$ (PEG 1500), and (PEG$_{28}$)$_2$ (PEG 1500×2). In particular embodiments, the first PEG moiety and the second PEG moiety are the same. In preferred embodiments, the first PEG moiety and the second PEG moiety are both PEG$_{28}$ (PEG 1500). Other non-limiting examples of PEG units suitable for use as the first and/or second PEG moiety in the conjugates of the present invention include PEG 200, PEG 300, PEG 400, PEG 500, PEG 600, PEG 700, PEG 900, PEG 1000, PEG 1100, PEG 1200, PEG 1300, PEG 1400, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, and PEG 5000, as well as derivatives thereof such as branched PEG derivatives. In preferred embodiments, these PEG molecules contain an exactly defined number of repeating units "n" and are monodisperse (e.g., having greater than about 95% oligomer purity). PEG moieties suitable for use in the present invention are commercially available from EMD Chemicals, Inc. (San Diego, Calif.) and Polypure AS (Oslo, Norway).

In certain embodiments, the conjugate further comprises an imaging agent or a therapeutic agent covalently attached to the peptide, the first PEG moiety, and/or the second PEG moiety. In particular embodiments, the imaging agent or therapeutic agent is covalently attached to the first PEG moiety. In certain instances, the imaging agent or therapeutic agent is covalently attached as the most N-terminal moiety in the conjugate.

In some embodiments, the imaging agent is selected from the group consisting of a radionuclide, biotin, a fluorophore, a fluorescent protein, an antibody, horseradish peroxidase, alkaline phosphatase, and combinations thereof. In certain embodiments, the radionuclide is selected from the group consisting of $^{11}$C, $^{13}$N, $^{15}$O, $^{18}$F, $^{19}$F, $^{61}$Cu, $^{62}$Cu, $^{64}$Cu, $^{67}$Cu, $^{68}$Ga, $^{124}$I, $^{125}$I, and $^{131}$I. In certain instances, the radionuclide is attached via a prosthetic group to the peptide, the first PEG moiety, or the second PEG moiety. In particular embodiments, the radionuclide is attached via a prosthetic group to the first PEG moiety. In other embodiments, the radionuclide is attached via a prosthetic group as the most N-terminal moiety in the conjugate. Non-limiting examples of prosthetic groups include benzoyl groups (e.g., fluorobenzoic acid (FBA)), fluoropropionic acid (FPA), pyridine (Py), dipyridyl-tetrazine (Tz), trans-cyclooctene (TCO), derivatives thereof, and combinations thereof. In preferred embodiments, the radionuclide is $^{18}$F or $^{19}$F covalently attached to the first PEG moiety via a benzoyl group such as FBA. For example, 4-[$^{18}$F]-fluorobenzoic acid ([$^{18}$F]FBA) or 4-[$^{19}$F]-fluorobenzoic acid ([$^{19}$F]FBA) can be used to radiolabel the peptide conjugates of the present invention.

In some embodiments, the therapeutic agent is selected from the group consisting of a radionuclide, a pro-apoptotic peptide, a nanoparticle, a chemotherapeutic agent, a nanodroplet, a liposomal drug, a cytokine, and combinations thereof. In certain embodiments, the therapeutic agent is a radionuclide selected from the group consisting of $^{90}$Y and $^{177}$Lu. In certain instances, the radionuclide is attached via a chelating agent to the peptide, the first PEG moiety, or the second PEG moiety. In particular embodiments, the radionuclide is attached via a chelating agent to the first PEG moiety. In other embodiments, the radionuclide is attached via a chelating agent as the most N-terminal moiety in the conjugate. Non-limiting examples of chelating agents include macrocyclic metal chelators such as DOTA (1,4,7,10-tetraazacyclododecane-N,N',N'',N'''-tetraacetic acid), NOTA (1,4,7-triazacyclononane-N,N',N''-triacetic acid), DTPA (diethylenetriaminepentaacetic anhydride), TETA (1,4,8,11-tetraazacyclotetradecane-N,N',N'',N'''-tetraacetic acid), and DTTA (N-(p-isothiocyanatobenzyl)-diethylenetriamine-N,N',N'',N'''-tetraacetic acid).

In other embodiments, the therapeutic agent is a pro-apoptotic peptide comprising the amino acid sequence $_D$(KLAKLAK)$_2$ (SEQ ID NO: 6). In certain instances, the pro-apoptotic peptide is attached via a glycine linker to the peptide, the first PEG moiety, or the second PEG moiety. In particular embodiments, the pro-apoptotic peptide is attached via a glycine linker to the first PEG moiety. Non-limiting examples of glycine linkers include a single glycine residue or at least about 2, 3, 4, 5, 6, 7, 8, 9, 10, 11, 12, 13, 14, 15, 16, 17, 18, 19, or 20 consecutive glycine residues or glycine residues separated by other amino acid residues. In preferred embodiments, the glycine linker is a glycinylglycine linker. One skilled in the art will know of other linkers suitable for attaching the pro-apoptotic peptide to the peptide conjugates of the present invention, e.g., without significantly interfering with the targeting properties and function of each individual component.

In yet other embodiments, the therapeutic agent is a nanoparticle comprising a telodendrimer scaffold or other micelle-based nanocarrier system. In particular embodiments, the telodendrimer scaffold is PEG$^{5K}$CA$_8$. Telodendrimers suitable for use in the present invention are described in US Patent Publication No. 20130164369, the disclosure of which is hereby incorporated by reference in its entirety for all purposes. In certain instances, the nanoparticle is loaded with a chemotherapeutic agent. Non-limiting examples of chemotherapeutic agents include paclitaxel (PTX) and other cytotoxic chemotherapeutic agents described herein.

In certain embodiments, the conjugate further comprises an albumin binding motif covalently attached to the peptide, the first PEG moiety, or the second PEG moiety. In particular embodiments, the albumin binding motif is 4-(4-iodophenyl)butyric acid (IPA) or a homolog thereof with a shorter alkyl chain such as, e.g., 4-(4-iodophenyl)propionic acid or 4-(4-iodophenyl)acetic acid. In other embodiments, the albumin binding motif is 4-(4-methylphenyl)butyric acid or 4-(4-bromophenyl)butyric acid or a homolog thereof with a shorter alkyl chain such as, e.g., a propionic acid or acetic acid homolog thereof. In particular embodiments, the albumin binding motif is covalently attached to the first and/or second PEG moiety. In certain instances, the albumin binding motif is covalently attached to the first and/or second PEG moiety via a linker such as a glutamic acid (E) linker or other suitable linker (e.g., amino acid or peptide linker) known to one of skill in the art. In certain embodiments, the albumin binding motif is ε-(4-(4-iodophenyl)butyl amide) lysine-glutamic acid ("K(IPA)E"), which corresponds to IPA that is covalently attached to the side-chain of the lysine residue of a lysine-glutamic acid peptide linker. In some embodiments, the K(IPA)E albumin binding motif is covalently attached to the first PEG moiety. In other embodiments, the imaging agent or therapeutic agent is covalently attached (e.g., via a prosthetic group, a chelating agent, or a linker) to an albumin binding motif that is covalently attached to the first PEG moiety, such that the imaging agent or therapeutic agent is the most N-terminal moiety in the conjugate.

In another aspect, the present invention provides a composition comprising a bi-terminal PEGylated peptide conjugate described herein or a plurality thereof (e.g., at least about 2, 3, 4, 5, 6, 7, 8, 9, 10, 11, 12, 13, 14, 15, 16, 17, 18, 19, 20, 25, 30, or more peptide conjugates of the invention that differ, e.g., in their integrin-binding peptide sequences, first and/or second PEG moieties, imaging and/or therapeutic agents, or combinations thereof). In particular embodiments, the plurality of conjugates (i.e., the first and second PEG moieties in each of the plurality of conjugates) comprises monodisperse PEG moieties having a defined chain length (e.g., greater than about 90%, 91%, 92%, 93%, 94%, or 95% oligomer purity). In certain instances, the first PEG moiety and the second PEG moiety in each of the plurality of conjugates are independently selected from the group consisting of PEG$_{11}$, PEG$_{12}$ (PEG 800), PEG$_{28}$ (PEG 1500), and (PEG$_{28}$)$_2$ (PEG 1500×2). In particular embodiments, the first PEG moiety and the second PEG moiety in each of the plurality of conjugates are the same. In preferred embodiments, the first PEG moiety and the second PEG moiety in each of the plurality of conjugates are both PEG$_{28}$ (PEG 1500).

In some embodiments, the present invention provides multimeric peptide conjugates wherein a plurality of the conjugates are linked to each other. In particular embodiments, the multimeric conjugate is a dimer or a tetramer of the plurality of conjugates. In certain embodiments, the multimeric peptide conjugates are formed via linkage between the second PEG moiety of each conjugate. In some instances, the conjugates are linked to each other at the second PEG moiety via at least one lysine residue (e.g., at least 1, 2, 3, 4, 5, or more lysine (K) residues). In other instances, one or more of the lysine residues comprises an imaging or therapeutic agent such as a radionuclide (e.g., for use as a radiolabel) attached thereto. In other embodiments, the composition further comprises a pharmaceutical carrier or excipient.

In yet another aspect, the present invention provides a kit for imaging or therapy, the kit comprising:
  (a) a bi-terminal PEGylated peptide conjugate described herein or a composition thereof (e.g., a plurality or multimer of conjugates); and
  (b) directions for use of the conjugate or the composition in imaging or therapy.

In a further aspect, the present invention provides a method for the in vivo imaging of a target tissue, the method comprising:
  (a) administering to a subject in need of such imaging, a bi-terminal PEGylated peptide conjugate described herein or a composition thereof (e.g., a plurality or multimer of conjugates), wherein an imaging agent is covalently attached to the peptide, the first PEG moiety, or the second PEG moiety; and
  (b) detecting the conjugate to determine where the conjugate is concentrated in the subject.

In some embodiments, the target tissue is a cancerous tissue or an organ. Non-limiting examples of cancerous tissues include cancerous tissues or tumors associated with pancreatic cancer, breast cancer, colorectal cancer, prostate cancer, cervical cancer, and oral squamous cell carcinoma. In preferred embodiments, the peptide conjugate is administered for imaging a tumor such as a pancreatic tumor. Examples of pancreatic tumors suitable for imaging in accordance with the present invention include, but are not limited to, adenocarcinomas, serous cystadenomas, acinar cell cancers, pancreatic neuroendocrine tumors (e.g., insulinomas), and the like.

In certain instances, the imaging agent comprises a radionuclide (e.g., bound to a prosthetic group such as a benzoyl group or a chelating agent), biotin, a fluorophore, a fluorescent protein, horseradish peroxidase, or alkaline phosphatase. In instances where a radionuclide comprises the imaging agent, detection occurs when radiation from the radionuclide is used to determine where the peptide conjugate is concentrated in the subject. In instances where a fluorophore or fluorescent protein comprises the imaging agent, detection occurs when fluorescence from the fluorophore or fluorescent protein is used to determine where the peptide conjugate is concentrated in the subject.

In other embodiments, the peptide conjugate is detected by Magnetic Resonance Imaging (MM), Magnetic Resonance Spectroscopy (MRS), Single Photon Emission Computerized Tomography (SPECT), Positron Emission Tomography (PET), or optical imaging. In yet other embodiments, the conjugate is detected for the diagnosis or prognosis of a disease or disorder mediated by the integrin. In certain embodiments, the disease or disorder is associated with the expression, overexpression, and/or activation of the integrin. In preferred embodiments, the disease or disorder is an $\alpha_v\beta_6$ integrin-mediated disease or disorder, e.g., the peptide conjugate is detected for the diagnosis or prognosis of an $\alpha_v\beta_6$-mediated disease or disorder.

In a related aspect, the present invention provides a method for treating an integrin-mediated disease or disorder in a subject in need thereof, the method comprising:
administering to the subject a therapeutically effective amount of a bi-terminal PEGylated peptide conjugate described herein or a composition thereof (e.g., a plurality or multimer of conjugates), wherein a therapeutic agent is covalently attached to the peptide, the first PEG moiety, or the second PEG moiety.

In certain embodiments, the disease or disorder is associated with the expression, overexpression, and/or activation of the integrin. Non-limiting examples of integrin-mediated diseases or disorders include cancer, inflammatory diseases, autoimmune diseases, chronic fibrosis, chronic obstructive pulmonary disease (COPD), lung emphysema, and chronic wounding skin disease. In particular embodiments, the disease or disorder is an $\alpha_v\beta_6$ integrin-mediated disease or disorder. In some instances, the $\alpha_v\beta_6$ integrin-mediated disease or disorder is pancreatic cancer, breast cancer, colorectal cancer, prostate cancer, cervical cancer, or oral squamous cell carcinoma. In other embodiments, a therapeutically effective amount of the conjugate or the composition is an amount sufficient for achieving a therapeutic benefit in the subject. In yet other embodiments, a therapeutically effective amount of the conjugate or the composition is an amount sufficient to target delivery of the therapeutic agent to a cell expressing the integrin.

In an additional aspect, the present invention provides a method for imaging epithelial cells expressing or overexpressing an integrin of interest (e.g., $\alpha_v\beta_6$ integrin) in the body of a subject, the method comprising administering to the subject a therapeutically effective amount of a peptide conjugate or composition as described herein. The method is particularly useful for the imaging of chronic fibrosis, chronic obstructive pulmonary disease (COPD), lung emphysema, chronic wounding skin disease (e.g., epidermolysis bullosa), or epithelial tumor cells. For example, the method of imaging $\alpha_v\beta_6$-overexpressing epithelial cells may include linking the peptide or one of the PEG components of the conjugate to a fluorescent probe, and incorporating the resulting peptide conjugate into a suitable dosage form such that upon administration the $\alpha_v\beta_6$ integrin-binding conjugate may be visualized by its fluorescent tag.

In a further aspect, the present invention provides a method for delivering a therapeutic agent to a cell expressing or overexpressing an integrin of interest (e.g., $\alpha_v\beta_6$ integrin), or to a tumor, organ, or tissue containing cells expressing or overexpressing an integrin of interest (e.g., $\alpha_v\beta_6$ integrin) in a subject, the method comprising administering a peptide conjugate or composition comprising the therapeutic agent as described herein to the subject.

A. Integrin-Binding Peptides

In certain aspects, the present invention provides bi-terminal PEGylated integrin-binding peptide conjugates. The integrins are a superfamily of cell adhesion receptors that bind to extracellular matrix ligands, cell-surface ligands, and soluble ligands. Integrins are transmembrane $\alpha\beta$ heterodimers and at least 18 $\alpha$ and eight $\beta$ subunits are known in humans, generating 24 heterodimers. The $\alpha$ and $\beta$ subunits have distinct domain structures, with extracellular domains from each subunit contributing to the ligand-binding site of the heterodimer. Non-limiting examples of integrins include $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_8\beta_1$, $\alpha_9\beta_1$, $\alpha_{10}\beta_1$, $\alpha_{11}\beta_1$, $\alpha_v\beta_1$, $\alpha_v\beta_3$, $\alpha_v\beta_5$, $\alpha_v\beta_6$, $\alpha_v\beta_8$, $\alpha_{IIb}\beta_3$, $\alpha_4\beta_7$, $\alpha_E\beta_7$, $\alpha_6\beta_4$, $\alpha_L\beta_2$, $\alpha_M\beta_2$, $\alpha_X\beta_2$, $\alpha_D\beta_2$, and combinations thereof. In some embodiments, the integrin is $\alpha_v\beta_3$ integrin, $\alpha_{IIb}\beta_3$ integrin, or $\alpha_v\beta_6$ integrin. In other embodiments, the integrin-binding peptide comprises an amino acid sequence selected from the group consisting of RGD, LDV, and GFOGER (SEQ ID NO: 1), wherein O is hydroxyproline.

In particular embodiments, the peptide binds to (e.g., targets) $\alpha_v\beta_6$ integrin. In certain instances, the $\alpha_v\beta_6$ integrin-binding peptide comprises the amino acid sequence RGDLX$_1$X$_2$X$_3$ (SEQ ID NO: 2), wherein X$_1$ and X$_2$ are independently selected amino acids and X$_3$ is Leu (L) or Ile (I). In certain instances, X$_1$ is Q, X$_2$ is V, and X$_3$ is L. Unless specified otherwise, amino acid positions herein are numbered from the amino-terminus to the carboxyl-terminus of the peptide.

In some embodiments, the residues LX$_1$X$_2$X$_3$ (SEQ ID NO:8) are present within an $\alpha$-helix. An $\alpha$-helix is understood to be a sequential group of amino acids in a peptide that interact with a particular hydrogen bonding pattern and thus define a helical structure. For example, the hydrogen bonding pattern in a standard $\alpha$-helix is between the carbonyl oxygen of residue n and the amide hydrogen of residue n+4. For a 3$_{10}$-helix, this hydrogen bonding pattern is between residues n and n+3. For a pi-helix, this hydrogen bonding pattern is between residues n and n+5. The number of residues per turn in each $\alpha$-helix is 3.6, 3.0, and 4.4 for the standard $\alpha$-helix, 3$_{10}$-helix, and pi-helix, respectively. In one embodiment, the $\alpha$-helix of the peptide enables the hydrophobic side-chains of the residues LX$_1$X$_2$L/I (SEQ ID NO:8) to protrude from one side of the helix. In another embodiment, the $\alpha$-helix has at least one turn. An $\alpha$-helix useful in the present invention may be an $\alpha$-helix mimetic as described in, e.g., PCT Publication No. WO 95/00534. $\alpha$-helix mimetics are $\alpha$-helical structures which are able to stabilize the structure of a naturally-occurring or synthetic peptide.

The $\alpha_v\beta_6$ integrin-binding peptides used in the conjugates of the present invention may comprise standard helices, 3$_{10}$-helices, pi-helices, or any combination thereof. For example, the helices may comprise amino acids that form a "cap" structure, such as an amino-terminal cap and/or a carboxyl-terminal cap which flank the helix.

In other embodiments, the $\alpha_v\beta_6$ integrin-binding peptide comprises the sequence RGDLX$_1$X$_2$LX$_4$X$_5$X$_6$ (SEQ ID NO:7), wherein X$_1$, X$_2$, X$_4$, X$_5$, and X$_6$ are independently selected amino acids. In certain instances, X$_1$, X$_2$, X$_4$, X$_5$, and X$_6$ are helix-promoting residues. For example, the helix-promoting residues can be independently selected from the group consisting of Glu, Ala, Leu, Met, Gln, Lys, Arg, Val, Ile, His, Thr, Trp, Phe, and Asp. The helix-promoting residues can comprise naturally-occurring amino acids or unnatural amino acids such as artificial or modified amino acids. In some embodiments, the peptide comprises the sequence RGDLX$_1$X$_2$LX$_4$X$_5$X$_6$Z$_n$ (SEQ ID NO:9), wherein Z is a helix-promoting residue and n is any number between 1 and 20. Preferably, n is between 5 and 15 or between 8 and 12. Extension of the helix to include helical residues in the Z position can further increase the helix dipole and provide enhanced binding to $\alpha_v\beta_6$ integrin.

In further embodiments, the $\alpha_v\beta_6$ integrin-binding peptide may be represented by the formula: B$_m$RGDLX$_1$X$_2$LX$_4$X$_5$X$_6$Z$_n$ (SEQ ID NO:10), wherein B is m amino acids which enhances the hydrophobic interactions with the helix defined from LX$_1$X$_2$L (SEQ ID NO:8) and also enhances the RGD domain for binding, Z is a helix-promoting residue, n is a number between 1 and 35, and m is a number between 1 and 35. Preferably, m is selected so that B is sufficiently long to facilitate a hydrophobic/non-covalent interacting core. The exact nature of these residues depends on the general design of the region. In particular, it is preferred to have a mixture of hydrophobic interactions (from residues such as Val, Ile, Leu) and/or electrostatic interactions (using Asp, Glu, Lys, and/or Arg together with their counterpart ion-pair at X$_1$ and/or X$_2$).

In particular embodiments, the $\alpha_v\beta_6$ integrin-binding peptide comprises the amino acid sequence RGDLX$_1$X$_2$X$_3$AQX$_6$ (SEQ ID NO: 3), wherein X$_6$ is Lys (K) or Arg (R). In preferred embodiments, X$_6$ is R.

In certain embodiments, the $\alpha_v\beta_6$ integrin-binding peptide comprises or consists of an amino acid sequence selected from NAVPNLRGDLQVLAQKVART (A20FMDV2; SEQ ID NO:5), NAVPNLRGDLQVLAQRVART (A20FMDV2 K16R; SEQ ID NO:5), GFTTGRRGDLATIHGMNRPF (A20LAP; SEQ ID NO:11), YTASARGDLAHL-TTTHARHL (A20FMDV1; SEQ ID NO:12), and combinations thereof.

In other embodiments, the $\alpha_v\beta_6$ integrin-binding peptide comprises the amino acid sequence RSDLTPLFX$_7$ (SEQ ID NO: 4), wherein X$_7$ is absent or is any amino acid. In certain instances, X$_7$ is absent (i.e., the peptide comprises or consists of the amino acid sequence RSDLTPLF (SEQ ID NO: 4)). In certain other instances, X$_7$ is K (i.e., the peptide comprises or consists of the amino acid sequence RSDLTPLFK (SEQ ID NO: 4)).

The $\alpha_v\beta_6$ integrin, which is a receptor for fibronectin, tenascin, vitronectin, the latency associated peptide (LAP) of TGF-β, and viral capsid protein (VP1) of foot-and-mouth disease virus (FMDV), is expressed at very low or undetectable levels in only a subset of epithelial cells in normal adult tissues (Breuss et al., *J. Cell Sci.,* 108:2241-2251 (1995)). However, $\alpha_v\beta_6$ integrin expression is increased dramatically during development, following injury or inflammation, or in a variety of epithelial neoplasms. For example, keratinocytes show de novo expression of $\alpha_v\beta_6$ integrin in both oral and skin wounds (Breuss et al., supra; Clark et al., *Am. J. Path.,* 148:1407-1421 (1996)). In addition, $\alpha_v\beta_6$ integrin plays an active role in tumor invasion because its expression is often higher at the invasive margins of oral squamous cell carcinomas. As a result, $\alpha_v\beta_6$ integrin is an excellent target for both imaging and therapy of diseases or disorders such as pancreatic cancer, oral cancer, ovarian cancer, breast cancer, and colon cancer. Therefore, bi-terminal PEGylation of $\alpha_v\beta_6$ integrin-binding peptides with small, monodisperse PEG molecules having a defined chain length (e.g., PEG$_{28}$) can be used to generate conjugates of the present invention that display significantly better localizing and/or targeting potential by providing high tumor selectivity and specificity for $\alpha_v\beta_6$-expressing tumors and having increased metabolic stability and retention at the tumor site when compared to peptides having individual N- or C-terminal PEGylation.

In some embodiments, the peptide is a bivalent peptide that binds to the integrin and a receptor that is co-expressed with the integrin. Non-limiting examples of co-expressed receptors include CXCR4. In particular embodiments, the bivalent peptide binds to both $\alpha_v\beta_6$ integrin and CXCR4. In other embodiments, the receptor that is co-expressed with the integrin is another integrin, e.g., $\alpha_v\beta_3$ integrin co-expressed with $\alpha_v\beta_5$ integrin. In particular embodiments, the bivalent peptide binds to both $\alpha_v\beta_3$ integrin and $\alpha_v\beta_5$ integrin. In certain instances, the peptide comprises a first peptide fragment that binds to an integrin linked to a second peptide fragment that binds to a co-expressed receptor. In other instances, the peptide comprises a first peptide fragment that binds to a co-expressed receptor linked to a second peptide fragment that binds to an integrin. The first and second peptide fragments can be linked directly to each other or can be linked via a glycine linker or other suitable linker known in the art. In some instances, the first peptide fragment is PEGylated at the N-terminus and the second peptide fragment is PEGylated at the C-terminus, thereby forming a bi-terminal PEGylated bivalent peptide conjugate of the invention.

In other embodiments, the peptide of the invention is between about 5 to about 45 amino acids in length, between about 8 to about 45 amino acids in length, between about 8 to about 25 amino acids in length, between about 12 to about 45 amino acids in length, between about 5 to about 40 amino acids in length, between about 10 to about 40 amino acids in length, or about 35, 30, 25, 20, 15, or 10 amino acids in length. For example, the peptide may be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more amino acids in length. Typically, the peptide should not exceed a length which would allow the formation of a tertiary structure, such as, for example, greater than 45 amino acids if present as an isolated molecule. However, the peptide may exceed 45 amino acids if fused to a larger molecule such as an antibody or another protein or macromolecule which could prevent the formation of a tertiary structure within the peptide. The peptide may also exceed 45 amino acids if it is a bivalent peptide having first and second peptide fragments that bind to different receptors. Preferably, the peptide is about 20 amino acids in length.

The peptides used in the conjugates of the invention can also be functional variants of the peptides as defined above, including peptides that possess at least about 50%, 55%, 60%, 65%, 70%, 75%, 80%, 85%, 90%, 95%, or more sequence identity with the peptides described above. In certain instances, the peptides can comprise naturally-occurring amino acids and/or unnatural amino acids. Examples of unnatural amino acids include, but are not limited to, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of naturally-occurring amino acids (e.g., trifluorotyrosine, p-Cl-phenylalanine, p-Br-phenylalanine, p-I-phenylalanine, etc.), L-allylglycine, b-alanine, L-a-amino butyric acid, L-g-amino butyric acid, L-a-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline, methyl derivatives of phenylalanine (e.g., 1-methyl-Phe, pentamethyl-Phe, L-Phe (4-amino), L-Tyr (methyl), L-Phe(4-isopropyl), L-Tic (1,2,3,4-tetrahydroisoquinoline-3-carboxyl acid), L-diaminopropionic acid, L-Phe (4-benzyl), etc.). The peptides may be further modified. For example, one or more amide bonds may be replaced by ester or alkyl backbone bonds. There may be N- or C-alkyl substituents, side-chain modifications, or constraints such as disulfide bridges or side-chain amide or ester linkages.

The peptides used in the conjugates of the invention may include both modified peptides and synthetic peptide analogues. Peptides may be modified to improve formulation and storage properties, or to protect labile peptide bonds by incorporating non-peptidic structures. Peptides of the present invention may be prepared using methods known in the art. For example, peptides may be produced by chemical synthesis, e.g., using solid phase techniques and/or automated peptide synthesizers, or by recombinant means. In certain instances, peptides may be synthesized using solid phase strategies on an automated multiple peptide synthesizer (Abimed AMS 422) using 9-fluorenylmethyloxycarbonyl (Fmoc) chemistry. The peptides can then be purified by reversed phase-HPLC and lyophilized. The peptides may alternatively be prepared by cleavage of a longer peptide or full-length protein sequence. For example, a fragment containing the $\alpha_v\beta_6$ integrin-binding domain of fibronectin, tenascin, vitronectin, the latency associated peptide (LAP) of TGF-β, or viral capsid protein (VP1) of foot-and-mouth disease virus (FMDV) can be isolated by cleavage of the full-length protein.

In other embodiments, the peptide component of the conjugates of the invention may be cyclized. Methods are well known in the art for introducing cyclic structures into peptides to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclization methods include the formation of thioethers and carboxyl- and amino-terminal amides and esters. A number of synthetic techniques have been developed to generate synthetic circular peptides (see, e.g., Tarn et al., Protein Sci., 7:1583-1592 (1998); Romanovskis et al., J. Pept. Res., 52: 356-374 (1998); Camarero et al., J. Amer. Chem. Soc., 121: 5597-5598 (1999); Valero et al., J. Pept. Res., 53(1): 56-67 (1999)). Generally, the role of cyclizing peptides is two fold: (1) to reduce hydrolysis in vivo; and (2) to thermodynamically destabilize the unfolded state and promote secondary structure formation.

IV. Methods of Administration

The bi-terminal PEGylated integrin-binding peptide conjugates of the present invention have particular utility in human and veterinary imaging, therapeutic, prognostic, and diagnostic applications. For example, the conjugates can be used for imaging tumors such as malignant tumors of the pancreas (e.g., adenocarcinomas, serous cystadenomas, acinar cell cancers, pancreatic neuroendocrine tumors such as insulinomas, etc.) or any other tissue or organ. The conjugates are also useful for treating diseases and disorders such as cancer (e.g., pancreatic cancer, breast cancer, colon cancer, cervical cancer, lung cancer, etc.), inflammatory disease, autoimmune disease, chronic fibrosis, chronic obstructive pulmonary disease (COPD), lung emphysema, and chronic wounding skin disease.

Administration of the peptide conjugates of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra-joint, parenteral, intra-arteriole, intradermal, intraventricular, intracranial, intraperitoneal, intralesional, intranasal, rectal, vaginal, or by inhalation. Moreover, where injection is to treat a tumor, administration may be directly to the tumor and/or into tissues surrounding the tumor.

The compositions containing a conjugate or a combination of conjugates of the present invention may be administered repeatedly, e.g., at least 2, 3, 4, 5, 6, 7, 8, or more times, or the composition may be administered by continuous infusion. Suitable sites of administration include, but are not limited to, dermal, mucosal, bronchial, gastrointestinal, anal, vaginal, eye, and ear. The formulations may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a conjugate or a combination of conjugates.

Methods for preparing such dosage forms are known to those skilled in the art (see, for example, REMINGTON'S PHARMACEUTICAL SCIENCES, 18TH ED., Mack Publishing Co., Easton, Pa. (1990)). The composition to be administered contains a quantity of the conjugate or combination of conjugates in a pharmaceutically effective amount for imaging a tumor, organ, or tissue or for relief of a condition being treated, when administered in accordance with the teachings of this invention. In addition, pharmaceutically acceptable salts of the conjugates of the present invention (e.g., acid addition salts) may be prepared and included in the compositions using standard procedures known to those skilled in the art of synthetic organic chemistry and described, e.g., by March, Advanced Organic Chemistry: Reactions, Mechanisms and Structure, 4th Ed., New York, Wiley-Interscience (1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, about 0.1% to about 75%, about 0.1% to 50%, or about 0.1% to 10% by weight of a conjugate of the present invention or a combination thereof, with the remainder consisting of suitable pharmaceutical carrier and/or excipients. Appropriate excipients can be tailored to the particular composition and route of administration by methods well known in the art. See, e.g., REMINGTON'S PHARMACEUTICAL SCIENCES, supra.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The compositions can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; coloring agents; and flavoring agents. The compositions may also comprise biodegradable polymer beads, dextran, and cyclodextrin inclusion complexes.

For oral administration, the compositions can be in the form of tablets, lozenges, capsules, emulsions, suspensions, solutions, syrups, sprays, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the conjugate or combination of conjugates, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The conjugates can also be formulated into a suppository disposed, for example, in a polyethylene glycol (PEG) carrier.

Liquid compositions can be prepared by dissolving or dispersing a conjugate or a combination of conjugates and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The conjugates of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the conjugate to the appropriate site or sites. However, one of ordinary skill in the art understands that the dose administered will vary depending on a number of factors, including, but not limited to, the particular conjugate or set of conjugates to be administered, the mode of administration, the type of application (e.g., imaging, diagnostic, prognostic, therapeutic, etc.), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased metabolic stability, tumor retention, and tumor to blood ratios associated with the conjugates of the present invention permits a wider margin of safety for dosage concentrations and for repeated dosing.

V. Therapeutic Applications

In certain aspects, the bi-terminal PEGylated integrin-binding peptide conjugates of the present invention are used for the treatment of an integrin-mediated disease or disorder in a subject in need thereof. Examples of diseases or disorders suitable for treatment with the peptide conjugates described herein include, but are not limited to, allergy, anxiety disorder, autoimmune disease, behavioral disorder, birth defect, blood disorder, bone disease, cancer, chronic fibrosis, chronic obstructive pulmonary disease (COPD), chronic wounding skin disease, circulatory disease, tooth disease, depressive disorder, dissociative disorder, ear condition, eating disorder, eye condition, food allergy, food-borne illness, gastrointestinal disease, genetic disorder, heart disease, hormonal disorder, immune deficiency, infectious disease, inflammatory disease, insect-transmitted disease, nutritional disorder, kidney disease, leukodystrophy, liver disease, king emphysema, mental health disorder, metabolic disease, mood disorder, musculodegenerative disorder, neurological disorder, neurodegenerative disorder, neuromuscular disorder, personality disorder, phobia, pregnancy complication, prion disease, prostate disease, psychological disorder, psychiatric disorder, respiratory disease, sexual disorder, skin condition, sleep disorder, speech-language disorder, sports injury, tropical disease, vestibular disorder, and wasting disease. Preferably, the $\alpha_v\beta_6$-mediated disease or disorder is cancer, an inflammatory disease, an autoimmune disease, chronic fibrosis, chronic obstructive pulmonary disease (COPD), lung emphysema, and chronic wounding skin disease (e.g., epidermolysis bullosa).

Cancer generally includes any of various malignant neoplasms characterized by the proliferation of anaplastic cells that tend to invade surrounding tissue and metastasize to new body sites. Non-limiting examples of different types of cancer suitable for treatment using the conjugates or compositions of the present invention include ovarian cancer, breast cancer, lung cancer, bladder cancer, thyroid cancer, liver cancer, pleural cancer, pancreatic cancer, cervical cancer, prostate cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

One skilled in the art will also appreciate that the conjugates of the present invention can be co-administered with other therapeutic agents for the treatment of cancer. Suitable anti-cancer agents for combination therapy include, without limitation, cytotoxins and agents such as antimetabolites, alkylating agents, anthracyclines, antibiotics, antimitotic agents, procarbazine, hydroxyurea, asparaginase, corticosteroids, interferons, radiopharmaceuticals, peptides with anti-tumor activity such as TNF-α, pharmaceutically acceptable salts thereof derivatives thereof, prodrugs thereof, and combinations thereof. For example, a pharmaceutical composition comprising one or more conjugates of the present invention may be administered to a patient before, during, or after administration of an anti-cancer agent or combination of anti-cancer agents either before, during, or after chemotherapy. Treatment with the conjugate after chemotherapy may be particularly useful for reducing and/or preventing recurrence of the tumor or metastasis. In some embodiments, the anti-cancer agent can be covalently linked directly or indirectly (e.g., via liposomes or nanoparticles) to a bi-terminal PEGylated integrin-binding peptide as described herein.

Inflammatory diseases typically include diseases or disorders characterized or caused by inflammation. Inflammation can result from a local response to cellular injury that is marked by capillary dilatation, leukocytic infiltration, redness, heat, and pain that serves as a mechanism initiating the elimination of noxious agents and damaged tissue. The site of inflammation can include, for example, the lungs, the pleura, a tendon, a lymph node or gland, the uvula, the vagina, the brain, the spinal cord, nasal and pharyngeal mucous membranes, a muscle, the skin, bone or bony tissue, a joint, the urinary bladder, the retina, the cervix of the uterus, the canthus, the intestinal tract, the vertebrae, the rectum, the anus, a bursa, a follicle, and the like. Examples of inflammatory diseases suitable for treatment using the conjugates of the present invention include, but are not limited to, inflammatory bowel disease (e.g., Crohn's disease or ulcerative colitis), rheumatoid diseases such as rheumatoid arthritis, fibrositis, pelvic inflammatory disease, acne, psoriasis, actinomycosis, dysentery, biliary cirrhosis, Lyme disease, heat rash, Stevens-Johnson syndrome, mumps, pemphigus vulgaris, and blastomycosis.

Autoimmune diseases generally include diseases or disorders resulting from an immune response against a self-tissue or tissue component such as, e.g., a self-antibody response or cell-mediated response. Examples of autoimmune diseases suitable for treatment using the conjugates of the present invention include, without limitation, organ-specific autoimmune diseases, in which an autoimmune response is directed against a single tissue, such as Type I diabetes mellitus, myasthenia gravis, vitiligo, Graves' disease, Hashimoto's disease, Addison's disease, autoimmune gastritis, and autoimmune hepatitis; and non-organ specific autoimmune diseases, in which an autoimmune response is directed against a component present in several or many organs throughout the body, such as systemic lupus erythematosus, progressive systemic sclerosis and variants, polymyositis, and dermatomyositis. Additional autoimmune diseases include, for example, pernicious anemia, primary biliary cirrhosis, autoimmune thrombocytopenia, Sjögren's syndrome, and multiple sclerosis.

One skilled in the art will appreciate that the conjugates of the present invention can be co-administered with other therapeutic agents for the treatment of inflammatory or autoimmune diseases. Suitable anti-inflammatory agents for combination therapy include, without limitation, corticosteroids, non-steroidal anti-inflammatory agents, antibodies such as infliximab, 5-aminosalicylates, antibiotics, pharmaceutically acceptable salts thereof; derivatives thereof, prodrugs thereof, and combinations thereof. Suitable immunosuppressive agents for combination therapy include, without limitation, azathioprine and metabolites thereof, antimetabolites such as methotrexate, immunosuppressive antibodies, mizoribine monophosphate, cyclosporine, scoparone, FK-506 (tacrolimus), FK-778, rapamycin (sirolimus), glatiramer acetate, mycopehnolate, pharmaceutically acceptable salts thereof, derivatives thereof, prodrugs thereof, and combinations thereof.

In another embodiment, the conjugates of the present invention are useful for treating an infection or infectious disease caused by, e.g., a virus, bacterium, fungus, parasite, or any other infectious agent. Non-limiting examples of infectious diseases suitable for treatment include, but are not limited to, acquired immunodeficiency syndrome (AIDS/HIV) or HIV-related disorders, Alpers syndrome, anthrax, bovine spongiform encephalopathy (mad cow disease), chicken pox, cholera, conjunctivitis, Creutzfeldt-Jakob disease (CJD), dengue fever, Ebola, elephantiasis, encephalitis, fatal familial insomnia, Fifth's disease, Gerstmann-Straussler-Scheinker syndrome, hantavirus, *Helicobacter pylori*, hepatitis (hepatitis A, hepatitis B, hepatitis C), herpes, influenza (e.g., avian influenza A (bird flu)), Kuru, leprosy, lyme disease, malaria, hemorrhagic fever (e.g., Rift Valley fever, Crimean-Congo hemorrhagic fever, Lassa fever, Marburg virus disease, and Ebola hemorrhagic fever), measles, meningitis (viral, bacterial), mononucleosis, nosocomial infections, otitis media, pelvic inflammatory disease (PID), plague, pneumonia, polio, prion disease, rabies, rheumatic fever, roseola, Ross River virus infection, rubella, salmonellosis, septic arthritis, sexually transmitted diseases (STDs), shingles, smallpox, strep throat, tetanus, toxic shock syndrome, toxoplasmosis, trachoma, tuberculosis, tularemia, typhoid fever, valley fever, whooping cough, and yellow fever.

In certain embodiments, the conjugates of the present invention are useful for treating a neurological or musculoskeletal disorder. Examples of such disorders include, but are not limited to, Alzheimer's disease, Aicardi syndrome, amnesia, amyotrophic lateral sclerosis (Lou Gehrig's Disease), anencephaly, aphasia, arachnoiditis, Arnold Chiari malformation, ataxia telangiectasia, Batten disease, Bell's palsy, brachial plexus injury, brain injury, brain tumor, Charcol-Marie-Tooth disease, encephalitis, epilepsy, essential tremor, Guillain-Barre Syndrome, hydrocephalus, hyperhidrosis, Krabbes disease, meningitis, Moebius syndrome, muscular dystrophy, multiple sclerosis, Parkinson's disease, peripheral neuropathy, postural or orthostatic tachycardia syndrome, progressive supranuclear palsy, Reye's syndrome, shingles, Shy-Drager Syndrome, spasmodic torticollis, spina bifida, spinal muscular atrophy, Stiff Man syndrome, synesthesia, syringomyelia, thoracic outlet syndrome, Tourette syndrome, toxoplasmosis, and trigeminal neuralgia.

When used in therapeutic applications, the conjugates of the present invention typically have a therapeutic agent covalently or noncovalently attached to one or more of the peptide or the first or second PEG moiety. In certain instances, the therapeutic agent is cytotoxic. Suitable therapeutic agents provide beneficial, prophylactic, and/or therapeutic properties to a subject and include, but are not limited to, radionuclides, chemotherapeutic agents, nanoparticles, nanodroplets, liposomal drugs, and cytokines. One of skill in the art will be familiar with methods for attaching therapeutic agents to functional groups present on the peptide or PEG moiety. For example, the therapeutic agent can be directly attached to the peptide or PEG portion of the conjugate via covalent attachment of the therapeutic agent to a primary amine group present in the peptide or PEG moiety. One of skill in the art will appreciate that a therapeutic agent can also be bound to the peptide or PEG portion of the conjugate via noncovalent interactions (e.g., ionic bonds, hydrophobic interactions, hydrogen bonds, Van der Waals forces, dipole-dipole bonds, etc.).

In some embodiments, the therapeutic agent is a cytotoxic chemotherapeutic agent. Cytotoxic chemotherapeutic agents are well known in the art and include anti-cancer agents such as alkylating agents (e.g., nitrogen mustards such as mechlorethamine (HN2), cyclophosphamide, ifosfamide, melphalan (L-sarcolysin), and chlorambucil), ethylenimines and methylmelamines (e.g., hexamethylmelamine, thiotepa, alkyl sulphonates such as busulfan, nitrosoureas such as carmustine (BCNU), lomustine (CCNLJ), semustine (methyl-CCN-U), and streptozoein (streptozotocin), and triazenes such as decarbazine (DTIC; dimethyltriazenoimidazolecarboxamide)), antimetabolites (e.g., folic acid analogues such as methotrexate (amethopterin), pyrimidine analogues such as fluorouracil (5-fluorouracil; 5-FU), floxuridine (fluorodeoxyuridine; FUdR), and cytarabine (cytosine arabinoside), and purine analogues and related inhibitors such as mercaptopurine (6-mercaptopurine; 6-MP), thioguanine (6-thioguanine; 6-TG), and pentostatin (2'-deoxycofonnycin)), natural products (e.g., vinca alkaloids such as vinblastine (VLB) and vincristine, epipodophyllotoxins such as etoposide and teniposide, antibiotics such as dactinomycin (actinomycin D), daunorabicin (daunomycin; rubidomycin), doxorubicin, bleomycin, plicamycin (mithramycin), and mitomycin (mitomycin Q), enzymes such as L-asparaginase, and biological response modifiers such as interferon alphenomes), miscellaneous agents (e.g., platinum coordination complexes such as cisplatin (cis-DDP) and carboplatin, anthracenediones such as mitoxantrone and antbracycline, substituted ureas such as hydroxyurea, methyl hydrazine derivatives such as procarbazine (N-methylhydrazine; MIH), adrenocortical suppressants such as mitotane (o,p'-DDD) and aminoglutethimide, paclitaxel (taxol) and analogues/derivatives, and hormone agonists/antagonists such as flutamide and tamoxifen), and combinations thereof.

In other embodiments, one or more of the peptide or the first or second PEG moiety of the conjugate is linked to a particle that contains the therapeutic agent. Particles in this instance include, but are not limited to, nanoparticles and lipid-based vesicles such as liposomes or other similar structures composed of lipids. Liposomes are typically spherical vesicles comprising a phospholipid bilayer that may be used as agents to deliver materials such as drugs or other compounds. Liposomes can be composed of naturally-derived phospholipids with mixed lipid chains (egg phosphatidylethanolamine) or of pure components like dioleolylphosphatidylethanolamine (DOPE). The synthesis and use of liposomes is now well established in the art. Liposomes are generally created by sonication of phospholipids in a suitable medium such as water. Low shear rates create multilamellar liposomes having multi-layered structures. Continued high-shear sonication tends to form smaller unilamellar liposomes. Research has also been able to enable liposomes to avoid detection by the immune system, for example, by coating the lipsomes with polyethylene glycol (PEG). It is also possible to incorporate species in liposomes, such as the peptide conjugates of the present invention, to help to target them to a delivery site, e.g., to cells, tumors, organs, tissues, and the like.

The use of nanoparticles as delivery agents for materials associated with or bound to the nanoparticles is known in the art. Some types of nanoparticles comprise a core, often of metal and/or semiconductor atoms, to which one or more of the peptide or the first or second PEG moiety of the conjugate may be linked (see, e.g., PCT Publication Nos. WO 02/32404, WO 05/10816, and WO 05/116226). Other types of nanoparticles may be formed from materials such as liposomes. In some instances, the nanoparticles may be quantum dots, e.g., nanocrystals of semiconducting materials which have chemical and physical properties that differ markedly from those of the bulk solid (see, e.g., Gleiter, *Adv. Mater.,* 4:474-481 (1992)). Now that their quantum size effects are understood, fundamental and applied research on these systems has become increasingly popular. An interesting application is the use of nanocrystals as luminescent labels for biological systems (see, e.g., Brucher et al., *Science,* 281:2013-2016 (1998); Chan et al., *Science,* 281: 2016-2018 (1998); Mattousi et al., *J. Am. Chem. Soc.,* 122:12142-12150 (2000); and Alivisatos, *Pure Appl. Chem.,* 72:3-9 (2000)). Quantum dots have several advantages over conventional fluorescent dyes. For example, quantum dots emit light at a variety of precise wavelengths depending on their size and have long luminescent lifetimes.

In further embodiments, the therapeutic agent is a cytotoxic peptide or polypeptide capable of promoting cell death. Cytotoxic peptides and polypeptides are well known in the art and include, for example, ricin, abrin, *Pseudomonas* exotoxin, tissue factor, and the like. The use of ricin as a cytotoxic agent is described in Burrows et al., *P.N.A.S. USA,* 90:8996-9000 (1993). The use of tissue factor, which leads to localized blood clotting and infarction of a tumor, is described in Ran et al., *Cancer Res.,* 58:4646-4653 (1998) and Huang et al., *Science,* 275:547-550 (1997). Tsai et al., *Dis. Colon Rectum,* 38:1067-1074 (1995) describes the abrin A chain conjugated to a monoclonal antibody. Other ribosome-inactivating proteins are described as cytotoxic agents in PCT Publication No. WO 96/06641. *Pseudomonas* exotoxin may also be used as the cytotoxic polypeptide (see, e.g., Aiello et al., *P.N.A.S. USA,* 92:10457-10461 (1995)). Certain cytokines, such as TNF-α and IL-2, may also be useful as cytotoxic and/or therapeutic agents.

Certain radioactive atoms may also be cytotoxic if delivered in sufficient doses. Thus, the therapeutic agent may comprise a radioactive atom which, in use, delivers a sufficient quantity of radioactivity to the target site so as to be cytotoxic. Suitable radioactive atoms for use in the peptide conjugates of the present invention include any of the radionuclides described herein, or any other isotope which emits enough energy to destroy a target cell, tumor, organ, or tissue. Preferably, the isotopes and density of radioactive atoms in the conjugate are such that a dose of at least about 4000, 6000, 8000, or 10000 cGy is delivered to the target site and, preferably, to the cells at the target site and their organelles, particularly the nucleus. The radioactive atom may be attached to one or more of the peptide or the first or second PEG moiety of the conjugate in known ways. For example, EDTA or another chelating agent may be attached to the peptide or PEG moiety and used to attach $^{111}$In or $^{90}$Y. In some instances, tyrosine residues present in the peptide may be labeled with $^{125}$I or $^{131}$I. Preferably, a benzoyl group is attached to the peptide or PEG moiety and used to attach $^{18}$F or $^{19}$F. For example, 4-[$^{18}$F]-fluorobenzoic acid or 4-[$^{19}$F]-fluorobenzoic acid can be used to radiolabel the peptide conjugates of the present invention.

VI. Imaging Applications

In certain other aspects, the bi-terminal PEGylated integrin-binding peptide conjugates of the present invention are used as in vivo optical imaging agents (e.g., radiotracers or imaging probes) of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like. In one embodiment, the conjugates of the invention are useful for the detection of the presence of tumors and other abnormalities by monitoring where a particular conjugate is concentrated in a subject. In another embodiment, the conjugates are useful for laser-assisted guided surgery for the detection of micro-metastases of tumors upon laparoscopy. In yet another embodiment, the conjugates are useful in the diagnosis of atherosclerotic plaques and blood clots.

In further embodiments, the conjugates of the present invention are useful in the imaging of: (1) ocular diseases in ophthalmology, e.g., to enhance the visualization of chorioretinal diseases such as vascular disorders, retinopathies, neovascularization, and tumors via direct microscopic imaging; (2) skin diseases such as skin tumors via direct microscopic imaging; (3) gastrointestinal, oral, bronchial, cervical, and urinary diseases and tumors via endoscopy; (4) atherosclerotic plaques and other vascular abnormalities via flexible endoscopic catheters; and (5) pancreatic tumors, breast tumors, brain tumors, perfusion, and stroke via 2D- or 3D-image reconstruction.

The conjugates of the present invention can be administered either systemically or locally to the tumor, organ, or tissue to be imaged, prior to the imaging procedure. Generally, the conjugates are administered in doses effective to achieve the desired optical image of a tumor, tissue, or organ. Such doses may vary widely, depending upon the particular conjugate employed, the tumor, tissue, or organ subjected to the imaging procedure, the imaging equipment being used, and the like.

In some embodiments, the conjugates described herein are used to directly stain or label a sample so that the sample can be identified or quantitated. For instance, a specific conjugate can be added as part of an assay for a biological target analyte (e.g., antigen), as a detectable tracer element in a biological or non-biological fluid, or for other in vitro purposes known to one of skill in the art. Typically, the sample is obtained directly from a liquid source or as a wash from a solid material (organic or inorganic) or a growth medium in which cells have been introduced for culturing, or a buffer solution in which cells have been placed for evaluation. Where the sample comprises cells, the cells are optionally single cells, including microorganisms, or multiple cells associated with other cells in two or three dimensional layers, including multicellular organisms, embryos, tissues, biopsies, filaments, biofilms, and the like.

A detectable response generally refers to a change in, or occurrence of, an optical signal that is detectable either by observation or instrumentally. In certain instances, the detectable response is radioactivity (i.e., radiation), including alpha particles, beta particles, nucleons, electrons, positrons, neutrinos, and gamma rays emitted by a radioactive substance such as a radionuclide. In certain other instances, the detectable response is fluorescence or a change in fluorescence, e.g., a change in fluorescence intensity, fluorescence excitation or emission wavelength distribution, fluorescence lifetime, and/or fluorescence polarization. One of skill in the art will appreciate that the degree and/or location of labeling in a subject or sample can be compared to a standard or control (e.g., healthy tissue or organ).

When used in imaging applications, the conjugates of the present invention typically have an imaging agent covalently or noncovalently attached to one or more of the peptide or the first or second PEG moiety. Suitable imaging agents include, but are not limited to, radionuclides, detectable tags, fluorophores, fluorescent proteins, enzymatic proteins, and the like. One of skill in the art will be familiar with methods for attaching imaging agents to functional groups present on the peptide or PEG moiety. For example, the imaging agent can be directly attached to the peptide or PEG portion of the conjugate via covalent attachment of the imaging agent to a primary amine group present in the peptide or PEG moiety. One of skill in the art will appreciate that an imaging agent can also be bound to the peptide or PEG portion of the conjugate via noncovalent interactions (e.g., ionic bonds, hydrophobic interactions, hydrogen bonds, Van der Waals forces, dipole-dipole bonds, etc.).

In certain instances, the conjugate is radiolabeled with a radionuclide by directly attaching the radionuclide to one or more of the peptide or the first or second PEG moiety of the conjugate. In certain other instances, a benzoyl group labeled with the radionuclide is directly attached to the peptide or PEG portion of the conjugate. For example, 4-[$^{18}$F]-fluorobenzoic acid ("[$^{18}$F]FBA") or 4-[$^{19}$F]-fluorobenzoic acid ("[$^{19}$F]FBA") can be used to radiolabel the conjugates of the present invention. In further instances, the radionuclide is bound to a chelating agent or chelating agent-linker attached to the conjugate. Suitable radionuclides for direct conjugation include, without limitation $^{18}$F, $^{19}$F, $^{124}$I, $^{125}$I, $^{131}$I, and mixtures thereof. Suitable radionuclides for use with a chelating agent include, without limitation, $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At $^{212}$Bi, and mixtures thereof. Suitable chelating agents include, but are not limited to, DOTA, NOTA, NOTA-TCO, BAD, TETA, DTPA, EDTA, NTA, HDTA, their phosphonate analogs, and mixtures thereof. One of skill in the art will be familiar with methods for attaching radionuclides, chelating agents, and chelating agent-linkers to the conjugates of the present invention. In particular, attachment can be conveniently accomplished using, for example, commercially available bifunctional linking groups (generally heterobifunctional linking groups) that can be attached to a functional group present in a non-interfering position on the conjugate and then further linked to a radionuclide, chelating agent, or chelating agent-linker.

Non-limiting examples of fluorophores or fluorescent dyes suitable for use as imaging agents include Alexa Fluor® dyes (Invitrogen Corp.; Carlsbad, Calif.), fluorescein, fluorescein isothiocyanate (FITC), Oregon Green™;

rhodamine, Texas red, tetrarhodamine isothiocynate (TRITC), CyDye™ fluors (e.g., Cy2, Cy3, Cy5), and the like.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al., *Mol. Microbiol.*, 55:1767-1781 (2005), the GFP variant described in Crameri et al., *Nat. Biotechnol.*, 14:315-319 (1996), the cerulean fluorescent proteins described in Rizzo et al., *Nat. Biotechnol.*, 22:445 (2004) and Tsien, *Annu. Rev. Biochem.*, 67:509 (1998), and the yellow fluorescent protein described in Nagal et al., *Nat. Biotechnol.*, 20:87-90 (2002). DsRed variants are described in, e.g., Shaner et al., *Nat. Biotechnol.*, 22:1567-1572 (2004), and include mStrawberry, mCherry, mOrange, mBanana, mHoneydew, and mTangerine. Additional DsRed variants are described in, e.g., Wang et al., *Proc. Natl. Acad. Sci. U.S.A.*, 101:16745-16749 (2004) and include mRaspberry and mPlum. Further examples of DsRed variants include mRFPmars described in Fischer et al., *FEBS Lett.*, 577:227-232 (2004) and mRFPruby described in Fischer et al., *FEBS Lett.*, 580:2495-2502 (2006).

In other embodiments, the imaging agent that is bound to a conjugate of the present invention comprises a detectable tag such as, for example, biotin, avidin, streptavidin, or neutravidin. In further embodiments, the imaging agent comprises an enzymatic protein including, but not limited to, luciferase, chloramphenicol acetyltransferase, β-galactosidase, β-glucuronidase, horseradish peroxidase, xylanase, alkaline phosphatase, and the like.

Any device or method known in the art for detecting the radioactive emissions of radionuclides in a subject is suitable for use in the present invention. For example, methods such as Single Photon Emission Computerized Tomography (SPECT), which detects the radiation from a single photon gamma-emitting radionuclide using a rotating gamma camera, and radionuclide scintigraphy, which obtains an image or series of sequential images of the distribution of a radionuclide in tissues, organs, or body systems using a scintillation gamma camera, may be used for detecting the radiation emitted from a radiolabeled conjugate of the present invention. Positron emission tomography (PET) is another suitable technique for detecting radiation in a subject. Furthermore, U.S. Pat. No. 5,429,133 describes a laparoscopic probe for detecting radiation concentrated in solid tissue tumors. Miniature and flexible radiation detectors intended for medical use are produced by Intra-Medical LLC (Santa Monica, Calif.). Magnetic Resonance Imaging (MRI) or any other imaging technique known to one of skill in the art is also suitable for detecting the radioactive emissions of radionuclides. Regardless of the method or device used, such detection is aimed at determining where the conjugate is concentrated in a subject, with such concentration being an indicator of the location of a tumor or tumor cells.

Non-invasive fluorescence imaging of animals and humans can also provide in vivo diagnostic or prognostic information and be used in a wide variety of clinical specialties. For instance, techniques have been developed over the years for simple ocular observations following UV excitation to sophisticated spectroscopic imaging using advanced equipment (see, e.g., Andersson-Engels et al., *Phys. Med. Biol.*, 42:815-824 (1997)). Specific devices or methods known in the art for the in vivo detection of fluorescence, e.g., from fluorophores or fluorescent proteins, include, but are not limited to, in vivo near-infrared fluorescence (see, e.g., Frangioni, *Curr. Opin. Chem. Biol.*, 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al., *IEEE Transactions on Biomedical Engineering*, 48:1034-1041 (2001)), and the like.

Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, and signal amplification using photomultiplier tubes.

VII. Kits of the Invention

The present invention also provides kits to facilitate and/or standardize the use of the conjugates and compositions described herein, as well as to facilitate the methods described herein. Materials and reagents to carry out these various methods can be provided in kits to facilitate execution of the methods. As used herein, the term "kit" includes a combination of articles that facilitates a process, assay, analysis, or manipulation. In particular, kits comprising the conjugates or compositions of the present invention find utility in a wide range of applications including, for example, immunotherapy and in vivo imaging a cell, tumor, organ, tissue, bioaggregate, biofilm, or the like.

Kits can contain chemical reagents as well as other components. In addition, the kits of the present invention can include, without limitation, instructions to the kit user (e.g., directions for use of the conjugate or composition in immunotherapy, directions for use of the conjugate or composition in imaging a cell, tumor, organ, or tissue, etc.), apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, solutions, buffers or other chemical reagents, suitable samples to be used for standardization, normalization, and/or control samples. Kits of the present invention can also be packaged for convenient storage and safe shipping, for example, in a box having a lid.

VIII. Examples

The following examples are offered to illustrate, but not to limit, the claimed invention.

Example 1. Bi-Terminal PEGylation for Improved Pharmacokinetics and In Vivo Stability of Targeting Peptides This example illustrates that FBA-PEG$_{28}$-A20FMDV2-PEG$_{28}$ (SEQ ID NO:13), a peptide-based molecular imaging probe (conjugate) of the present invention, selectively targets the $\alpha_v\beta_6$ integrin and possesses an advantageous pharmacokinetic profile. The probe is based on a 20-amino acid core termed A20FMDV2, originating from a peptide fragment of the coat protein of the foot-and-mouth-disease virus (Jackson et al., *Virus Res.,* 2003; 91:33-46; Logan et al.,

*Nature*, 1993; 362:566-8), with the amino-acid sequence NAVPNLRGDLQVLAQKVART (SEQ ID NO:5) (using one-letter amino-acid identifiers, written left-to-right from N- to C-terminus). Notably, the peptide has been modified with monodisperse PEG chains (Roberts et al., *Adv. Drug Deliver. Rev.*, 2002; 54:459-76; Knop et al., *Angewandte Chemie.*, 2010; 49:6288-308), that is, PEG chains with an exactly defined number of ethylene glycol repeating units 'n', at the N- and at the C-terminus for improved $\alpha_v\beta_6$-targeted tumor uptake and pharmacokinetics. The imaging probe also carries a fluorine-18-bearing fluorobenzoic acid ($^{18}$F FBA) prosthetic group for detection by gamma-probes or inside a positron emission tomography (PET) scanner.

Introduction

Integrins are a group heterodimeric bi-directional transmembrane cell surface receptors (Hynes, *Cell*, 2002; 110: 673-87). While most integrins are essential for proper biological function, some of them are highly localized and significantly up-regulated only in diseased tissue. Among those, the integrin $\alpha_v\beta_6$, alpha(v)beta(6), has been recognized as an important marker during tumorgenesis (Bandyopadhyay et al., *Current drug targets*, 2009; 10:645-52) and has even been identified as a prognostic indicator correlating with the severity of disease for challenging malignancies such as lung cancer (Elayadi et al., *Cancer Res.*, 2007; 67:5889-95), colorectal cancer (Bates, *Cell Cycle*, 2005; 4:1350-2), cervical cancer (Hazelbag et al., *J Pathol.*, 2007; 212:316-24), and gastric cancer (Zhang et al., *Clin Oncol-UK*, 2008; 20:61-6).

Therefore, reliable in vivo localization and quantification of $\alpha_v\beta_6$ expression levels could make significant contributions to proper detection, characterization, and (personalized) management of disease. It would also provide information on the homogeneity (or heterogeneity) of the malignancy, and aid in the detection of distant disease (metastases) susceptible to $\alpha_v\beta_6$-targeted therapy. To achieve this, a molecular probe that selectively targets the integrin $\alpha_v\beta_6$ on the cellular level is required.

We have previously shown that the A20FMDV2 peptide, (radio)labeled with positron-emitting radioisotope prosthetic groups for detection by gamma-probes or inside a positron emission tomography (PET) scanner, can successfully detect the integrin $\alpha_v\beta_6$ in vitro and in vivo (Hausner et al., *Cancer Res.*, 2007; 67:7833-40). Although this probe, $^{18}$F FBA-A20FMDV2 (SEQ ID NO:14), rapidly cleared from non-target tissue and was excreted via the preferential renal pathway in the urine, it did, however, still have some pharmacokinetic shortcomings, notably a very rapid clearing from the blood stream, low stability, and washout from the target tumor tissue when evaluated in a mouse model with $\alpha_v\beta_6$-expressing pancreatic cancer BxPC-3 xenografts (Hausner et al., supra; Hausner et al., *Cancer Res.*, 2009; 69:5843-50).

Addition of moderately-sized poly(ethylene glycol) (PEG) to the N-terminus of the peptide appreciably improved uptake in the tumor and affected pharmacokinetics. Notably, the addition of a single PEG$_{28}$ unit increased tumor uptake from <1% ID/g to nearly 2% ID/g and eliminated washout from the tumor, resulting in a greatly improved signal/background ratio, especially at later time points. However, this probe, $^{18}$F FBA-PEG$_{28}$-A20FMDV2 (SEQ ID NO:15), also showed increased initial uptake in the kidneys, but did wash out at later time points. The addition of a second PEG$_{28}$ unit to the N-terminus did not result in a significant further increase of uptake in the tumor. In fact, that addition of the second PEG unit was disadvantageous, because the probe, $^{18}$F FBA-(PEG$_{28}$)$_2$-A20FMDV2 (SEQ ID NO:16), was also trapped in the kidneys at high levels (40% ID/g) and did not show any release. Likewise, shifting of the PEG unit to the C-terminus only had marginal effects. While the probe, FBA-A20FMDV2-PEG$_{28}$ (SEQ ID NO:17), displayed some initial tumor uptake >1% ID/g, it also washed out, thus not resulting in improved signal/background ratios over time.

In addition, all of these probes displayed rapid in vivo metabolism. For example, when evaluating urine samples it was determined that, while the introduction of PEG to the N-terminus reduced the number of major radiometabolites in the animal model from three (without PEG) to one (with PEG), no intact probe was found in either case. When the PEG was at the C-terminus, three metabolites and no intact probe were found.

Results

Contrary to probes bearing a PEG group at the N-terminus or a PEG group at the C-terminus, the bi-terminally PEGylated probes of the present invention, such as, e.g., FBA-PEG$_{28}$-A20FMDV2-PEG$_{28}$ (SEQ ID NO:13), bears one PEG at the N-terminus and one PEG at the C-terminus, resulting in a greatly improved pharmacokinetic profile. Key features include high tumor uptake and retention, as well as high metabolic stability. Compared to other strategies (e.g., cyclization, use of unnatural amino acids) (Kimura et al., *Clin Cancer Res.*, 2012; 18:839-49; Briand et al., *Proc Natl Acad Sci USA*, 1997; 94:12545-50; Fletcher et al., *Chem Rev.*, 1998; 98:763-95; Fischer, *Curr Protein Pept Sc.*, 2003; 4:339-56), we surprisingly discovered that PEGylation of targeting peptides according to the present invention is an experimentally simple and straightforward way of achieving unexpectedly high target affinity, selectivity, tumor uptake and retention, as well as high metabolic stability and superior clearance from the kidneys.

In a mouse model, we found a high tumor uptake of 4.7% ID/g (1 h) with good retention (3.4% ID/g at 4 h) for BxPC-3 xenografts. These uptake values are markedly higher than observed for any of the other probes, and they were obtained on very small BxPC-3 xenograft tumors ranging from 20-80 mg. These results enable the visualization of oftentimes difficult-to-detect small, early lesions.

Furthermore, the bi-terminal PEGylation resulted in greatly improved metabolic stability. Over two-thirds of the probe remained intact in the urine at 1 h (and approx. half remained intact at 4 h). Additional studies on DX3puroB6 and BxPC-3 tumors showed that >80% of the probe remained intact in the tumor at 1 h, and nearly 90% of the probe was recovered intact from the kidneys.

Notably, the observations and results described herein were not predictable based on, and differ significantly from other PEGylation patterns evaluated (e.g., one or two PEG chains at the N-terminus only, one PEG chain at the C-terminus only, no PEGylation), none of which were able to approach or match the superior pharmacokinetic and stability profiles achieved with bi-terminal PEGylation, as exemplified by the probe FBA-PEG$_{28}$-A20FMDV2-PEG$_{28}$ (SEQ ID NO:13).

FIG. 1 shows the structures of the A20FMDV2 PEGylation variations that were evaluated in the studies described herein. FIGS. 2-10A and 10B provide a detailed comparison of key parameters for biodistribution and imaging probe stability of these A20FMDV2 PEGylation variations. Table 1 provides a summary of the select key pharmacokinetic and stability data for each PEG-modified A20FMDV2 variant.

TABLE 1

Summary of the biodistribution and stability experimental data for A20FMDV2 PEGylated compounds.

| Animal Model | Tumor xenograft Biodistribution data | Stability data | Metabolite data |
|---|---|---|---|
| (1) 18F-FBA-A20FMDV2 (SEQ ID NO: 14) | | | |
| Mice (nu/nu, ♂) | Dx3puroB6/Dx3puro (paired) 1, 2, 4 h | | Urine |
| Mice (nu/nu, ♂) | BxPC-3/MIA PaCa-2 (paired) 1, 2, 4 h | | |
| (2) 18F-FBA-PEG28-A20FMDV2 (SEQ ID NO: 15) | | | |
| Mice (nu/nu, ♂) | Dx3puroB6/Dx3puro (paired) 1, 2, 4 h | | Urine |
| Mice (nu/nu, ♂) | BxPC-3 1, 2, 4 h | | |
| (3) 18F-FBA-PEG28-PEG28-A20FMDV2 (SEQ ID NO: 16) | | | |
| Mice (nu/nu, ♂) | Dx3puroB6/Dx3puro (paired) 1, 2, 4 h | | Urine |
| Mice (nu/nu, ♂) | BxPC-3 1, 2, 4 h | | |
| (4) 18F-FBA-A20FMDV2-PEG28 (SEQ ID NO: 18) | | | |
| Mice (nu/nu, ♀) | Dx3puroB6/Dx3puro (paired) 1, 2, 4 h | | Urine |
| (5) 18F-FBA-PEG28-A20FMDV2-PEG28 (SEQ ID NO: 19) | | | |
| Mice (nu/nu, ♀) | Dx3puroB6/Dx3puro (paired) 1, 2, 4 h | Serum | Urine, Tumor |
| Mice (nu/nu, ♀) | BxPC-3 1, 2, 4 h; 1 h blocked | | Urine, Tumor, Kidneys |

"PEG28" and "PEG1500" are used synonymously and describe the exact same molecular entity, incorporated into the probe using "Fmoc-amino PEG propionic acid" (molecular weight=1544.8 Da, PolyPure #15137-2790 or Novabiochem #851033) as reagent. "PEG1500" refers to the compound by its approx. molecular weight; "PEG28" refers to the number of ethylene glycol units in the reagent.

Biodistribution data were determined by dissection of animals (generally n≥3/time point or condition) at given time point after conscious uptake, followed by measuring of accumulated activity in a gamma counter, and weighing of the organ. Data are expressed as % of decay-corrected injected dose per gram of tissue (% ID/g).

Stability in PBS and serum was determined ex vivo by incubation of aliquots in given medium, typically at r.t. (PBS) or 37° C. (serum), followed by analysis on radio HPLC. Data are expressed as % probe remaining intact in sample.

Metabolites in urine, kidneys, and tumor were determined in vivo. Tissues/organs were collected from animals at given time points after i.v. injection of the probe, following conscious uptake. Samples were homogenized and extracted as needed and analyzed by radio HPLC. Data are expressed as % probe remaining intact in tissue/organ sample.

Tumor models—DX3puroβ6/DX3puro: Human melanoma cell line. DX3puroβ6 has been stably transfected to express integrin $\alpha_v\beta_6$. DX3puro is negative control cell line. Both express equal levels of other integrins (including $\alpha_v\beta_3$). BxPC-3: Pancreatic cell line with endogenous $\alpha_v\beta_6$-expression. MIA PaCa-2: Pancreatic cell line, no $\alpha_v\beta_6$-expression.

FIG. 2 shows biodistribution data for compound 1 (18F-FBA-A20FMDV2) in DX3puroB6 and Dx3puro tumors. Key observations include fast blood clearance: (1) Renal clearance (Urine very high at 1.2 h (>900% ID/g)), Kidneys comparatively low, and clearing well over time (<6% ID/g @ 1 h, <0.5% ID/g @ 4 h); (2) Minor GI clearance (Gall bladder initially high, then clearing; Stomach low—clearing (<4% ID/g @ 1 h); (3) Lung 1.6% ID/g @ 1 h—dropping to 0.4% ID/g @ 2, 4 h. Tumors were moderate to large size. Tumor size appeared to have minimal, if any effect on % ID/g (largest may be necrotic): POS: 0.88→0.23% ID/g @ 1, 4 h→Moderate, and washing out; NEG: 0.49→0.19% ID/g @ 1, 4 h→Low, and washing out. Moderate POS/NEG ratio, going to near-parity @ 4 h.

FIG. 3 shows biodistribution data for compound 1 (18F-FBA-A20FMDV2) in BxPC-3 (and MIA PaCa-2) tumors. Key observations include fast blood clearance: (1) Renal clearance (Urine high at 1.2 h (>300% ID/g)), Kidneys comparatively low, and clearing well over time (<4% ID/g @ 1 h, <0.2% ID/g @ 4 h); (2) Minor GI clearance (Gall bladder initially high, then clearing; Stomach low—clearing (0.5% ID/g @ 1 h); (3) Lung 0.8% ID/g @ 1 h—dropping to <0.1% ID/g @ 2, 4 h. BxPC-3 tumors were moderate size (MIA PaCa-2 tumors were moderate to large. Tumor size appeared to have minimal, if any effect on % ID/g: POS: 0.69→0.12% ID/g @ 1, 4 h→Moderate, washing out, comparable to Dx3puroB6; NEG: 0.16→0.01% ID/g @ 1, 4 h→Low, washing out quickly. Good POS/NEG ratio, increasing over time, better than Dx3puroB6/Dx3puro pair.

FIG. 4 shows biodistribution data for compound 2 (18F-FBA-PEG28-A20FMDV2) in DX3puroB6 and Dx3puro tumors. Key observations include fast blood clearance: (1) Renal clearance (Urine high at 1 h (~200% ID/g)—clearing); Kidneys comparatively low, and clearing well over time (25% ID/g→2.7% ID/g @ 1 h, 4 h); (2) Essentially no GI clearance (Gall bladder <3% ID/g; Liver <0.1% ID/g Stomach low—clearing (7% ID/g→1.8% ID/g @ 1 h, 4 h); (3) Lung 2.0% ID/g @ 1 h—dropping to 1.4% ID/g @ 4 h. Tumors were moderate to large size. Tumor size appeared to have minimal, if any effect on % ID/g (largest may be necrotic): POS: 0.49→0.49% ID/g @ 1, 4 h→Steady, no wash out; NEG: 0.11→0.07% ID/g @ 1, 4 h→Low, and washing out. Good POS/NEG ratio, increasing for later time points, highest at 2 h.

FIG. 5 shows biodistribution data for compound 2 (18F-FBA-PEG28-A20FMDV2) in BxPC-3 tumors. Key observations include fast blood clearance: (1) Renal clearance (Urine high at 1 h (~400% ID/g)—clearing); Kidneys comparatively low, and clearing well over time (19% ID/g→3.3% ID/g @ 1 h, 4 h); (2) Essentially no GI clearance (Gall bladder <4% ID/g; Liver <0.2% ID/g Stomach low—clearing (2.6% ID/g→1.9% ID/g @ 1 h, 4 h); (3) Lung 2.1% ID/g @ 1 h—dropping to 1.7% ID/g @ 4 h. Tumors were moderate size. Tumor size appeared to have minimal, if any effect on % ID/g. Uptake: 1.9→1.5% ID/g @ 1, 4 h→Drop after 1 h, then steady; Higher uptake than Dx3puroB6.

FIG. 6 shows biodistribution data for compound 3 (18F-FBA-PEG28-PEG28-A20FMDV2) in DX3puroB6 and Dx3puro tumors. Key observations include fast blood clearance: (1) Renal clearance (Urine moderate at 1 h (~60% ID/g)—clearing); Kidneys high—NOT clearing (41% ID/g→46% ID/g @ 1 h, 4 h); (2) Minor GI clearance (Gall bladder <3% ID/g; Liver <0.1% ID/g Stomach moderate—steady (5.5% ID/g→5.5% ID/g @ 1 h, 4 h); (3) Lung 1.1→1.3% ID/g @ 1 h, 4 h. Tumors were moderate to large size. Tumor size appeared to have minimal, if any effect on % ID/g (largest may be necrotic): POS: 0.52→0.54% ID/g @ 1, 4 h→Steady, no wash out; NEG: 0.11→0.07% ID/g @ 1, 4 h→Low, and washing out. Good POS/NEG ratio, increasing over time.

FIG. 7 shows biodistribution data for compound 3 (18F-FBA-PEG28-PEG28-A20FMDV2) in BxPC-3 (and MIA PaCa-2) tumors. Key observations include fast blood clearance: (1) Renal clearance (Urine moderate at 1 h (~1500% ID/g); Kidneys high—NOT clearing (43% ID/g→42% ID/g @ 1 h, 4 h); (2) Minor GI clearance (Gall bladder <1.5% ID/g; Liver <0.2% ID/g Stomach moderate—going somewhat up (2.3% ID/g→6.6% ID/g @ 1 h, 4 h); (3) Lung 1.7→1.3% ID/g @ 1 h, 4 h. Tumors were moderate size. Tumor size appeared to have no effect on % ID/g: POS: 1.6→2.1% ID/g @ 1, 4 h→Steady, increasing, Higher uptake & retention than Dx3puroB6; NEG: 0.22→0.12% ID/g @ 1, 4 h→Low, and washing out. Good POS/NEG ratio, significantly increasing over time.

Figure 8:
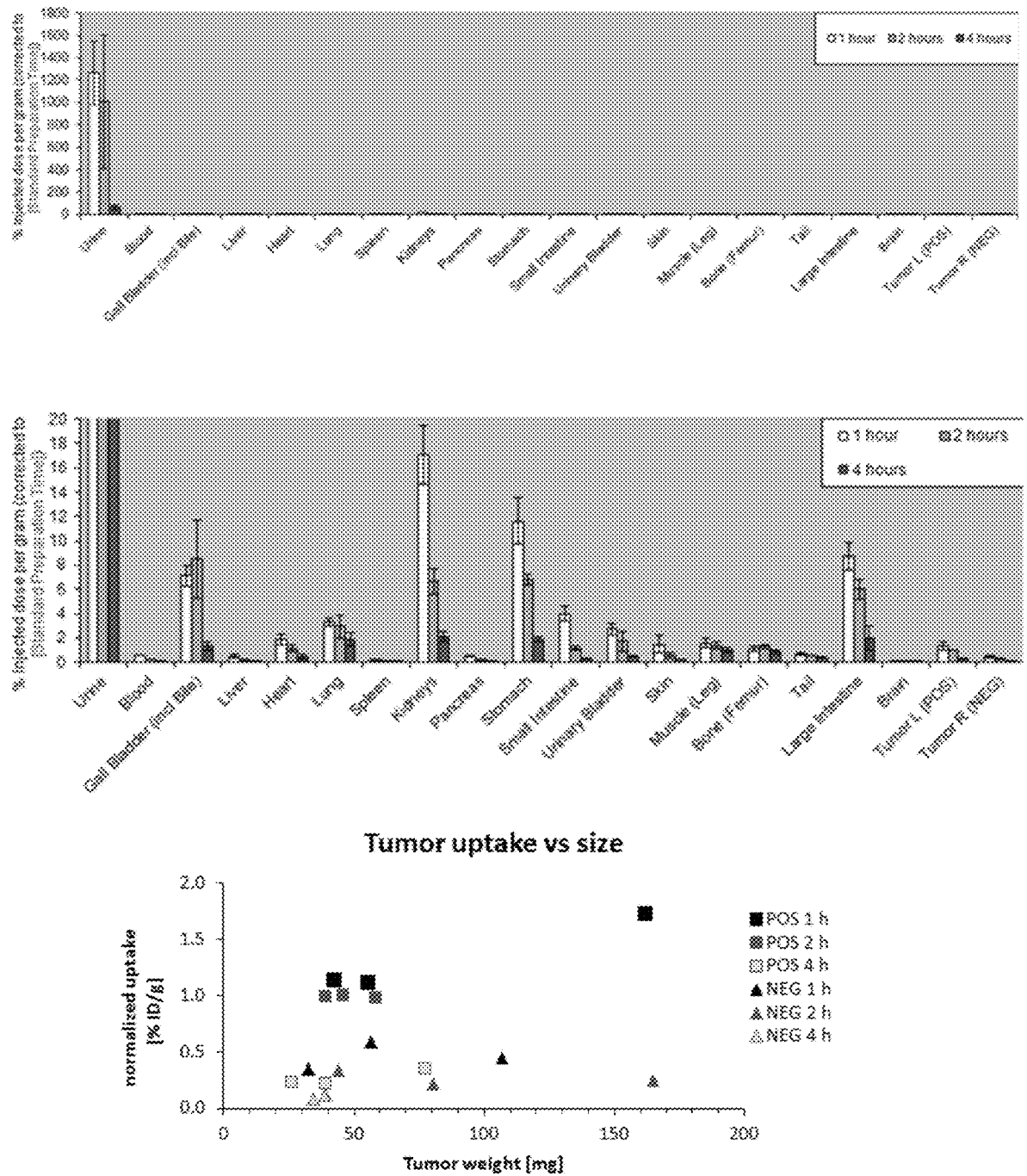
FIG. 8 shows biodistribution data for compound 4 (18F-FBA-A20FMDV2-PEG28) in DX3puroβ6 and Dx3puro tumors.

FIG. 8 shows biodistribution data for compound 4 (18F-FBA-A20FMDV2-PEG28) in DX3puroB6 and Dx3puro tumors. Key observations include fast blood clearance: (1) Renal clearance (Urine very high at 1.2 h (>1000% ID/g)), Kidneys comparatively low, and clearing well over time to ~2% ID/g); (2) Minor GI clearance (Gall bladder <10% ID/g—clearing; Stomach ~12% ID/g→2% ID/g—clearing; LgInt ~9→2% ID/g-clearing; Liver low (!) <0.5% ID/g & dropping); (3) Lung ~3→2% ID/g—small drop. Mostly small tumors. Tumor size appeared to have no/minimal (POS 1 h) effect on % ID/g: POS: 1.3, 1.0, 0.3% ID/g at 1,2,4 h→Moderate, and washing out; NEG: 0.5, 0.3, 0.1% ID/g at 1,2,4 h→Low, and washing out. Moderate, relatively steady POS/NEG over time.

Figure 9:
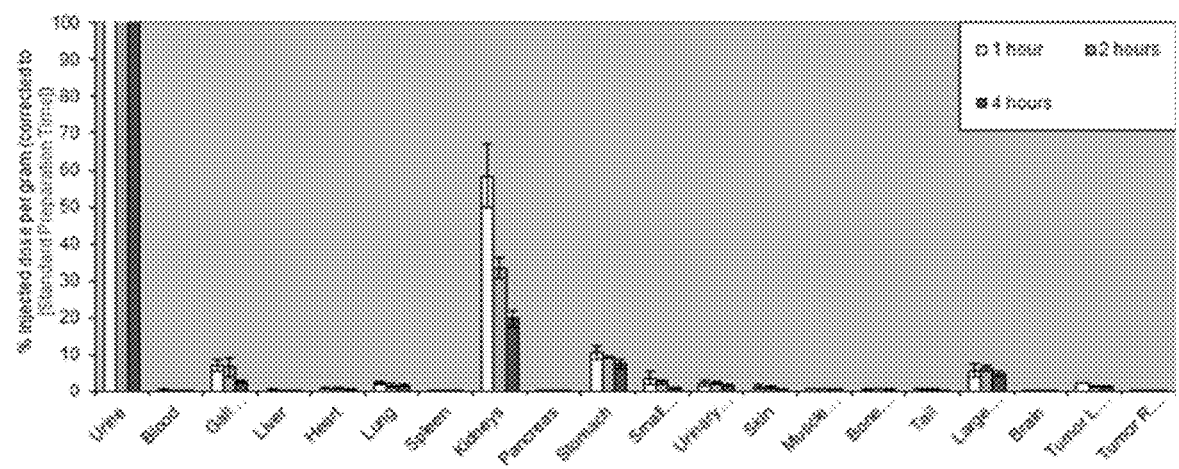
FIG. 9 shows biodistribution data for compound 5 (18F-FBA-PEG28-A20FMDV2-PEG28) in DX3puroβ6 and Dx3puro tumors.
Figure 9:
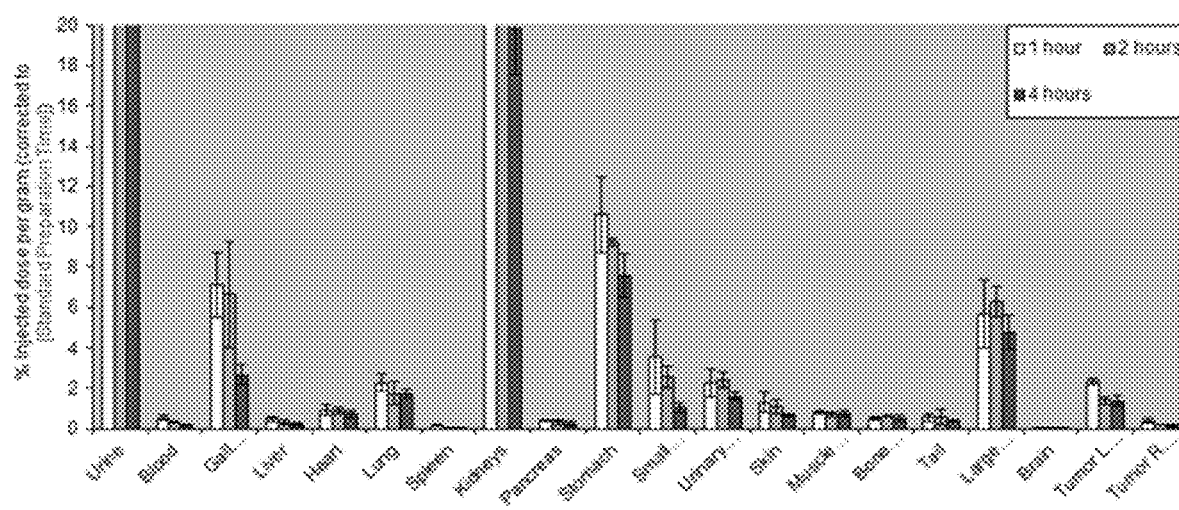
Figure 9:
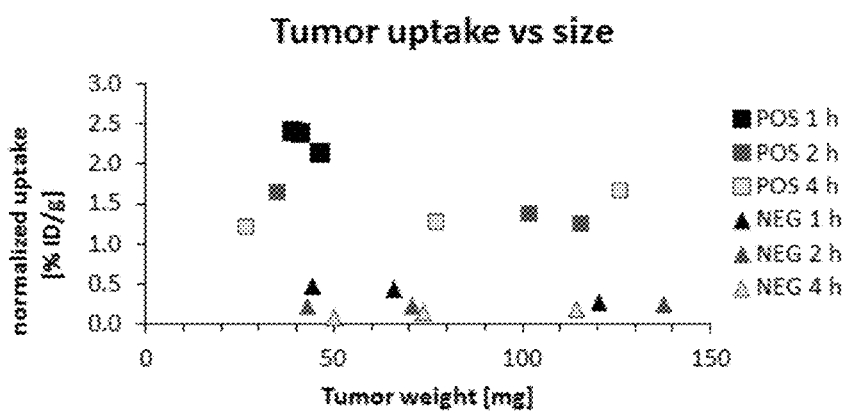

FIG. 9 shows biodistribution data for compound 5 (18F-FBA-PEG28-A20FMDV2-PEG28) in DX3puroB6 and Dx3puro tumors. Key observations include fast blood clearance: (1) Chiefly renal clearance (urine: high, clearing, 396→135% ID/g @ 1 h, 4 h); kidneys: high, clearing, 58→20% ID/g @ 1 h, 4 h); (2) Some GI clearance (Gall bladder 7→2.7% ID/g @ 1 h, 4 h; Stomach 11%→8% ID/g @ 1 h, 4 h ID/g—slow clearing; LgInt ~5% ID/g steady; Liver low <0.5% ID/g @ 1 h, dropping); (3) Lung ~2% ID/g steady. Evaluated mostly small tumors. Tumor size appeared to have no effect on % ID/g: POS: 2.3→1.4% ID/g @ 1 h, 4 h→Drop after 1 h, then steady; NEG: 0.39→0.14% ID/g @ 1 h, 4 h→Low, and washing out. Good POS/NEG ratio, increasing over time.

Figure 10A:
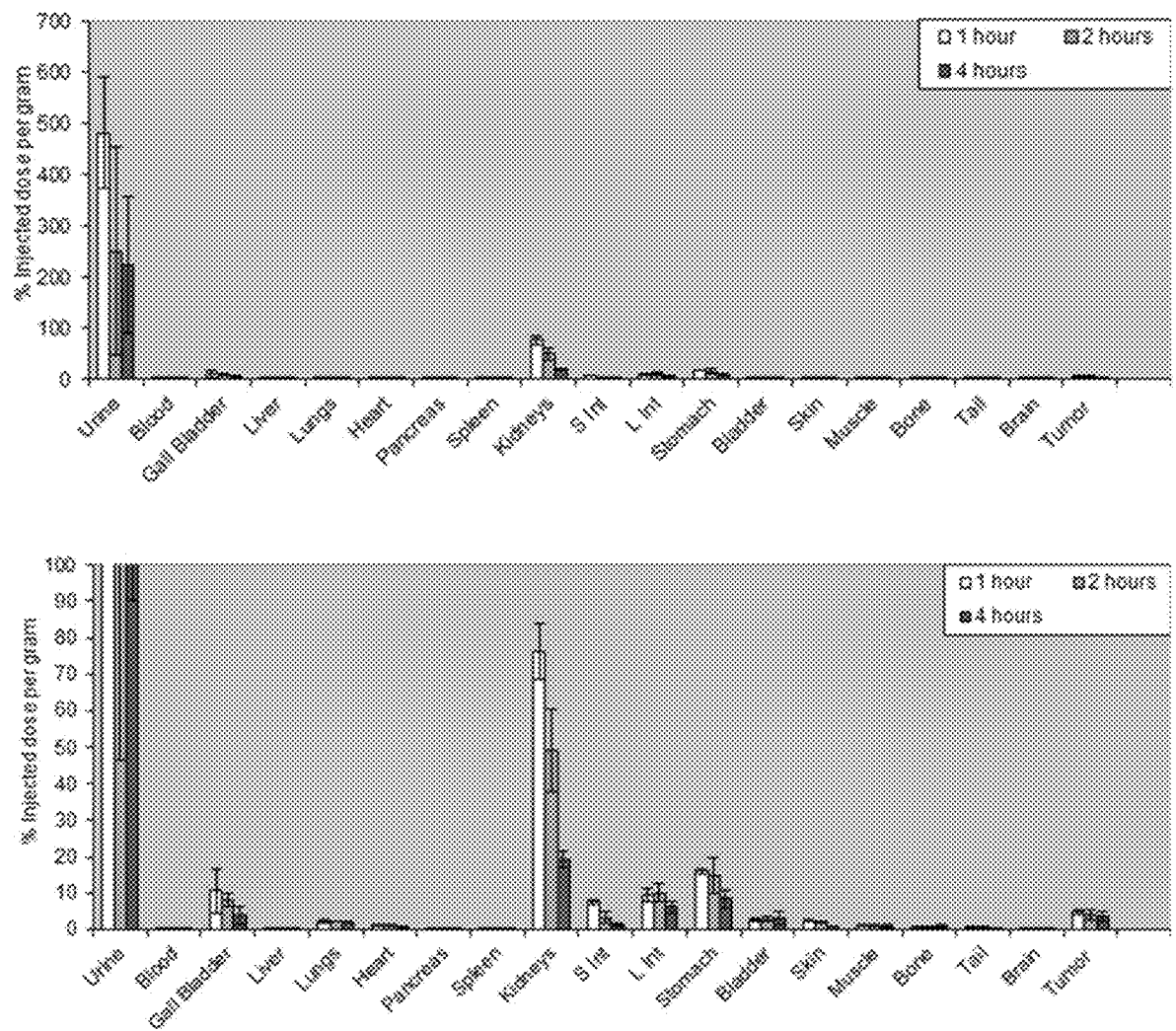
FIG. 10A and FIG. 10B show biodistribution data for compound 5 (18F-FBA-PEG28-A20FMDV2-PEG28) in BxPC-3 tumors.
Figure 10B:
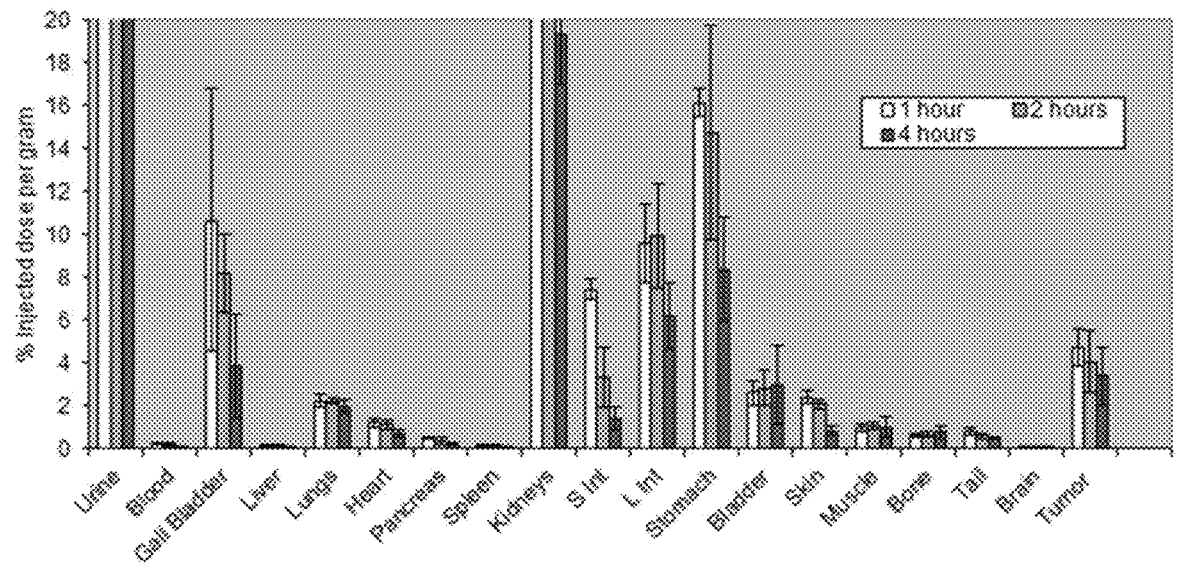
Figure 10B:
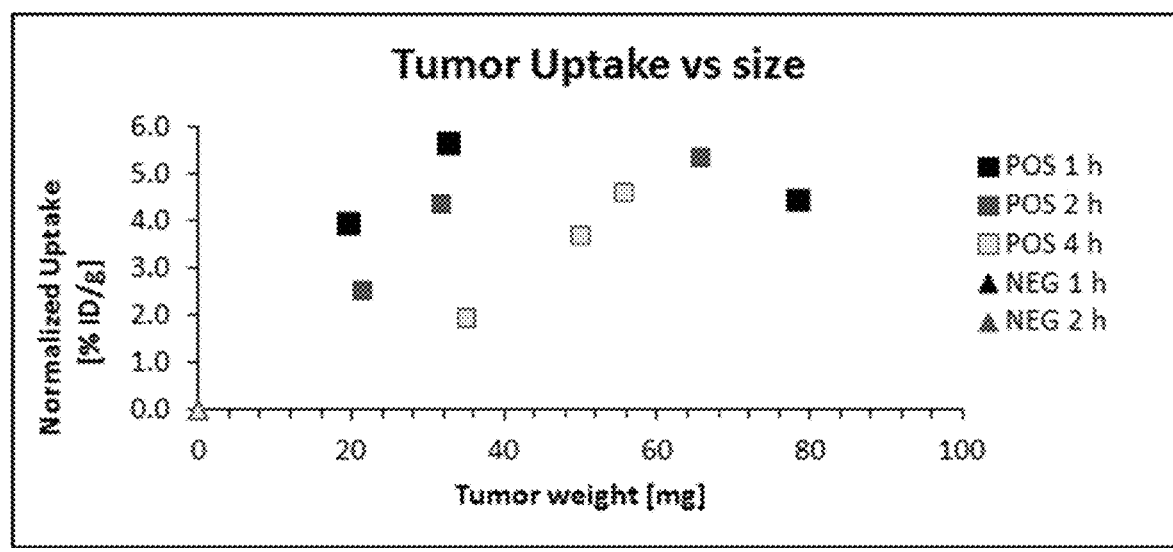
Figure 11:
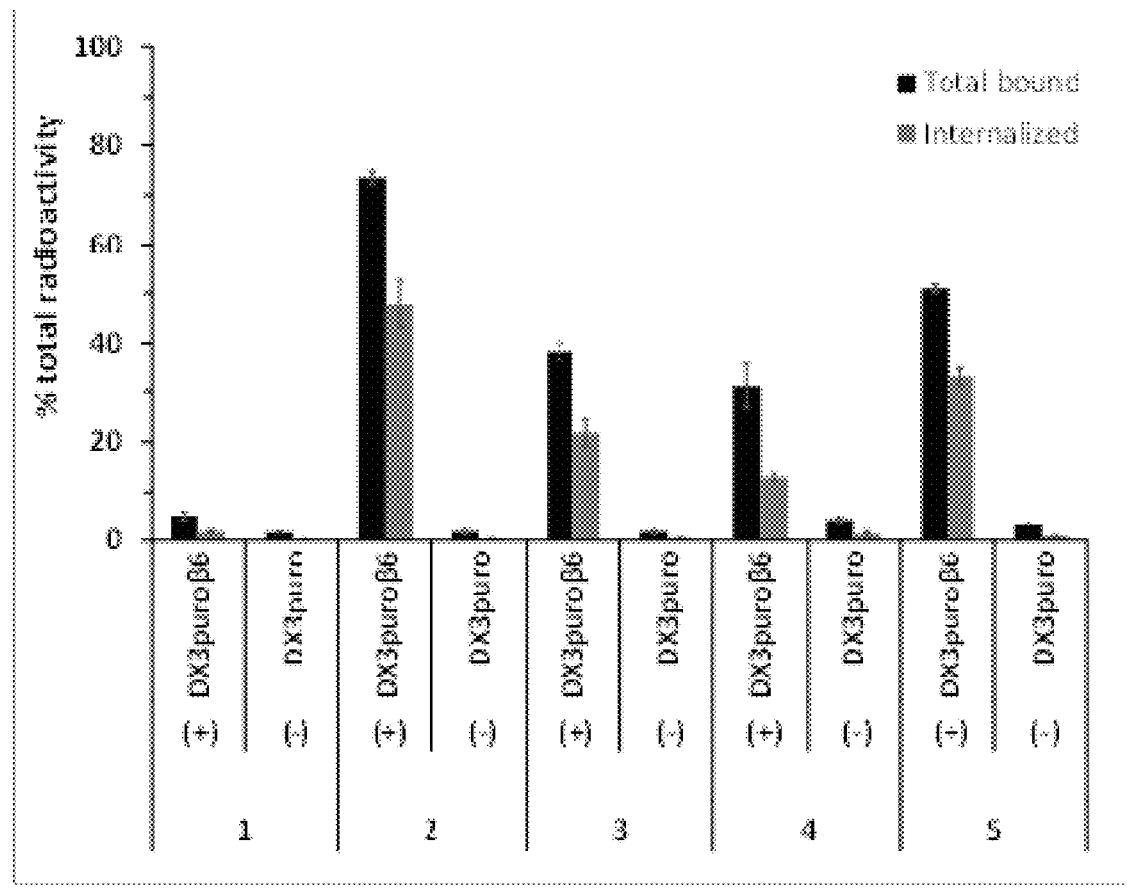
FIG. 11 shows the binding and internalization of the radiotracers in vitro using the integrin $\alpha_v\beta_6$-expressing DX3puroβ6 cell line (+) and its non-expressing DX3puro control (−). The plots, displaying fraction of total radioactivity, represent quadruplicate experiments with 3.75×10$^6$ cells for each radiotracer/cell line after a 60 minute incubation period. Filled columns: percentage of total radioactivity detected in the cell sample (black: total bound; gray: internalized); bars: S.D. Student's unpaired 2-tailed t test for the DX3puroβ6/DX3puro pair: P≤0.0001 for corresponding data-sets between the two cell lines for each, total bound and internalized data. Data for compounds 1-3 are reproduced from Hausner et al., Cancer Res 2009; 69:5843-50.
Figure 12:
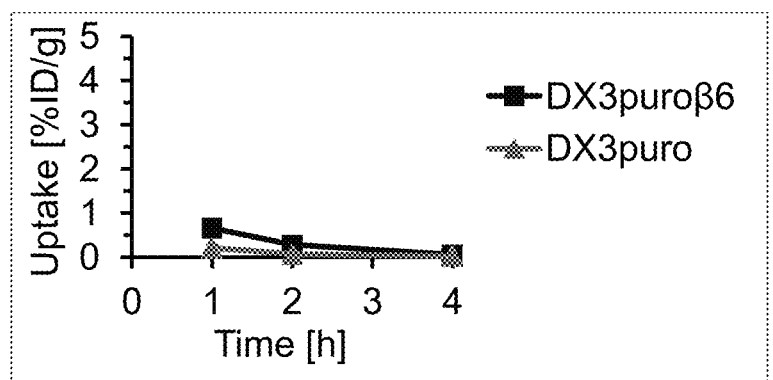
FIG. 12 shows in vivo data for compound 1 determined by biodistribution studies in a xenograft mouse model. Tumor xenograft uptake (A) and uptake ratio (B), and kidney uptake (C). Uptake data are expressed in % injected dose/gram (% ID/g). Data points: % ID/g; bars: S.D; n=3/time point.
Figure 12:
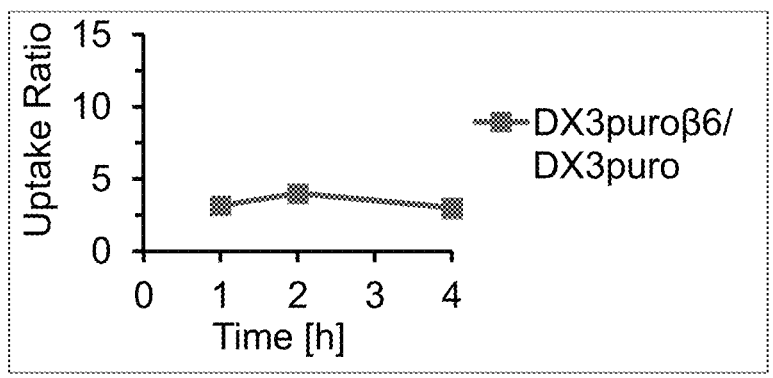
Figure 12:
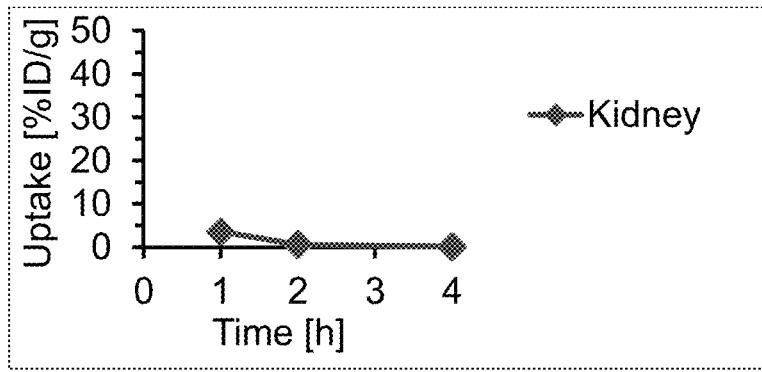
Figure 13:
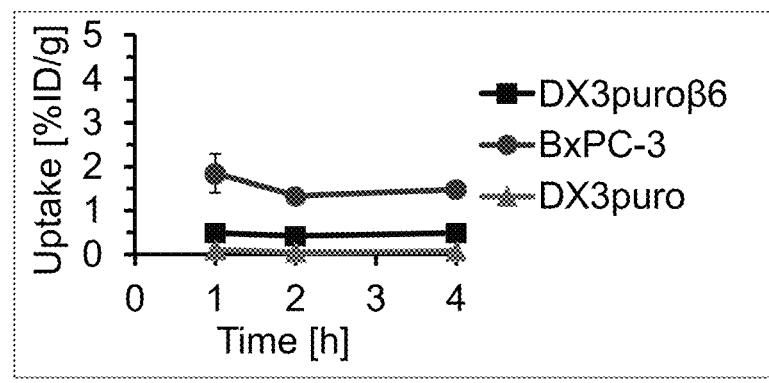
FIG. 13 shows in vivo data for compound 2 determined by biodistribution studies in a xenograft mouse model. Tumor xenograft uptake (A) and uptake ratio (B), and kidney uptake (C). Uptake data are expressed in % injected dose/gram (% ID/g). Data points: % ID/g; bars: S.D; n=3/time point.
Figure 13:
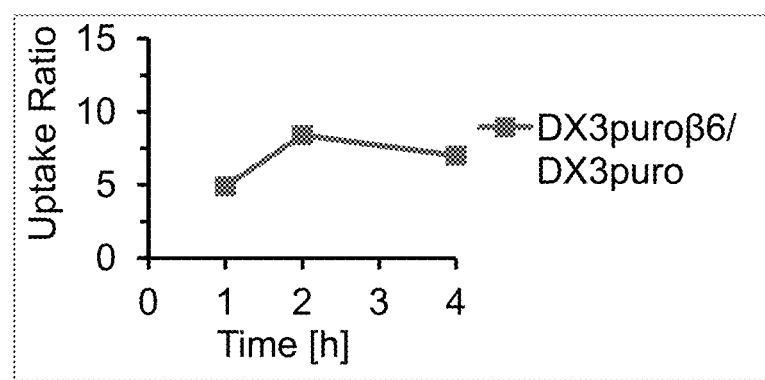
Figure 13:
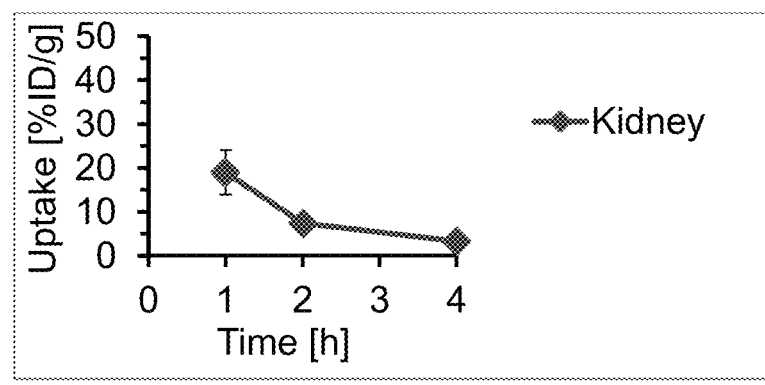
Figure 14:
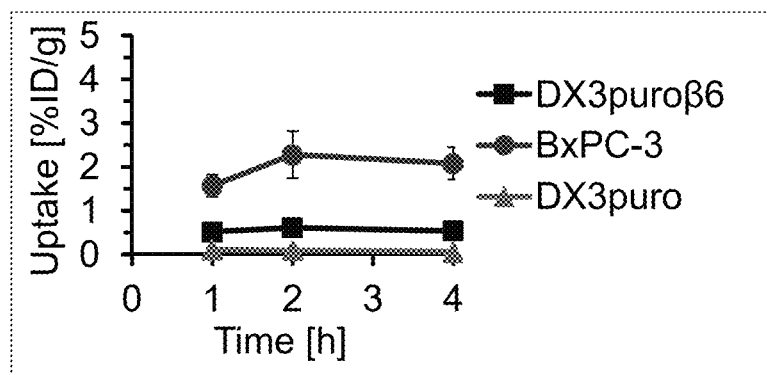
FIG. 14 shows in vivo data for compound 3 determined by biodistribution studies in a xenograft mouse model. Tumor xenograft uptake (A) and uptake ratio (B), and kidney uptake (C). Uptake data are expressed in % injected dose/gram (% ID/g). Data points: % ID/g; bars: S.D; n=3/time point.
Figure 14:
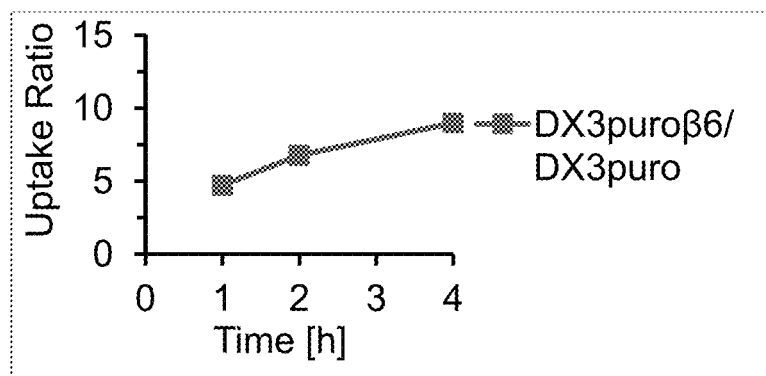
Figure 14:
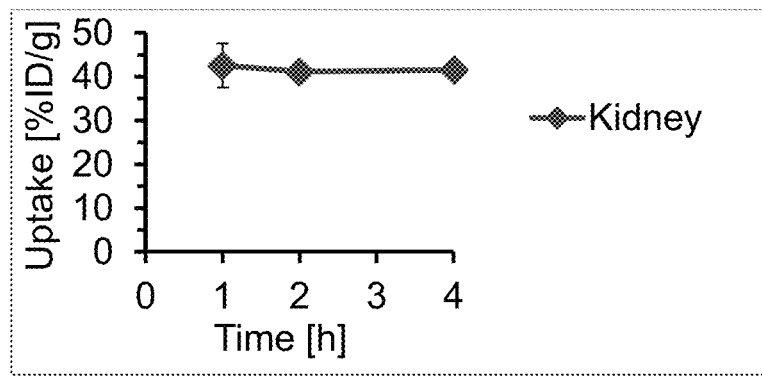
Figure 15:
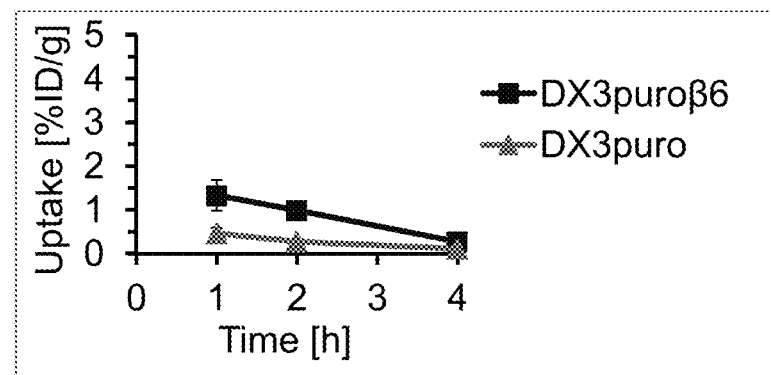
FIG. 15 shows in vivo data for compound 4 determined by biodistribution studies in a xenograft mouse model. Tumor xenograft uptake (A) and uptake ratio (B), and kidney uptake (C). Uptake data are expressed in % injected dose/gram (% ID/g). Data points: % ID/g; bars: S.D; n=3/time point.
Figure 15:
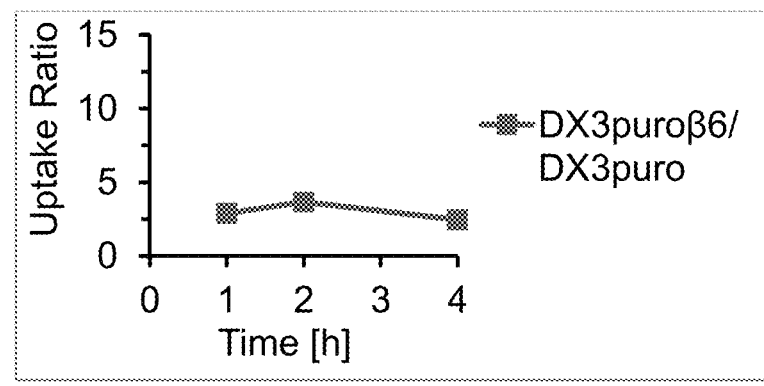
Figure 15:
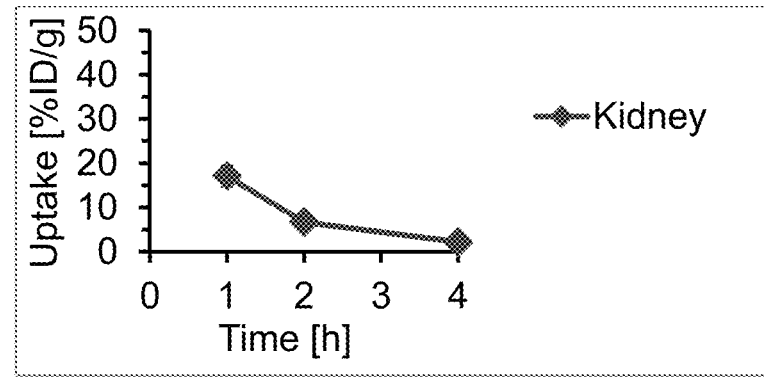
Figure 16:
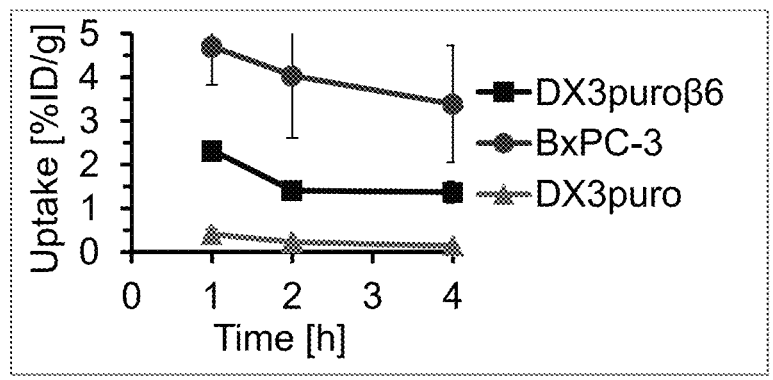
FIG. 16 shows in vivo data for compound 5 determined by biodistribution studies in a xenograft mouse model. Tumor xenograft uptake (A) and uptake ratio (B), and kidney uptake (C). Uptake data are expressed in % injected dose/gram (% ID/g). Data points: % ID/g; bars: S.D; n=3/time point.
Figure 16:
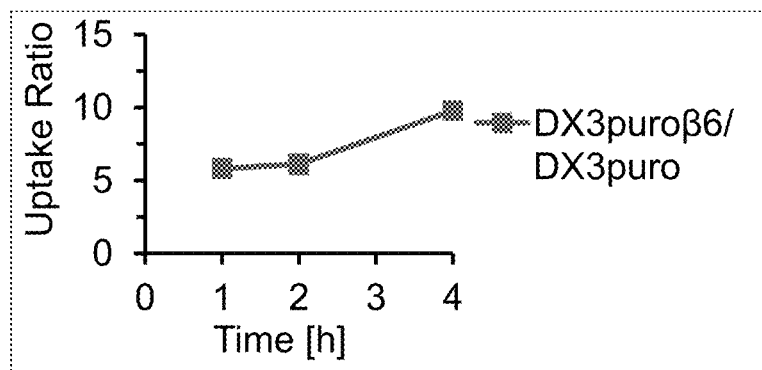
Figure 16:
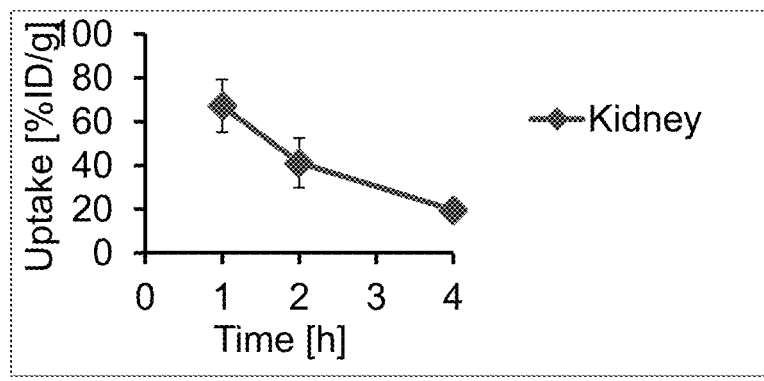
Figure 18:
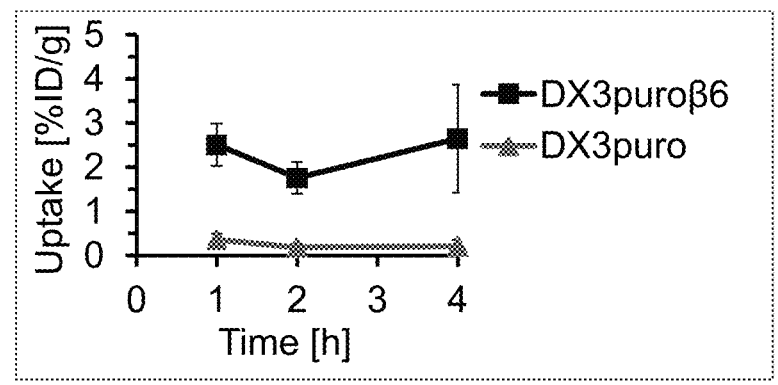
FIG. 18 shows in vivo data for compound 5R determined by biodistribution studies in a xenograft mouse model. Tumor xenograft uptake (A) and uptake ratio (B), and kidney uptake (C). Uptake data are expressed in % injected dose/gram (% ID/g). Data points: % ID/g; bars: S.D; n=3/time point.
Figure 18:
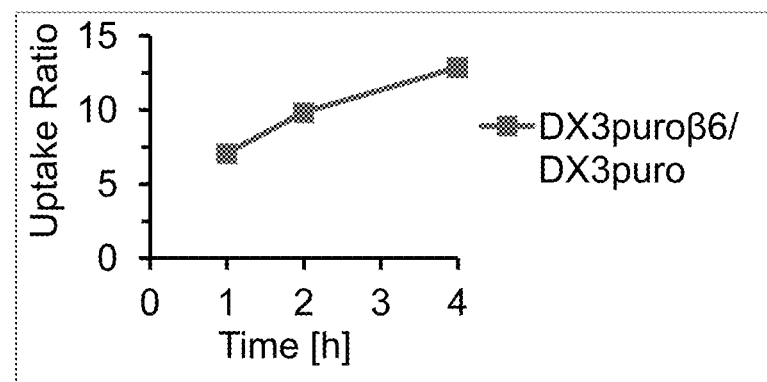
Figure 18:
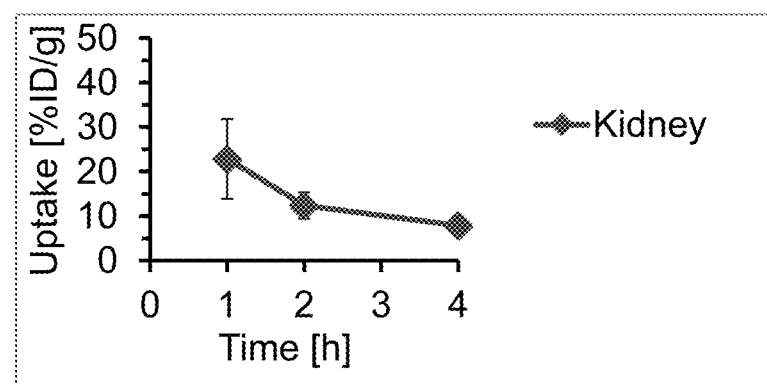
Figure 19:
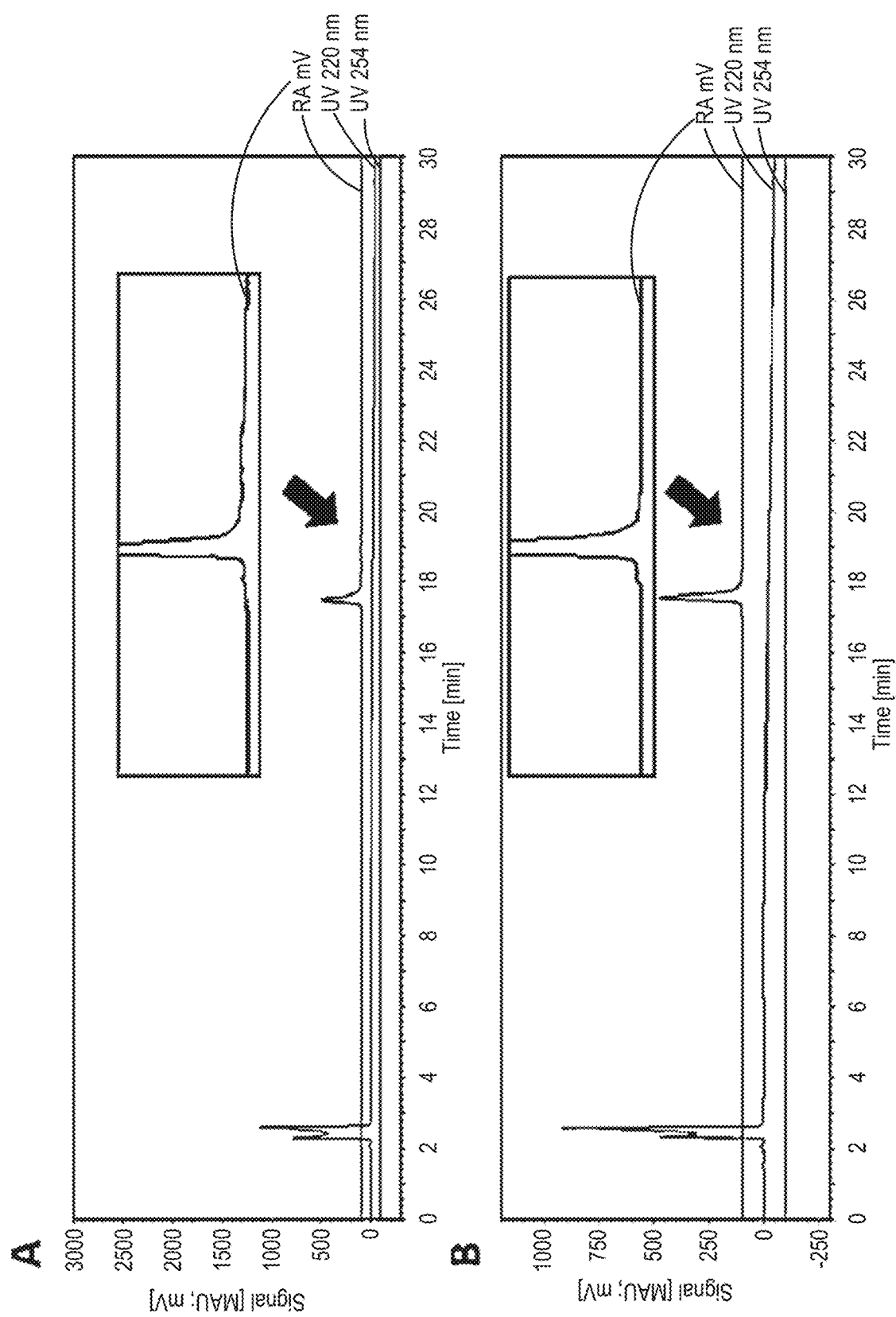
FIG. 19 shows representative HPLC traces of formulated compounds 5 (A) and 5R (B). The radio-HPLC trace is the top trace; also displayed are UV traces at 220 nm (middle trace) and 254 nm (bottom trace). Note the raised baseline around the product peak of compound 5 (indicative of partial decomposition, possibly due to oxidation or radiolysis); by comparison, the baseline around the product peak of compound 5R remains flat. The early spikes in the 220 nm trace are caused by the injection solvent; "solvent front". Abbreviations: for UV absorbance the units are milli Absorbance Units [mAU]; for the radioactivity [RA] signal the units are milliVolt [mV], overlaid onto the UV scale.

FIGS. 10A and 10B show biodistribution data for compound 5 (18F-FBA-PEG28-A20FMDV2-PEG28) in BxPC-3 tumors. Key observations include very rapid blood clearance: Major excretion route is renal, some hepatobiliary too. Tumor uptake: Very good (4.7% ID/g @ 1 h), dropping slightly to 3.4% ID/g@4 h. Other organs of note: Urine very high early on (482% ID/g @ 1 h), dropping (223% @ 4 h), Kidneys high (76% ID/g @ 1 h), washing out (19.3% ID/g @ 4 h), Some GI clearing: gall bladder, stomach, intestines (all <20% ID/g @ 1 h, <10% ID/g @ 4 h), Lungs slightly elevated (~2% ID/g, steady over time), Liver, pancreas: low (<1% ID/g). Washout: Low in tumor, good from most organs. Lungs, pancreas, muscle, and bone appear more steady. Tumor sizes: 20-80 mg (small). Tumor uptake: 4.7→3.4% ID/g @ 1 h, 4 h→High, then slight drop. Higher uptake than Dx3puroB6. Smallest tumors appear to have somewhat lower uptake (within each cohort). Tumor-to-organ ratios: good to excellent, except for Tumor/Kidney. Blocking experiment performed: Blocking agent/amount/time: 30 mg/kg FBA-PEG28-A20FMDV2 (SEQ ID NO:20) @ T=−10 min; Observations: Greatly reduced tumor uptake (reduced by 92% vs unblocked); % Dig of intact tracer in urine is slightly higher than for unblocked samples; All organs, except urine and gall bladder, showed drop in % ID/g, including kidneys, lungs, intestines, and stomach.

Stability of the compounds was assessed by analyzing urine metabolites. Compound 1 (18F-FBA-A20FMDV2) was metabolized into 3 metabolites with shorter Rt. Radiotracer eluted at 15.9 min. Urine metabolites of compound 1 eluted at 9.0 min (44%), 10.4 min (30%), and 10.8 min (26%). Ratio varies between animals/time points. Compound 2 (18F-FBA-PEG28-A20FMDV2) was metabolized into a major metabolite with slightly shorter Rt. Radiotracer eluted at 16.2 min. Urine at 1 h: metabolites of compound 2 eluted at 15.4 min (est 90%); 16.4 (est 10%; unlikely to be intact). Urine at 4 h: same as 1 h. Compound 3 (18F-FBA-PEG28-PEG28-A20FMDV2) was metabolized with slightly longer Rt. Radiotracer eluted at 17.4 min. Urine at 1 h: metabolites of compound 3 eluted at 17.8 min, with small 18.1 min shoulder. Compound 4 (18F-FBA-A20FMDV2-PEG28) was metabolized into 3 metabolites with shorter Rt. Radiotracer eluted at 17.0 min. Urine metabolites of compound 4 eluted at 10.3 min, 11.7 min, and 12.1 min. In contrast to the compounds 1-4, a large fraction of compound 5 (18F-FBA-PEG28-A20FMDV2-PEG28) remained intact, with only one metabolite with slightly longer Rt. Radiotracer eluted at 17.4 min. Urine: 17.4 min (1 h 69%, 1 h 67%, 2 h 78%, 4 h 45% intact); 18.6 min (1 h 31%, 1 h 29%, 2 h 16%, 4 h 55% main metabolite).

Additional stability studies were performed for compound 5 (18F-FBA-PEG28-A20FMDV2-PEG28). In the DX3puroB6 tumor, there was a good HPLC signal, despite a small tumor. Compound 5 remained mostly intact, with some lead-in metabolites. The peak pattern was similar to the serum stability pattern. At 17.4 min, ~82-84% of compound 5 was intact, while at 17.0-17.2 min, ~14-18% of the likely metabolites with small peaks were observed. In the BxPC-3 tumor, compound 5 achieved 81.45% stability at 1 h post-injection (Rt at 17.46 min), with minor metabolites at 17.19 min (17.88%) and 17.91 min (0.67%). In the kidneys, compound 5 achieved 88.5% stability as a sharp single peak at 1 h post-injection (Rt at 17.4 min), with minor metabolites at 14.5 min (0.4%), 14.9 min (1.3%), 15.2 min (2.3%), and 18.6 min (7.5%). In serum, compound 5 achieved greater or equal to about 80% stability at 2 h. In particular, with serum incubation at 37° C., the amount of compound 5 that remained intact was as follows: 81.7% at 30 min, 80.4% at 60 min, and 79.6% at 120 min (Rt at 17.4 min). In addition, >~92% of compound 5 remained intact in PBS at ~6 h.

Methods

Probe Synthesis

The probe can be synthesized using solid-phase peptide synthesis and solid-phase radiolabeling techniques. Accordingly, the peptide was synthesized, PEGylated, and radiolabeled with a fluorine-18-bearing fluorobenzoic acid ($^{18}$F FBA) prosthetic group on solid support (solid-phase peptide synthesis and solid-phase radiolabeling). The preparation is fully compatible with standard peptide chemistries, thus allowing for site-specific introduction of the PEG chains in the peptide (e.g., at the N-terminus, the C-terminus, or both). Furthermore, the preparation is also fully compatible with solid-phase radiolabeling chemistries, resulting in precisely defined, high-purity radioimaging probes.

The solid support was comprised of peptide-synthesis resin beads bearing Rink-amide linker surface modifications. Amino acids were Fmoc-protected natural (L-) amino acids with trifluoroacetic acid labile side-chain protection. Monodisperse PEG chains, that is, PEG chains with an exactly defined number of ethylene glycol repeating units 'n', were used for PEGylation (reagent used: "Fmoc-amino PEG propionic acid", 88 atoms, molecular weight=1544.8 Da, PolyPure #15137-2790 or Novabiochem #851033), rather than polydisperse PEG which is comprised of polymer mixtures around an average molecular weight. Peptide synthesis and introduction of the PEG units was accomplished using standard solid phase Fmoc/piperidine chemistries under HATU/DIPEA activation in N,N-dimethylformamide. For the introduction of the PEG units, coupling times were extended to several hours. The reaction progress was monitored by the picrylsulfonic acid test. For non-radioactive reference standards, 4-fluorobenzoic acid was attached in the same fashion as the amino acids. Workup consisted of cleavage from the solid support and removal of side-chain protecting groups with trifluoroacetic acid (TFA)/1,2-ethanedithiol (EDT)/triisopropylsilane (TIPS)/water (94/1/2.5/2.5 v/v/v/v) or TFA/TIPS/water (95/2.5/2.5 v/v/v) at r.t. for 3 h, purification on semipreparative reversed-phase HPLC chromatography and removal of the solvent. The product was typically obtained in >95% purity (UV, 220 nm) as a colorless solid. Identity was established by MALDI mass spectrometry.

Current Radiosynthesis

In the current approach, 4-[$^{18}$F] fluorobenzoic acid was attached to the probe on solid phase using HATU/DIPEA activation (30 min, r.t., 5 mg H2N-peptidyl-resin), followed by treatment with a TFA mixture (2×15 min) and HPLC purification (Sutcliffe-Goulden et al., Bioorg Med Chem Lett., 2000; 10:1501-3; Sutcliffe-Goulden et al., *Eur J Nucl Med Mol I.,* 2002; 29:754-9; Hausner et al., *J Med Chem.,* 2008; 51:5901-4). The radiolabeled peptide, [$^{18}$F] FBA-PEG$_{28}$-A20FMDV2-PEG$_{28}$, was obtained as solution in phosphate buffered saline (PBS) in 5% decay corrected radiochemical yield in 4 h synthesis time since end of bombardment (EoB) from [$^{18}$F]F-fluoride. Radiochemical purities were >95%. Identity was confirmed by co-injection with nonradioactive standard and observing co-elution of UV and radio HPLC trace.

Evaluation In Vitro

Stability in PBS

To confirm the stability in PBS, aliquots of the formulated probe were analyzed by analytical HPLC at various time points after storage at room temperature.

Stability in Serum

To confirm stability in serum, blood was collected from mice following euthanasia, allowed to clot for 1 h at room temperature, and centrifuged. Serum was collected and combined with an aliquot of the formulated radiotracer (0.74 MBq) in a microfuge tube. The assay tube was gently shaken and kept at 37° C. Aliquots were withdrawn at selected time points, mixed with absolute ethanol (4° C.) and centrifuged to precipitate serum proteins. Analytical HPLC of supernatant samples was performed to determine the percentage of intact radiotracer.

Cell Binding

To confirm maintained $\alpha_v\beta_6$-targeted binding, cell binding studies were done with the imaging probe. Prior to the experiment, the cell lines were analyzed by flow cytometry to confirm levels of integrin expression. For cell binding experiments, 7.4 KBq aliquots of the radiotracer in serum free medium (pH 7.2) were added to a cell suspension (3.75×10$^6$DX3puroB6, DX3puro, BxPC-3 cells in serum free DMEM) and incubated for 1 h at room temperature in closed microfuge tubes (n=4/cell line). The assay tubes, pretreated with bovine serum albumin to block nonspecific binding, were regularly agitated to prevent settling of the cells. Following centrifugation, the supernatant was removed and the cell pellet was washed with serum free medium. The supernatants were combined, and the cells re-suspended in free medium. The fraction of bound radioactivity was determined with a gamma-counter (cell pellet vs. combined supernatants). To determine the fraction of internalized radioactivity at the 60 min time point, the cells were subsequently treated with acidic wash buffer (pH 2.5, 4° C.) to release surface-bound activity (Reilly et al., *J. Nuclear Medicine,* 2000; 41:429-38), followed by a wash with PBS. The internalized fraction was determined with a gamma-counter (cell pellet vs. radioactivity released into supernatant).

Evaluation In Vivo

Mouse Model

The mouse model for in vivo imaging consisted of athymic nu/nu mice subcutaneously injected with human cancer cell lines in the flanks near the shoulders. For an animal model with internal control, a pair of human melanoma cell lines (DX3) was used, one of which had previously been transfected to express integrin $\alpha_v\beta_6$ (DX3PuroB6) while the other served as negative control (Dx3Puro). For pancreatic cancer studies, the BxPC-3 (naturally expressing $\alpha_v\beta_6$) cell line was chosen. In all cases, levels of integrin expression of the injected cell lines was confirmed by flow cytometry. Animals were used for imaging and biodistribution studies when the tumors had a maximum span of about 2 to 8 mm.

Imaging and Biodistribution

Imaging was carried out on a dedicated high resolution small animal PET/CT system (Siemens Inveon). Data analysis was performed using the accompanying software packet. Experiments were carried out according to standard small animal imaging protocols. Following intravenous (iv) injection of the imaging probe (100-250 into the tail vein of the anesthetized animal (isoflurane), a dynamic 4×15 min scan was performed on the anesthetized animal (isoflurane) beginning 15 min after injection, followed by 15 min scans at later time points (2, 4 h). After each scan, transmission scans and CT scans were done for attenuation correction and anatomical co-registration, respectively.

For biodistribution studies, the animals were injected with the imaging probe (approx. as described above and sacrificed at given time points (1, 2, 4 h pi, n=3 animals/time point). Following dissection, levels of radioactivity were measured for each organ, tissue, or tumor, and decay corrected, normalized uptake values were calculated and expressed as percent of injected dose per gram of tissue (% ID/g).

Stability Studies

Imaging probe recovery from urine: Urine was collected for HPLC analysis during biodistribution studies when possible. Proteins in the urine aliquots were removed by precipitation with a tenfold excess absolute ethanol and subsequent centrifugation. Supernatant samples were evaluated by HPLC.

Imaging probe recovery from tumor: The imaging probe (1 mCi) was injected and the $\alpha_v\beta_6$-positive tumor collected at the 1 h time point. The tumor was homogenized in PBS and proteins precipitated by addition of absolute ethanol. Following centrifugation, the supernatant was collected and remaining proteins precipitated by addition of acetonitrile. A diluted aliquot of the supernatant was evaluated by HPLC.

Imaging probe recovery from kidney: A kidney was collected along with the tumor during the stability study. The kidney was homogenized in PBS and proteins precipitated by addition of absolute ethanol. Following centrifugation, the supernatant was collected and remaining proteins precipitated by addition of acetonitrile. A diluted aliquot of the supernatant was evaluated by HPLC.

Additional In Vivo Experiments

Autoradiography and immunohistochemical straining of tumor tissue: The imaging probe (1 mCi) was injected and tumors collected at 1 h. The tumors were embedded in freezing medium and sectioned immediately (20 μm for autoradiography, 5 μm for histology). Autoradiography samples were exposed to a storage phosphor-screen overnight. The screen was read at a 50 μm resolution using a phosphorimager (GE Healthcare Storm 860). For histological detection of the $\alpha_v\beta_6$ integrin, frozen sections were stored until the radioactivity had decayed, fixed for 5 min with a Periodate-Lysine-Paraformaldehyde solution and washed in Tris buffered saline. Endogenous peroxidase was blocked with 3% hydrogen peroxide in PBS, followed by incubation with 2.5% normal horse serum. The sections were incubated with anti-integrin beta(6) antibody (PBS) for 1 h, washed in TBS and incubated with an peroxidase-labeled secondary antibody (anti goat-Ig). The staining was developed with 3,3'-diaminobenzidine (DAB), counter-stained with Mayer's Hematoxylin, dehydrated and mounted with DPX mounting media. All incubations were performed at room temperature.

Example 2. Positive In Vivo Effects of Bi-Terminal PEGylation of Homing (Tumor Targeting) Peptides and Amino Acid Modification of Peptides for Improved Targeting of Integrin $\alpha_v\beta_6$ This example illustrates that bi-terminal PEGylation was able to confer superior targeting characteristics and in vivo pharmacokinetics on the A20FMDV2 peptide and variants thereof (e.g., K16R variant). In particular, the bi-terminal PEGylated A20FMDV2 and A20FMDV2 (K16R) peptides showed greatly improved pharmacokinetic profile beyond what was predicted from individual N- or C-terminal PEGylation. In fact, the two PEG units acted synergistically to achieve greatly improved stability alongside high $\alpha_v\beta_6$(+)-tumor uptake and retention. As such, this example demonstrates that PEGylation is bio-compatible, and, compared to other strategies (e.g., cyclization), does not impose conformational restrictions, is synthetically simple and straightforward, and can readily be combined with a range of other peptide modifications.

Introduction

The studies described in this example were carried out starting from the 20-amino acid containing model peptide A20FMDV2, a peptide that selectively targets the cell surface receptor integrin $\alpha_v\beta_6$. This integrin has been identified as a prognostic indicator for several challenging carcinomas; in all cases high levels of expression correlate with the severity of disease and poor prognosis (Ahmed et al., *J Histochem Cytochem.,* 2002; 50:1371-80; Elayadi et al., *Cancer Res.,* 2007; 67:5889-95; Liu et al., *Head Neck Oncol.,* 2013; 5:7; Bandyopadhyay et al., *Curr Drug Targets,* 2009; 10:645-52; Bates, *Cell Cycle,* 2005; 4:1350-2; Sipos et al., *Histopathology,* 2004; 45:226-36), making it an important target for diagnosis (e.g., non-invasive imaging with radiotracers) and therapy. In previous small animal imaging studies of A20FMDV2-peptides labeled with 4-[$^{18}$F]fluorobenzoic acid (i.e., [$^{18}$F]FBA), it had been shown that introduction of a poly(ethylene glycol) (PEG) unit can improve pharmacokinetics, including increased uptake in $\alpha_v\beta_6$-expressing tumors (Hausner et al., *Cancer Res.,* 2007; 67:7833-40; Hausner et al., *Cancer Res.,* 2009; 69:5843-50). These studies evaluated the effect of site-specific (N- and/or C-terminal) PEGylation (FIG. 1), yielding the bi-terminally PEGylated radiotracer [$^{18}$F]FBA-$PEG_{28}$-A20FMDV2-$PEG_{28}$ (5) as a lead compound based on stability of the radiotracer and $\alpha_v\beta_6$-targeted tumor-uptake when compared to [$^{18}$F]FBA-labeled A20FMDV2 radiotracers bearing PEG at either the C- or the N-terminus. Amino-acid substitutions were also evaluated with the goal to achieve further benefits from modifications of the peptide sequence. In particular, these studies show that replacement of lysine with an arginine at position 16 in compound 5 to create [$^{18}$F]FBA-$PEG_{28}$-A20FMDV2 K16R-$PEG_{28}$ (5R) provided unexpectedly high $\alpha_v\beta_6$-affinity/-retention/-selectively in vitro and yielded improved in vivo results, displayed good clearing from the kidney, and exhibited high radiotracer stability.

Methods

The radiotracers were prepared and radiolabeled on solid phase using standard peptide chemistries (Hausner et al., *Cancer Res.,* 2007; 67:7833-40; Sutcliffe-Goulden et al., *Eur J Nucl Med Mol Imaging,* 2002; 29:754-9). Using three cell lines, DX3puroβ6 [$\alpha_v\beta_6$(+)], the matched negative control DX3puro [$\alpha_v\beta_6$(−)], and the pancreatic carcinoma BxPC-3 with endogenous $\alpha_v\beta_6$(+)-expression, the radiotracers were evaluated in vitro (cell binding and internalization) and in vivo in mouse models bearing either paired DX3puroβ6/DX3puro or BxPC-3 xenografts.

Results

PEGylation. Size and location of the PEG units significantly affected $\alpha_v\beta_6$-targeting and pharmacokinetics. In cell binding studies, PEGylation generally greatly improved affinity and selectivity for the $\alpha_v\beta_6$-expressing cell line, and resulted in a high degree of internalization into the $\alpha_v\beta_6$-expressing cells, as seen for radiotracers 2-5 (compared to non-PEGylated 1; FIG. 11).

PEGylation also proved beneficial in vivo (as measured by $\alpha_v\beta_6$(+)-tumor uptake and retention, as well as clearing from non-target tissues), but it demonstrated sensitivity to size and placement of the PEG group. Increasing the size beyond a certain point did lead to decreased pharmacokinetic performance as seen for the greatly increased uptake and trapping in kidneys for 3 (bearing two $PEG_{28}$ units at the N-terminus), compared to 2 (bearing one $PEG_{28}$ unit at the N-terminus; FIGS. 13 and 14). Moving the (single) $PEG_{28}$ unit to the C-terminus (4) had minimal effect on kidney retention, but, unfortunately, decreased retention in the $\alpha_v\beta_6$-positive xenograft (FIGS. 13 and 15).

Surprisingly, when attaching one $PEG_{28}$ unit at the N-terminus and one $PEG_{28}$ unit at the C-terminus (yielding 5), the positive effects were conserved or even improved (high $\alpha_v\beta_6$-affinity/-retention/-selectively) while largely avoiding the negative in vivo side-effects (viz renal trapping). In vitro, 5 bound to the $\alpha_v\beta_6$(+)-expressing cell lines DX3puroβ6 and BxPC-3 with 51.0±0.9% and 37.2±1.9%, respectively, with much of the radioactivity internalized (DX3puroβ6: 33.5±1.8%, BxPC-3: 28.4±0.9% of total radioactivity, respectively; FIG. 11). By comparison, the control cell line DX3puro showed 3.5±0.2% binding and 0.9±0.1% internalization. In vivo, 5 maintained high, $\alpha_v\beta_6$-directed binding in the paired DX3puroβ6/DX3puro model (ratio: 1 h: 5.8/1; 4 h: 9.8/1). High uptake was also observed in the pancreatic BxPC-3 model (uptake: 1 h: 4.71±0.88% ID/g; 4 h: 3.39±1.34% ID/g) even though very small tumors were present (43±19 mg; FIG. 16). These studies indicate that 5 is beneficial for the detection of small $\alpha_v\beta_6$-positive primary tumors and metastases. These studies also indicate that, in contrast to other A20FMDV2-tracers, 5 stayed mostly intact (>80% at 1 h in tumor).

Amino acid substitutions; replacement of Lys16. The lysine at position 16 was targeted for replacement for several reasons, notably (1) the lysine side-chain amine group precludes the possibility of site-specific amide-bond-based radiolabeling (such as, for example, with [$^{18}$F]FBA) of the peptide in solution phase because this amine group would compete with the N-terminal amine for binding to the prosthetic group (this is not a concern during solid-phase radiolabeling because the amino-acid side chains, including the amine group of the lysine, remain protected until after radiolabeling), and (2) replacement by similarly basic amino acids (but lacking the amine) may increase stability while maintaining target affinity and selectivity. Initial studies evaluating the importance of the lysine at position 16 by cell binding experiments were carried out with the monoPEGylated 2: substitutions were done with the simple alkyl amino acid alanine (substitution: K16A; 2A); the acidic amino acid glutamic acid (K16E; 2E); and the basic amino acid arginine (K16R; 2R). As shown in FIG. 17, only the K16R substitution (2R) maintained affinity and selectivity for the $\alpha_v\beta_6$(+)-expressing cell line DX3puroβ6, indicating that a basic (but not necessarily an amine) side group in this position is important. By contrast, the non-functionalized (K16A) and acidic (K16E) modifications led to a significant decrease in performance.

The combination of K16R modification with bi-terminal PEGylation (to yield [$^{18}$F]FBA-PEG$_{28}$-A20FMDV2 K16R-PEG$_{28;~5}$R) showed maintained excellent affinity and selectivity for the $\alpha_v\beta_6$(+)-expressing cell line DX3puroβ6 (FIG. 17). Therefore, compound 5R was also tested in vivo in the paired DX3puroβ6/DX3puro xenograft mouse model. As shown in FIG. 18, 5R demonstrated a pharmacokinetic profile better than that seen for its parent 5 (FIG. 16): the DX3puroβ6/DX3puro xenograft uptake ratio was higher for all time points evaluated (reaching 12.9/1 at 4 h), while the radioactivity concentration in the kidney was lower throughout. The overall benefit of the K16R mutation is also illustrated by the biodistribution data listed in FIG. 29: the large majority of tissues showed lower % ID/g uptake for 5R than for 5 (exceptions: gall bladder (higher, but acceptable absolute uptake), lung (approx. equal), and DX3puroβ6 tumor (higher—desirable), and, accordingly, key DX3puroβ6/organ ratios increased notably for 5R over 5. As an additional benefit, the K16R substitution also had positive effects on radiotracer stability, as shown in FIG. 19: no partial decomposition (indicative of radiolysis/oxidation) was observed for the formulated 5R, whereas the parent 5 commonly displayed around 5% decomposition in the radiotracer formulation.

Conclusion

With respect to addition of PEG units, only the bi-terminal PEGylation was able to confer good targeting-characteristics and a good overall in vivo profile on the A20FMDV2-based radiotracers, as seen for compound 5: It showed a greatly improved pharmacokinetic profile, beyond what was predicted from individual N- or C-terminal PEGylation. The two PEG units acted synergistically to achieve greatly improved stability alongside high $\alpha_v\beta_6$(+)-tumor uptake and retention. This bi-terminal PEGylation strategy may also be beneficial for other homing peptides, similar to cyclization (White et al., *Nat Chem.,* 2011; 3:509-24; Okarvi, *Med Res Rev.,* 2004; 24:357-97; Roxin et al., *Future Med Chem.,* 2012; 4:1601-18). Notably, PEGylation is bio-compatible, and, compared to other strategies (e.g., cyclization), does not impose conformational restrictions, is synthetically simple and straightforward, and can readily be combined with a range of other peptide modifications.

When evaluating the bi-terminal PEGylation strategy for $\alpha_v\beta_6$(+)-targeting peptides based on A20FMDV2, modifications at the lysine residue were investigated and the K16R substitution was found to be particularly beneficial. Compound 5R maintained high $\alpha_v\beta_6$-affinity/-retention/-selectively in vitro and yielded improved in vivo results (including the best $\alpha_v\beta_6$(+) DX3puroβ6/$\alpha_v\beta_6$(−) DX3puro xenograft ratio of 12.9/1), showed good clearing from the kidney, and high radiotracer stability.

Example 3. Development of Bi-Terminal PEGylated Peptides with Improved Affinities and Pharmacokinetics for $\alpha_v\beta_6$-Targeted Molecular Imaging and Therapy This example illustrates the development of novel molecular imaging agents with improved affinities and pharmacokinetics and the development and testing of the efficacy of several novel $\alpha_v\beta_6$-targeted therapeutic strategies. In particular, this example provides $\alpha_v\beta_6$-targeted therapy based on $PEG_{28}$-A20FMDV2(K16R)-$PEG_{28}$ (SEQ ID NO:21) as a delivery vehicle for three therapeutic strategies: (i) the pro-apoptotic peptide $_D(KLAKLAK)_2$ (SEQ ID NO:6); (ii) the therapeutic radionuclide $^{90}Y$; and (iii) a micelle-based paclitaxel (PTX) nanocarrier. This example also provides modifications including multimerization and/or the addition of a blood albumin binding motif to further improve the affinity, in vivo stability, targeting capabilities, and/or clearance behavior of $PEG_{28}$-A20FMDV2(K16R)-$PEG_{28}$ (SEQ ID NO:21).

Background and Clinical Significance

The $\alpha_v\beta_6$ integrin as a molecular target for cancer imaging and therapy: There is a significant and rapidly growing body of literature that suggests the $\alpha_v\beta_6$ integrin to be an extremely attractive molecule for imaging and therapy. $\alpha_v\beta_6$ is an epithelial-specific cell surface receptor that is undetectable in healthy adult epithelium but is significantly upregulated in a wide range of epithelial derived cancers (1-12). This receptor is often localized to the invasive front and infiltrating edges of tumors and plays a key role in invasion and metastasis and its expression is often associated with poor prognosis (13-19). With the unique expression of $\alpha_v\beta_6$ being a predictor of decreased progression free survival (PFS), response rate (RR) and overall survival (OS) (20, 21), we and others believe that the silver lining of this negative correlation is the much needed opportunity to utilize $\alpha_v\beta_6$ for both diagnostic and therapeutic measures. The high contrast between malignant and healthy tissue and the functional relevance of $\alpha_v\beta_6$, especially in those diseases with a more aggressive phenotype, together place $\alpha_v\beta_6$ squarely on an elite list of targets for which development of diagnostic and therapeutic compounds will be vital to the future management of a very wide range of invasive diseases.

Clinical impact of $\alpha_v\beta_6$ targeted molecular imaging agents and therapeutics: In addition to the high contrast gained due to aberrant, but specific expression of $\alpha_v\beta_6$, the scope of diseases exhibiting this contrast will not be limited in utility to a small group of patients. Rather, these $\alpha_v\beta_6$-targeted imaging and therapeutic agents have the potential to be prominent in the treatment and management of several malignancies that, by origin or grade, lie outside our current curative potential. Literature reports to support these claims 22-25) are numerous and increasing exponentially as the broad biological impact and clinical utility of $\alpha_v\beta_6$ become dogma. Here, we highlight the most recent indications/applications in colorectal and breast cancer that cumulatively demonstrate the immediacy with which development of $\alpha_v\beta_6$ targeted diagnostics and therapeutics must occur.

Colorectal cancer (CRC) is the second most common cause of cancer related death, highly attributable to liver metastasis (11, 18, 26). Numerous reports reveal a definite role of $\alpha_v\beta_6$ in cell migration, proliferation and invasion within CRC models as well as reported cross-talk between $\alpha_v\beta_6$ and CXCR4 further defining $\alpha_v\beta_6$'s role in liver metastasis (25). In a recent phase II trial, the efficacy of Abituzumab combined with cetuximab/irinotecan standard of care (SoC) in the treatment of patients with KRAS w/t metastatic colorectal cancer was explored (27). This study confirmed $\alpha_v\beta_6$ as negatively prognostic for OS of patients receiving SoC. Additionally, increased $\alpha_v\beta_6$ expression was determined by retrospective biomarker analysis to be positively correlated with increased OS (risk of death reduced by up to 59% over SoC) and likely to also be a positive predictor of PFS and RR for the combined Abituzimab/SoC treatment regimen. The primary endpoint (PFS) was not met in this randomized study; an outcome the authors suggested may be reversed by selection of a patient population more likely to benefit from combined treatment (i.e., patients with $\alpha_v\beta_6$+ metastases). In the words of the authors and highlighting the critical but unmet need for $\alpha_v\beta_6$-targeted diagnostics, "Development of a companion diagnostic test to select the appropriate patient population will be crucial for further trials".

Ductal carcinoma in situ (DCIS) accounts for 25-30% of breast cancers, of which only a small subset will progress to invasive cancer; however, the lack of a prognostic indicator for women with DCIS has led to over-diagnosis and over-treatment. Upon diagnosis, DCIS patients are immediately confronted with serious decisions regarding treatment; the absence of relevant biomarkers to help guide these decisions is a health care failure that must be corrected. The big question still remaining for patients is, "Will my DCIS develop into invasive cancer during my lifetime?" Currently, DCIS patients are treated as if they will progress as no robust markers are available to distinguish DCIS for invasive carcinoma. "*We're treating DCIS not because DCIS per se causes any problems but because it is a major risk factor for the development of invasive cancer*." Monica Morrow, M.D., Chief of Breast Service at MSKCC. The dilemma for those women over 50 whose disease might take decades to progress is whether watching and waiting would be a better option than radical mastectomy. "*If we could identify aa molecular marker that could predict which DCIS would progress to invasive cancer versus which would stay DCIS forever that would be an enormous clinical advance*." Monica Morrow, M.D (28). It is clear that if successful this imaging agent will have a significant impact and benefit both for patients with advanced disease as well as identifying those patients whose disease might never advance and could be used in both a predictive and prognostic setting giving desperately needed information and options to women faced with incredibly difficult treatment decisions. In response to this challenging situation, investigation into predictive biomarkers has accelerated and $\alpha_v\beta_6$ is among the most promising candidates. Retrospective analysis has revealed $\alpha_v\beta_6$ expression in myoepithelial cells in DCIS is a predictor of progression as well as recurrence, with 100% of $\alpha_v\beta_6$+ DCIS associated with invasive disease (14). Development of an $\alpha_v\beta_6$-targeted imaging agent would therefore significantly strengthen the clinicians' ability to stratify patients by risk of progression to invasive cancer and provide DCIS patients much needed information as they consider treatment options.

Of those patients diagnosed with breast cancer, approximately 25-30% are HER2+, a more aggressive subgroup. Trastuzumab is used as an adjuvant treatment for HER2+ patients, but unfortunately over 70% of patients develop resistance and new therapies are sorely needed. Recent evidence has shown $\alpha_v\beta_6$+/HER2+ disease to be one of the most devastating classes of breast cancer with OS barely above 50% (OS for HER2+ patients, independent of $\alpha_v\beta_6$ status, is 65.1%). While the pathology of trastuzumab resistance is heterogeneous, members of the PI3K signaling axis are commonly involved and there is substantial data demonstrating direct linkage and cross-talk between $\alpha_v\beta_6$ and this pathway. Again, this observation allows for, at minimum, stratification of patients based on $\alpha_v\beta_6$ expression and more informed treatment considerations, both of which are dependent of course on the availability of an $\alpha_v\beta_6$-targeted diagnostic. Within the context of treatment of HER2+ disease, acquisition of trastuzumab resistance is a critical clinical issue. For those patients whose disease eventually circumvents the effect of trastuzumab, therapeutics directly targeting $\alpha_v\beta_6$ signaling or simply targeted to $\alpha_v\beta_6$+ cells offer an additional treatment option at a stage lacking in alternatives.

While the list of diseases in which $\alpha_v\beta_6$ has been identified continues to expand greatly, $\alpha_v\beta_6$ was initially identified in pancreatic cancer. Sipos et al. demonstrated high levels of $\alpha_v\beta_6$-expression in pancreatic ductal adenocarcinomas (PDAC), with 94% (32/34) of samples receiving the maximum score (29). Pancreatic cancer is the most lethal malignancy in the United States, with greater than 98% of those people diagnosed with the disease ultimately dying from it (30). The only curative treatment for pancreatic cancer exists when localized disease is identified; however, only 20% of patients will be diagnosed when the cancer is limited to the pancreas or regional lymph nodes for which surgical resection offers a chance of cure. Compounding the difficulty of current management, up to 50% of patients thought to have localized disease based on currently available imaging modalities (contrast-enhanced computed tomography [CT] scan or $^{18}$FDG-positron emission tomography-PET/CT) will have metastatic disease at the time of exploratory surgery (31, 32). There is clearly a need for non-invasive imaging to accurately determine the extent of disease so that patients with localized tumors can proceed to exploratory surgery with a high likelihood of undergoing potentially curative resection, while those patients with advanced cancer can avoid exploratory surgery performed only to identify the extent of disease. An NCI sponsored think-tank on PDAC identified methods for early detection as among the most critical unmet needs in combating this disease. The consensus view was that tools allowing earlier detection, patient stratification, and evaluation of therapeutic efficacy at earlier time points are of paramount importance. There is clearly an unmet need for improved imaging agents and therapeutics and $\alpha_v\beta_6$-targeted compounds hold tremendous promise to meet that need.

In summary, $\alpha_v\beta_6$-directed imaging and therapy will provide critical stage and grade (indolence/aggressiveness) information, guide therapy decisions that are difficult to make on the current diagnostic approaches, and have a significant outcome for both the under- and over-treated cancer patients. The clinical impact of the approaches described in this example is immediate for a broad spectrum of diseases and holds potential to break through barriers in the treatment of some of the most lethal malignancies facing clinicians today.

$\alpha_v\beta_6$-specific molecular imaging agents: To date, no molecular imaging agents for $\alpha_v\beta_6$ have made it to the clinic and few are in development. Through unbiased phage bio-panning on lung adenocarcinoma cell lines, Brown et al. identified the 20 amino acid peptide H2009.1 and subsequently identified the binding target as $\alpha_v\beta_6$ (33). They demonstrated that $\alpha_v\beta_6$ is upregulated in many non-small cell lung cancer (NSCLC) patients, is an independent negative prognostic indicator and report that $\alpha_v\beta_6$ is "turned on" in the disease progression of NSCLC (2). In 2013, Brown described the use of this peptide as a tetramer to improve the targeting of a liposomal formulation of doxorubicin (34). Another approach taken by the Gambhir group was an engineered cystine knot $\alpha_v\beta_6$ peptide and they reported two peptides radiolabeled with $^{18}$F-fluorine. Although the peptides were >80% intact in human serum (ex vivo) after one hour, in vivo evaluation of these knottin peptides showed kidney uptake >27% ID/g (35, 36).

Our approach: We have chosen two approaches to identify $\alpha_v\beta_6$ specific peptide ligands. We use a "rational" approach based on the GH loop of an envelope protein of the foot and mouth disease virus (FMDV) and a combinatorial One Bead One Compound (OBOC) library approach (37). The rational approach has provided successful results which are presented below. Although the library approaches such as OBOC and phage have great potential in identifying many leads, isolating peptides from the display platform (bead or phage) often results in monomers with moderate affinity after detachment requiring further optimizations (34, 38). This was also our experience with OBOC libraries where the leads identified from the screening have considerable optimization remaining before they will match the high affinity and in vivo selectivity of our current A20FMDV2-based peptides.

Figure 20:
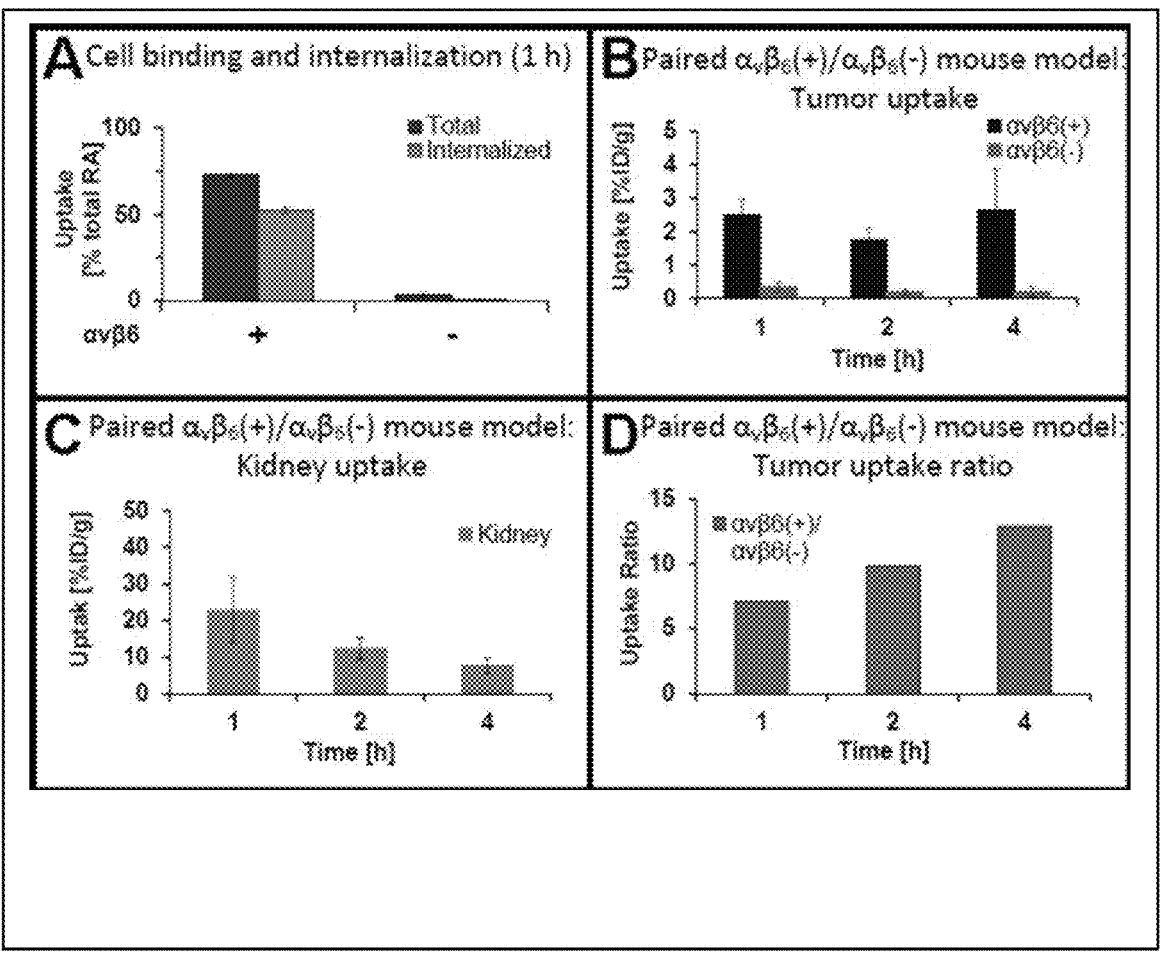
FIG. 20 shows the cell binding, internalization, $\alpha_v\beta_6$ tumor-targeting and kidney clearance of [$^{18}$F]FBA-PEG$_{28}$-A20FMDV2(K16R)-PEG$_{28}$ in a paired $\alpha_v\beta_6(+)/\alpha_v\beta_6(-)$ tumor mouse model.

Data using A20FMDV2-based peptides: The $\alpha_v\beta_6$ integrin is a receptor for fibronectin, tenascin, vitronectin, the latency associated peptide (LAP) of TGFβ and the VP1 coat protein of FMDV. Our first generation $\alpha_v\beta_6$-targeting peptide was A20FMDV2, a 20 amino acid peptide, NAVPNLRGDLQVLAQKVART (SEQ ID NO:5), based on the sequence of the GH-loop of the VP1 protein of FMDV. A20FMDV2 demonstrated high affinity, 3 nM for immobilized $\alpha_v\beta_6$ with at least a 1000-fold selectivity over the other RGD binding integrins (39, 40). We initially demonstrated the promise of A20FMDV2 as an in vivo imaging agent for $\alpha_v\beta_6$ with [$^{18}$F]FBA-A20FMDV2. Although $\alpha_v\beta_6$-specific targeting in vivo was observed, rapid tumor wash out (0.66% ID/g at 1 h, 0.06% ID/g at 4 h) and poor in vivo stability precluded its further application and led to a series of improvements (mainly through the size and locations of PEG and the radiolabeling prosthetic group used) to arrive at the conjugate [$^{18}$F]FBA-PEG$_{28}$-A20FMDV2(K16R)-PEG$_{28}$ (39-44). [$^{18}$F]FBA-PEG$_{28}$-A20FMDV2(K16R)-PEG$_{28}$, a bi-PEGylated peptide featuring a lysine-to-arginine substitution, has $\alpha_v\beta_6$-positive tumor retention of 2.64% ID/g at 4 h, shows preferential renal excretion with kidneys containing <8% ID/g at 4 h, is 90% intact in serum at 2 h and has a $\alpha_v\beta_6$-positive to negative tumor ratio of 12.5:1 at 4 h (FIG. 20). Replacement of the lysine results in the peptide bearing only a single amine group at the N-terminus, thus also permitting site-specific, solution phase radiolabeling with [$^{18}$S]SFB or similar activated esters. Taken together, [$^{18}$F]FBA-PEG$_{28}$-A20FMDV2(K16R)-PEG$_{28}$ demonstrates excellent potential as an $\alpha_v\beta_6$-targeting peptide.

Innovation

The wide prevalence of $\alpha_v\beta_6$ expression and the correlation with the invasive phenotype of cancer, as well as with the negative correlation to patient survival, clearly indicate $\alpha_v\beta_6$ is a particularly attractive target for both disease imaging and therapy. Without any $\alpha_v\beta_6$ specific molecular imaging agents yet having entered the clinic and, to our knowledge, only one antibody-based $\alpha_v\beta_6$ targeted therapy being evaluated (NCT01371305; clinicaltrials.gov, Idiopathic Lung Fibrosis), there is clearly an unmet need for the development of both diagnostic imaging agents and targeted therapeutic strategies. Significant efforts are therefore warranted both toward the development of diagnostic imaging agents as well as novel targeted therapeutics. This example describes the development of novel molecular imaging agents with improved affinities and pharmacokinetics and the development and testing of the efficacy of several novel $\alpha_v\beta_6$-targeted therapeutic strategies, summarized as follows:

1. $\alpha_v\beta_6$-Targeted therapy based on PEG$_{28}$-A20FMDV2(K16R)-PEG$_{28}$ as a delivery vehicle. PEG$_{28}$-A20FMDV2(K16R)-PEG$_{28}$ is used as a carrier for three therapeutic strategies: i) $_D$(KLAKLAK)$_2$ (a pro-apoptotic peptide; (SEQ ID NO:6)); ii) the therapeutic radionuclide $^{90}$Yttrium (β-emitter, energy suitable to treat large tumors); and iii) a micelle-based paclitaxel (PTX) nanocarrier. Efficacy of all three strategies is assessed both in vitro in cell assays and in vivo in mouse models. Positron emission tomography (PET), bioluminescence imaging (BLI) and Cerenkov luminescence imaging (CLI) are used both to track in vivo biodistribution and quantify therapeutic efficacy.

2. Advancing toward first-in-human studies by improving pharmacokinetic properties of PEG$_{28}$-A20FMDV2(K16R)-PEG$_{28}$. Multimerization and/or the addition of a blood albumin binding motif is used to further improve the affinity, in vivo stability, targeting capabilities and clearance behavior of PEG$_{28}$-A20FMDV2(K16R)-PEG$_{28}$. Various covalent prosthetic groups, chelators, and "click" chemistry are used to design the best radiolabeling approach. Overall selection criteria are yields, ease and speed of synthesis, site-specific labeling, affinity and selectivity, and in vivo tumor-targeting-retention and clearance from non-tumor tissues.

Approach

1. $\alpha_v\beta_6$-Targeted Therapy

Rationale: The successful treatment of cancer requires efficient targeted delivery of the therapy, intracellular penetration on targeting and will most likely benefit in the future from the combination of therapies with different mechanisms. The fact that the $\alpha_v\beta_6$ receptor is not expressed in normal adult epithelia suggests it as a good molecular target for therapy (normal adjoining tissue should not be affected). The unique "homing" of the peptide PEG$_{28}$-A20FMDV2(K16R)-PEG$_{28}$ to the $\alpha_v\beta_6$ receptor and its rapid internalization make it an ideal carrier for $\alpha_v\beta_6$-targeted therapy. PEG$_{28}$-A20FMDV2(K16R)-PEG$_{28}$ is used as a carrier for three therapeutics with different mechanisms: delivery of i) $_D$(KLAKLAK)$_2$ (a pro-apoptotic peptide that causes cytotoxicity via disruption of mitochondrial membranes; (SEQ ID NO:6)); ii) the therapeutic radionuclide $^{90}$Yttrium (β-emitter, energy suitable to treat large tumors); and iii) a micelle-based nanocarrier formulation of paclitaxel (PTX, which causes mitotic arrest via aberrant stabilization of microtubules that in turn leads to cell death). Efficacy of all three strategies is assessed both in vitro in cell assays (e.g., WST-1, TUNEL and Caspase 3/7) and in vivo in mouse models (e.g., paired positive and negative subcutaneous xenografts and an antigen positive orthotopic xenograft). Positron emission tomography (PET), bioluminescence imaging (BLI) and Cerenkov luminescence imaging (CLI) are used to both track in vivo biodistribution and measure therapeutic efficacy of these targeted therapies.

Description of models: In vitro studies: DX3/mTFL/ITGB6 and DX3/mTFL (both derived from the parental DX3 melanoma cell line) serve as positive and negative controls for all in vitro assays unless otherwise stated. DX3/mTFL/ITGB6 stably express $\beta_6$ integrin (not expressed in the parental line or DX3/mTFL) under control of a CMV promoter. As $\alpha_v$ integrin (the only integrin capable of heterodimerizing with $\beta_6$) is normally expressed in the DX3 cell line, exogenous expression of $\beta_6$ results in the presence of $\alpha_v\beta_6$ on the cell surface. Mouse models: The paired DX3/mTFL/ITGB6 and DX3/mTFL lines also allow for in vivo examination of $\alpha_v\beta_6$-based selectivity of action of the three therapeutics. As such, a paired DX3/mTFL/ITGB6 and DX3/mTFL xenograft model is used to determine Maximum Tolerated Dose (MTD) and therapeutic effect of all three $PEG_{28}$-A20FMDV2(K16R)-$PEG_{28}$ targeted therapeutics. For MTD studies, non-tumor bearing mice are used to avoid influence on the distribution of the drug, overall health and body weight and rapid growth of tumors confounding interpretation. To establish paired xenografts, anesthetized (isoflurane) mice receive bilateral, subcutaneous (SC) injections of DX3/mTFL/ITGB6 and DX3/mTFL cells ($3\times10^6$ in 100 serum free medium) to the subscapular region. When paired tumors have reached 100-200 mg as determined by caliper measurement and BLI, mice are divided into cohorts as described below. At the conclusion of the paired SC studies, a single lead therapeutic is selected for further analysis in an orthotopic xenograft model using BxPC-3/mTFL (a human pancreatic adenocarcinoma cell line with naturally occurring, elevated ITGB6 expression). BxPC-3/mTFL cells ($1\times10^6$ in 100 μL saline) is injected into the distal pancreas accessed through a subcostal incision. Pressure is held for 1 m to facilitate hemostasis of the puncture site as well as prevent spillage of cell suspension. The surgical incision is then closed with 5-0 nylon sutures or hemoclips, which are removed after one week. Given the rapid elimination of anesthesia, recovery occurs within the first 10 m and mice are continuously observed for 1 h for respiratory activity, skin turgor and movement. Buprenorphine is administered postoperatively and continued every 12 h for a total of 48 h following the procedure. Mice are housed in a vivarium and monitored daily until palpable tumors have developed at which time mice are divided into cohorts as described below. Following the completion of study procedures, all animals are euthanized (cervical dislocation under anesthesia). All cell lines and resulting xenografts express mTFL, a thermostable variant of firefly luciferase, which allows for bioluminescence imaging of resulting tumors for longitudinal studies.

1.1 Selective Targeting of a Pro-Apoptotic Peptide $_D$(KLAKLAK)$_2$ with $PEG_{28}$-A20FMDV2(K16R)-$PEG_{28}$ The 14 amino acid amphipathic peptide $_D$(KLAKLAK)$_2$ (SEQ ID NO:6) was originally described as an antibacterial peptide that disrupts bacterial cell membranes (56). Given the evolutionary similarity of mitochondrial and bacteria membrane structure, when internalized into eukaryotic cells $_D$(KLAKLAK)$_2$ (SEQ ID NO:6) disrupts the mitochondrial membrane which, in turn, triggers apoptosis (57). When conjugated to "homing" peptides $_D$(KLAKLAK)$_2$ (SEQ ID NO:6) has proven success in specifically accumulating in cells and causing cell death (58-60). The efficacy and specificity of a $_D$(KLAKLAK)$_2$ (SEQ ID NO:6) and $PEG_{28}$-A20FMDV2(K16R)-$PEG_{28}$ conjugate is assessed. The unique "homing" to the $\alpha_v\beta_6$ receptor and the rapid internalization of $PEG_{28}$-A20FMDV2(K16R)-$PEG_{28}$ (>70% binding and >50% internalization in $\alpha_v\beta_6$ cells at 1 h) make it an ideal delivery vehicle for $_D$(KLAKLAK)$_2$ (SEQ ID NO:6) (FIG. 20).

In particular embodiments, the $_D$(KLAKLAK)$_2$-GG-$PEG_{28}$-A20FMDV2(K16R)-$PEG_{28}$ (SEQ ID NO:22) conjugate is synthesized using solid phase peptide synthesis (SPPS). In other embodiments, the $_D$(KLAKLAK)$_2$-GG-$PEG_{28}$-A20FMDV2(K16R)-$PEG_{28}$ (SEQ ID NO:22) conjugate can be synthesized using a convergent azide-alkyne Huisgen 1,3-dipolar cycloaddition ("click" reaction) approach between the two peptides. In certain embodiments, a nanoformulation can be used to achieve the desired therapeutic effect, e.g., if $_D$(KLAKLAK)$_2$ (SEQ ID NO:6) alone proves to be toxic.

Figure 21:
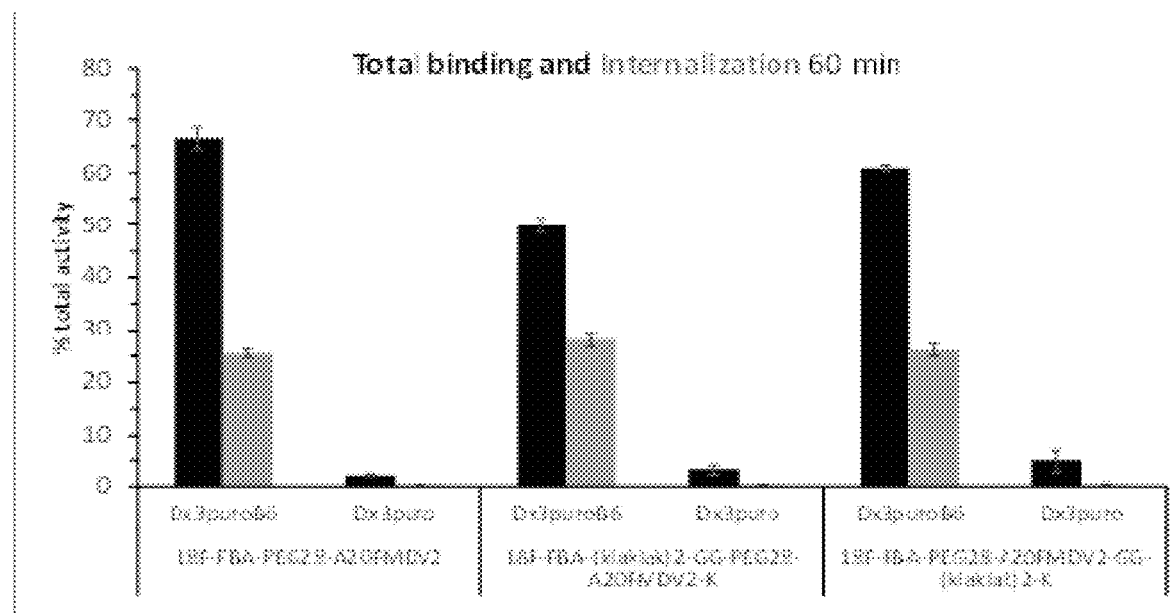
FIG. 21 shows the binding to and internalization into integrin $\alpha_v\beta_6$-expressing DX3puroβ6 cells and the $\alpha_v\beta_6$-negative DX3puro control. Data shown are average (filled bars)±standard deviation (lines) for each radiotracer (n=4/cell line and condition).

1.1.a) Synthesis of $_D$(KLAKLAK)$_2$-GG-$PEG_{28}$-A20FMDV2(K16R)-$PEG_{28}$ Conjugate All peptides used are synthesized manually on Rink-resins using standard Fmoc chemistry. For the $_D$(KLAKLAK)$_2$ (SEQ ID NO:6) and $PEG_{28}$-A20FMDV2(K16R)-$PEG_{28}$ conjugate, a glycine-glycine (GG) linker is incorporated between the two peptides to minimize steric hindrance that might prevent binding and internalization. All peptides are purified using standard RP-HPLC methods and characterized using MALDI-MS. $PEG_{28}$-A20FMDV2-GG-$_D$(KLAKLAK)$_2$-K (SEQ ID NO:23) and $_D$(KLAKLAK)$_2$-GG-$PEG_{28}$-A20FMDV2-K (SEQ ID NO:24) were prepared, characterized, and radiolabeled using [$^{18}$F]FBA and cell binding studies were performed (FIG. 21). The results indicate that conjugation of $_D$(KLAKLAK)$_2$ (SEQ ID NO:6) to $PEG_{28}$-A20FMDV2-$PEG_{28}$ does not affect its affinity, specificity, and internalization-potential towards the integrin $\alpha_v\beta_6$. Serum stability of the peptide conjugate is assessed over a 24 h period. The $_D$(KLAKLAK)$_2$-GG-$PEG_{28}$-A20FMDV2(K16R)-$PEG_{28}$ (SEQ ID NO:22) conjugate is incubated with serum at 37° C., aliquots taken at 1, 2, 4, 12 and 24 h, plasma proteins precipitated with ethanol and supernatant analyzed by HPLC to determine the percentage of intact conjugate.

1.1.b) In Vitro Efficacy of the $_D$(KLAKLAK)$_2$-GG-$PEG_{28}$-A20FMDV2(K16R)-$PEG_{28}$ Conjugate Water soluble tetrazolium (WST-1, Roche) cell proliferation, terminal deoxynucleotidyl transferase dUTP nick end labeling (Click-iT TUNEL, Life Technologies) and Caspase 3/7 (Caspase-Glo, Promega) assays are utilized to determine therapeutic efficacy of $_D$(KLAKLAK)$_2$-GG-$PEG_{28}$-A20FMDV2(K16R)-$PEG_{28}$ (SEQ ID NO:22). Cells cultured on either 96-well plates (WST-1, Caspase 3/7) or 8-well chamber slides (TUNEL assay) are treated with 20 concentrations of $_D$(KLAKLAK)$_2$-GG-$PEG_{28}$-A20FMDV2(K16R)-$PEG_{28}$ (SEQ ID NO:22) ranging from 0-500 μM or matching concentrations of one of the following controls: i) $_D$(KLAKLAK)$_2$ (SEQ ID NO:6) and $PEG_{28}$-A20FMDV2(K16R)-$PEG_{28}$ (SEQ ID NO:21) unconjugated; ii) $_D$(KLAKLAK)$_2$ (SEQ ID NO:6) alone; iii) $PEG_{28}$-A20FMDV2(K16R)-$PEG_{28}$ (SEQ ID NO:21) alone; or iv) vehicle (saline) only. At 2, 6, 24 and 48 h post-treatment, assays are completed according to the manufacturer's recommendations. Non-linear regression analysis of data ise completed using Prism 6.0 software (GraphPad) to determine the half maximal inhibitory concentration (IC50) for conjugate and controls.

1.1.c) Determination of Maximum Tolerated Dose (MTD)

MTD is dependent upon both the delivered therapy and the model in which the study is completed and must be determined empirically for each therapeutic proposed. Non-tumor bearing mice are divided into six cohorts that receive one of a range of concentrations of the $_D$(KLAKLAK)$_2$-GG-$PEG_{28}$-A20FMDV2(K16R)-$PEG_{28}$ (SEQ ID NO:22) conjugate (0, 5, 10, 15, 20 or 25 μg/g) in a single dose via tail vein injection. Animals are then monitored for a period of 30 days for signs of distress, unacceptable side effects or weight loss. At the conclusion of the study, MTD is calculated and this data used to determine the therapeutic dose to be used in the efficacy study described below.

1.1.d) Therapeutic Efficacy of the $_D$(KLAKLAK)$_2$-GG-PEG$_{28}$-A20FMDV2(K16R)-PEG$_{28}$ Conjugate Mice bearing paired DX3/mTFL/ITGB6 and DX3/mTFL-derived xenografts (100-200 mg) are divided into six cohorts and receive a single injection of either the conjugate (Experimental Group #1), $_D$(KLAKLAK)$_2$ (SEQ ID NO:6) and PEG$_{28}$-A20FMDV2(K16R)-PEG$_{28}$ (SEQ ID NO:21) unconjugated (Control Group #1), $_D$(KLAKLAK)$_2$ (SEQ ID NO:6) alone (Control Group #2) PEG$_{28}$-A20FMDV2(K16R)-PEG$_{28}$ (SEQ ID NO:21) alone (Control Group #3) or saline (Control Group #4). At 96 h post-treatment, three mice from each cohort are euthanized and tissue, tumors and organs are reserved for immunohistochemical (IHC) analysis of morphology (H&E) and other indicators of distress/death (caspase-3, TUNEL, etc.). For the remaining mice, tumor sizes are determined twice weekly by BLI. To complete BLI, anesthetized (isoflurane) mice are injected intraperitoneally with D-luciferin (150 mg/kg) 15 minutes prior to image acquisition. Following this uptake period, mice (up to five at a time) are placed on a pre-warmed imaging surface with constant isoflurane. Photographic and luminescence images are acquired with total scan time <1 min. At each imaging time point, animal weights are recorded to ensure that no animals show unacceptable weight loss (greater than 10% animal's weight) following treatment. This schedule is followed for all animals until tumors have reached maximum sizes as defined by the IACUC Policy on Humane Endpoints.

1.2 $\alpha_v\beta_6$-Targeted Radiotherapy with $^{90}$Y-DOTA-PEG$_{28}$-A20FMDV2(K16R)-PEG$_{28}$ Peptides have demonstrated success in the clinic as targeted delivery vehicles for radionuclidic therapy, otherwise known as peptide receptor targeted therapy (PRTT). The most successful reports of PRTT to date have been the use of the somatostatin receptor (SSTR) peptide analogs, $^{90}$Y-DOTA-TOC and $^{177}$Lu-DOTA-TATE to treat patients with neuroendocrine tumors (NET) (66-68). Success of PRTT requires: i) specific targeting of the peptide to deliver an effective radiation dose; ii) good in vivo stability and internalization of the peptide; and iii) appropriate physical properties of the radionuclide. As with $^{111}$In-Octreoscan (the diagnostic agent for SSTR expressing tumors), $\alpha_v\beta_6$-targeted therapies may comprise radiolabeling PEG$_{28}$-A20FMDV2(K16R)-PEG$_{28}$ with a therapeutic radionuclide (69). $^{90}$Y is an exemplary useful radionuclide due to the high energy of the β-particle (2.3 MeV) with a maximum range in tissue of 12 mm (well suited for treating larger tumors) as well as the ability to image the β-emissions using CLI to monitor accumulation at the tumor site. For PRTT, the simultaneous infusion of basic amino acids such as lysine that have been used in patients as kidney-protective agents and successfully reduced nephrotoxcity (70, 71). Multimerization and/or the addition of albumin binding motifs to PEG$_{28}$-A20FMDV2(K16R)-PEG$_{28}$ that have the potential to improve the pharmacokinetic properties of the peptide may also reduce kidney retention. In certain embodiments, the combination of PRTT with both the multiple radionuclide approach as well as a multi-receptor/albumin carrier approach is used. In other embodiments, taking advantage of the different physical properties of $^{90}$Y and $^{177}$Lu allows for the broad targeting in a range of tumor sizes as already demonstrated in NET patients with $^{90}$Y/$^{177}$Lu-DOTA-TATE (72).

1.2.a) Synthesis of $^{90}$Y-DOTA-PEG$_{28}$-A20FMDV2(K16R)-PEG$_{28}$

PEG$_{28}$-A20FMDV2(K16R)-PEG$_{28}$ is labeled with $^{90}$Y using standard methods and DOTA as the chelator. Aqueous ammonium acetate (1M, pH 8.0-8.5) and a solution of the DOTA-PEG$_{28}$-A20FMDV2(K16R)-PEG$_{28}$ (20 nmol) are added to a solution of [$^{90}$Y]Cl$_3$ (1-5 mCi) in 0.05M aqueous hydrochloric acid. The pH is adjusted to 7 to 8 with aqueous ammonium acetate (1M) and the reaction mixture incubated at r.t. for 1 h. DTPA is added to scavenge any remaining free $^{90}$Y$^{3+}$. The $^{90}$Y-DOTA-PEG$_{28}$-A20FMDV2(K16R)-PEG$_{28}$ (SEQ ID NO:25) is purified by C-18 Sep-Pak, formulated in PBS/saline, and analyzed by RP-HPLC.

1.2.b) Cell Binding and Internalization

Cell binding and internalization are assessed using standard methods. 200nCi aliquots of $^{90}$Y-DOTA-PEG$_{28}$-A20FMDV2(K16R)-PEG$_{28}$ (SEQ ID NO:25) is added to cells (3.75×10$^6$ DX3/mTFL/ITGB6 or DX3/mTFL) and incubated for 1 h at r.t. (n=4/cell line). Following centrifugation, the supernatant is removed and the cell pellet washed with 0.5 mL serum free DMEM. The fraction of bound radioactivity is determined with a γ-counter (cell pellet vs. combined supernatants). To determine the fraction of internalized radioactivity, the cells are subsequently treated with acidic wash buffer to release surface-bound activity followed by a wash with PBS. The internalized fraction is determined with a γ-counter (cell pellet vs. radioactivity released into supernatant).

1.2.c) In Vitro Serum Stability

To assess stability, $^{90}$Y-DOTA-PEG$_{28}$-A20FMDV2(K16R)-PEG$_{28}$ (27 µCi) is incubated with serum at 37° C. (or with PBS control), aliquots taken at 0, 4, 24, 48 and 144 h and plasma proteins precipitated with ethanol. The fraction of protein-bound radioactivity is determined with a γ-counter (pellet vs. supernatant) and analytical HPLC of the supernatant performed to determine the percentage of intact $^{90}$Y-DOTA-PEG$_{28}$-A20FMDV2(K16R)-PEG$_{28}$ (SEQ ID NO:25).

1.2.d) In Vitro Efficacy of $^{90}$Y-DOTA-PEG$_{28}$-A20FMDV2(K16R)-PEG$_{28}$

In vitro analysis of $^{90}$Y-DOTA-PEG$_{28}$-A20FMDV2(K16R)-PEG$_{28}$ covers a range of 0-1 per sample and is completed and analyzed as in 1.1.b) above (WST-1, TUNEL and Caspase 3/7 assays). Controls are matching concentrations of [$^{90}$Y]C13 and DOTA-PEG$_{28}$-A20FMDV2-PEG$_{28}$ (SEQ ID NO:26).

1.2.e) Determination of Maximum Tolerated Dose (MTD)

MTD is determined as described in 1.1c) above. Mice bearing paired SC xenografts receive either 0, 5, 8.75, 12.5, 16.25 or 20 µCi/g of $^{90}$Y-DOTA-PEG$_{28}$-A20FMDV2(K16R)-PEG$_{28}$ (SEQ ID NO:25) and monitored as described above. As this radionuclide allows for CLI, images from 0-72 h post-injection (PI) are acquired to non-invasively monitor accumulation and retention of $^{90}$Y-DOTA-PEG$_{28}$-A20FMDV2(K16R)-PEG$_{28}$ (SEQ ID NO:25) at the tumor site. CLI image acquisition procedure is identical to that of BLI (outlined in 1.1.d) above) with a total scan time <15 min.

1.21) Therapeutic Efficacy of $^{90}$Y-DOTA-PEG$_{28}$-A20FMDV2(K16R)-PEG$_{28}$ Efficacy of $^{90}$Y-DOTA-PEG$_{28}$-A20FMDV2(K16R)-PEG$_{28}$ (SEQ ID NO:25) treatment is determined via the method described in 1.1.d) above. Mice bearing paired SC xenografts are divided into two cohorts that receive either $^{90}$Y-DOTA-PEG$_{28}$-A20FMDV2(K16R)-PEG$_{28}$ (MTD) or saline control, each of which is delivered via a single tail vein injection. Mice are imaged and monitored post-treatment as described in 1.1.d) above.

1.3 Targeted Delivery of Paclitaxel Via PEG$_{28}$-A20FMDV2 (K16R)PEG$_{28}$-PEG$^{5K}$CA$_8$ Nanoparticles (NP) show significant promise as delivery vehicles for therapeutics and molecular imaging agents (61). By enhancing the tolerability and/or efficacy of new drugs, nanoparticles are making a significant contribution to clinical outcome. One of the first generation nanomedicines, Abraxane® (albumin stabilized paclitaxel, nab-PTX), was recently FDA approved in combination with Gemcitabine as the first-line treatment for patients with metastatic pancreatic cancer (62). It is likely that many more combination regimes will be approved with improved anti-cancer effects as we strive to treat the myriad of aggressive diseases. As active targeting has shown promise in increasing nanoparticle accumulation at the tumor site when passive targeting is inefficient [reviewed in (63)], an $\alpha_v\beta_6$-targeted-NP is used to deliver the chemotherapeutic, PTX. PEG$_{28}$-A20FMDV2 (K16R)-PEG$_{28}$ (SEQ ID NO:21) is attached to the NP (i.e., the therapy-carrier) as opposed to direct attachment of the peptide to the therapy as described above. The telodendrimer scaffold PEG$^{5K}$CA$_8$, a micelle-based nanocarrier, can be used as a vehicle (NP) and conjugated to the peptide to achieve $\alpha_v\beta_6$-targeted delivery of PTX (64, 65). This nanocarrier system is an amphiphilic linear-dendritic block copolymer that uses three biocompatible building blocks: polyethylene glycol (PEG), L-lysine and cholic acid (CA). PEG$^{5K}$CA$_8$ is soluble in water and self assembles into micelles (21±4 nm) with a high PTX loading capacity (12 mg/mL). In vivo anti-tumor efficacy of PTX-loaded PEG$^{5K}$CA$_8$ was demonstrated in ovarian cancer mouse models with superior toxicity compared to Taxol® and Abraxane®. Combining the advantages of this NP system with the unique "homing" of the peptide PEG$_{28}$-A20FMDV2 (K16R)-PEG$_{28}$ to the $\alpha_v\beta_6$ receptor and its rapid internalization can overcome the active vs. passive challenge. In alternative embodiments, a liposome approach is used. In other embodiments, a multivalent approach using a divalent and/or tetravalent lysine core to add 2 and 4 copies of the peptide to the surface of the NP is used. In further embodiments, a maleimide-thiol approach is used.

Figure 22:
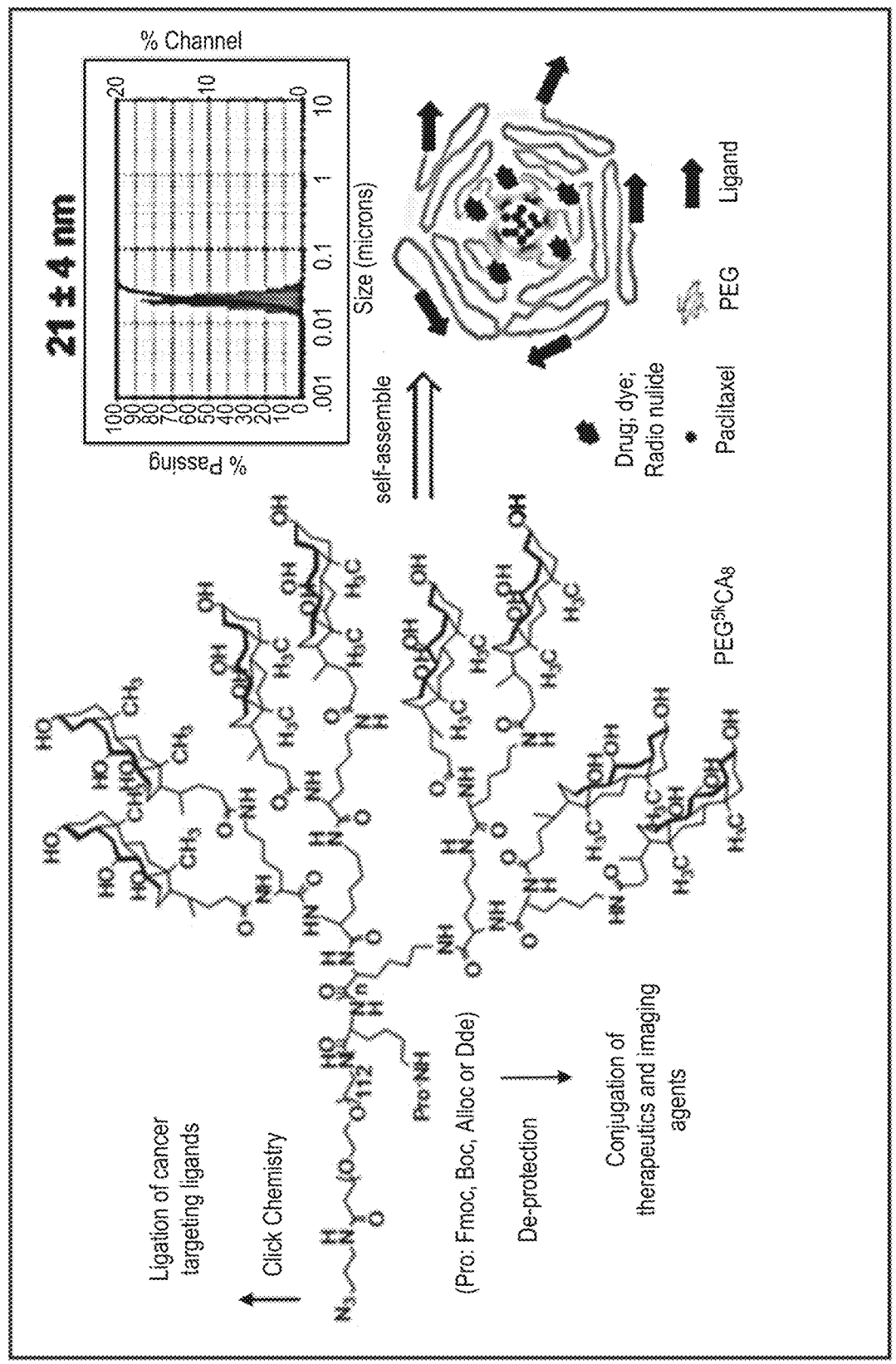
FIG. 22 shows the assembly of a peptide-micelle of the invention.
Figure 23:
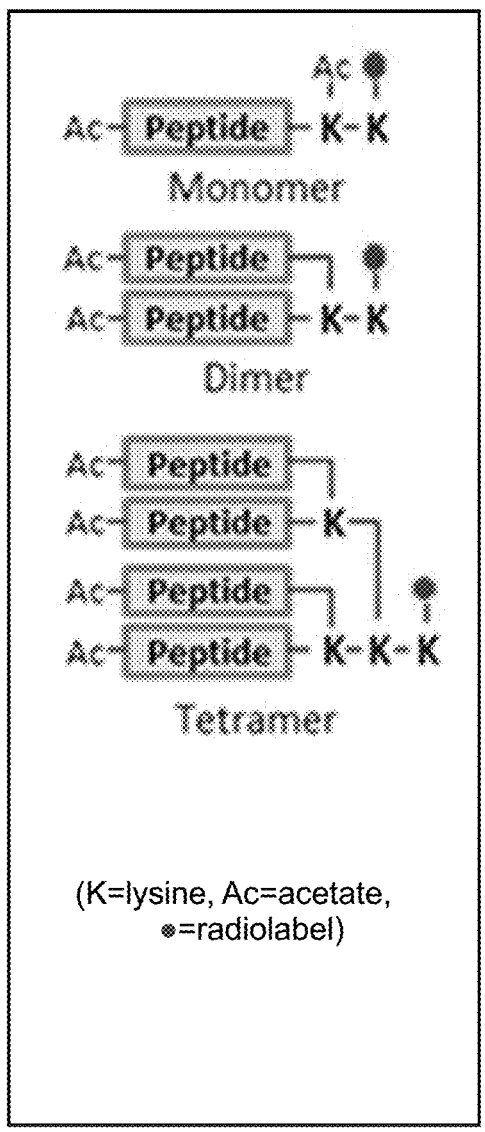
FIG. 23 shows a schematic representation of monomers, dimers, and tetramers of the peptide conjugates of the invention.

1.3.a) Synthesis and Characterization of PEG$_{28}$-A20FMDV2(K16R)PEG$_{28}$-PEG$^{5K}$CA$_8$-PTX N$_3$-PEG$^{5K}$CA$_8$ and alkynyl-PEG$_{28}$-A20FMDV2(K16R)-PEG$_{28}$ (SEQ ID NO:28) are synthesized for ligation via the azide-alkyne Huisgen 1,3-dipolar cycloaddition reaction. N$_3$-PEG$^{5K}$CA$_8$ is synthesized in solution, dialyzed and lyophilized (FIG. 22). Alkynyl-PEG$_{28}$-A20FMDV2(K16R)-PEG$_{28}$ (SEQ ID NO:28) is synthesized using SPPS. The micelles are characterized using TEM. The size and size distribution are measured by dynamic light scattering (DLS). Loading of PTX is performed as previously described (e.g., PTX and PEG$_{28}$-A20FMDV2(K16R) PEG$_{28}$-PEG$^{5K}$CA$_8$ (SEQ ID NO:29) are dissolved in chloroform, dried and subsequently sonicated in PBS buffer solution, unloaded drug precipitants removed by 0.22 μm filtration and loading calculated from RP-HPLC). Serum stability of PEG$_{28}$-A20FMDV2(K16R)PEG$_{28}$-PEG$^{5K}$CA$_8$-PTX (SEQ ID NO:27) is studied as described in 1.1.a) above and PTX release is assessed using dialysis and RP-HPLC.

1.3.b) In Vitro Efficacy of PEG$_{28}$-A20FMDV2(K16R) PEG$_{28}$-PEG$^{5K}$CA$_8$-PTX In vitro analysis of PEG$_{28}$-A20FMDV2(K16R)PEG$_{28}$-PEG$^{5K}$CA$_8$-PTX (SEQ ID NO:27) covers concentrations ranging from 0-25 ng/mL and is completed and analyzed as described in 1.1.b) above (e.g., WST-1, TUNEL and Caspase 3/7 assays). Control treatments are matching concentrations of three controls: i) PEG$_{28}$-A20FMDV2(K16R)PEG$_{28}$-PEG$^{5K}$CA$_8$(SEQ ID NO:29); ii) PEG$^{5K}$CA$_8$-PTX; and iii) PEG$^{5K}$CA$_8$.

1.3.c) Determination of Maximum Tolerated Dose (MTD)

MTD is determined as described in SA 1.1.c) above. Non-tumor bearing mice are divided into six cohorts that receive either 0, 12, 24, 36, 48 or 60 μg/g PEG$_{28}$-A20FMDV2(K16R)-PEG$_{28}$-PEG$^{5K}$CA$_8$-PTX and monitored as described previously.

1.3.d) Therapeutic Efficacy of PEG$_{28}$-A20FMDV2 (K16R)PEG$_{28}$-PEG$^{5K}$CA$_8$-PTX Efficacy of PEG$_{28}$-A20FMDV2(K16R)PEG$_{28}$-PEG$^{5K}$CA$_8$-PTX treatment is determined via the method described in 1.1.d) above. Mice bearing paired SC xenografts are divided into five cohorts that receive either PEG$_{28}$-A20FMDV2(K16R)PEG$_{28}$-PEG$^{5K}$CA$_8$-PTX (Experimental Group #1), PEG$_{28}$-A20FMDV2(K16R)PEG$_{28}$-PEG$^{5K}$CA$_8$ (Control Group #1), PEG$^{5K}$CA$_8$-PTX (Control Group #2), PEG$^{5K}$CA$_8$ (Control Group #3), or saline (Control Group #4). Mice are imaged and monitored post-treatment as described in 1.1.d) above.

1.4 Therapeutic Efficacy of Lead Therapeutic in an Orthotopic Model of Pancreatic Cancer Following conclusion of MTD and subcutaneous xenograft studies, a single lead compound is selected based on highest fraction of tumor regression/non-progression (based statistical analysis) for further analysis within the BxPC-3/mTFL orthotopic model. With this model, lesions develop within their normal microenvironment. Additionally, delivery of the therapeutic to the tumor site in this model can more accurately confirm desired pharmacokinetics. Mice bearing orthotopic BxPC-3/mTFL tumors are divided into four cohorts that receive one of three doses of targeted therapeutic (e.g., 0.25×, 0.5× or 1×MTD) or saline control. Analysis of therapeutic effect and all post-treatment monitoring of mice are completed as described in 1.1.d) above.

1.5 Statistical Analysis

Therapeutic effect can be determined primarily by reduction of tumor size/growth rate and survival of animals. The first analytic goal is to estimate the Maximum Tolerated Dose (MTD) for each candidate therapeutic, defined as the highest dose with no more than 10% of animals experiencing a dose-limiting toxicity (DLT). We can fit logit-linear quantal dose-response models to the number of mice experiencing DLT and estimate the MTD-10% by calibration, with 95% confidence intervals calculated by a modified Fieller's theorem approach. If no DLTs are observed, we can estimate an upper bound on the probability of a DLT across the range of 5 doses, to obtain a lower bound on the MTD. The second analytic goal is to assess the efficacy of the targeted peptide radiolabeled with $^{90}$Y or conjugated with $_D$(KLAKLAK)$_2$ (SEQ ID NO:6) or PEG$^{5K}$CA$_8$ compared with appropriate controls in a within-mouse paired tumor model (target-positive and target-negative). The primary outcome can be tumor growth rate, measured twice weekly by BLI. We can fit mixed-effect repeated measures growth curve regression models, comparing the growth rate under active treatment to the anticipated linear growth in saline-treated tumors, using a structured regression coefficient approach. The primary comparison can be between the conjugated/radiolabeled treatment of target-positive tumors and untreated target-positive tumors; secondary comparisons can assess the effect of appropriate controls and the difference in effects on target-positive vs. target-negative tumors. Assuming linear tumor growth in untreated animals with a range of ±50% of the mean, two-sided tests at α=0.05 have at least 85% power to detect a two-thirds reduction in the growth rate using the conjugated/radiolabeled forms of the experimental therapeutic, a clinically meaningful improvement. Models can be validated graphically and analytically and alternatives considered (nonlinear fits, transformations) if the assumptions are violated.

2. Advancing Toward First in-Human Studies by Improving Pharmacokinetic Properties of $PEG_{28}$-A20FMDV2(K16R)-$PEG_{28}$ The high affinity and selectivity of $PEG_{28}$-A20FMDV2 (K16R)-$PEG_{28}$ for the $\alpha_v\beta_6$ receptor has been demonstrated both in vitro (ELISA and cell binding) and in vivo (small animal PET imaging) as described herein. This peptide conjugate possesses particularly favorable targeting and pharmacokinetic properties. As described in this section, further improvements can be made to this peptide with respect to its affinity as well as in vivo pharmacokinetics and circulation time. For example, the use of multimerization and/or addition of a non-covalent blood albumin binding motif can further improve the affinity, in vivo performance, and targeting capabilities. Various covalent prosthetic groups, chelators, and "click" chemistry can be interrogated to design the best approach to radiolabel the peptide.

2.1 A Multimeric Approach

Compared to monomeric peptides, multimeric derivatives have exhibited greatly enhanced target affinity for cell surface receptors. Particularly, non-linear improvement in affinity is often observed when transitioning from monomeric peptide to dimeric and tetrameric peptides, resulting in more than doubling/quadrupling of affinities (34). The additional benefit is believed to be avidity-based, derived from synergistic (multivalent) interaction of the multimer-subunits with multiple cell surface receptors. This would likely induce structural reorganization of the cell surface receptors, resulting in increased binding through formation of focal adhesion hotspots. This multivalency-based affinity-boost has been documented most thoroughly for targeted in vivo imaging of a related integrin, $\alpha_v\beta_3$, with cyclo(RGD) peptides (45-47). Key parameters for success were: i) the target-affinity and selectivity of the starting monomer; and ii) the size of the multimer (number of monomers and length of linkers between them—with longer linkers facilitating polyvalent binding). Also, a recent preliminary report has shown similar positive effects for a linear $\alpha_v\beta_6$-targeting peptide, $^{64}$Cu-M10, where tumor-uptake increased by as much as nearly 3-fold for the dimeric $^{64}$Cu-$(M10)_2$ at early time points (0.55 to 1.6% ID/g at 1 h) (34). Of note, by comparison, our current monomer lead compound (i.e., $PEG_{28}$-A20FMDV2(K16R)-$PEG_{28}$) has tumor binding at 1 h of 2.51% ID/g and remains constant over 4 hours. The evaluation of affinity-enhancement for the $\alpha_v\beta_6$ receptor in vitro and in vivo through multimerization of $PEG_{28}$-A20FMDV2(K16R)-$PEG_{28}$-derived peptides is therefore a significant step for both molecular imaging and therapy as outlined in above. In alternative embodiments, different length PEG-linkers (e.g., $PEG_5$, $PEG_{11}$) and head-to-tail multimerization (e.g., using solution-phase click chemistry) can be used to determine avidity-effects.

2.1.a) Synthesis

Monomeric, dimeric, and tetrameric peptides and their radiolabeled analogs can be prepared (FIG. 23). Steric crowding is minimized by the C-terminal $PEG_{28}$-spacers connecting to the branching lysine. All peptides are synthesized on Rink-resins using standard Fmoc chemistry. Following a β-alanine spacer, a Lys(Alloc) residue is introduced for site-specific radiolabeling at the end of the peptide synthesis after deprotection with $Pd(PPh_3)_4$ ("Pd"). Branching is achieved through use of Fmoc-Lys(Fmoc)-OH, either once (for dimers) or twice (for tetramers; see FIG. 23); for the monomer a Fmoc-Lys(ivDde)-OH is used, that, after selective deprotection with hydrazine, is capped with acetate (using acetic anhydride) to provide a control with a C-terminus equivalent to that of the multimers. The remaining peptide assembly uses Fmoc-amino acids and Fmoc-$PEG_{28}$-COOH and acetic anhydride (for terminal capping), with reagent equivalents adjusted for the multimers.

2.1.b) Radiolabeling Approaches

In certain instances, the prosthetic group used for radiolabeling the peptide can affect the overall pharmacokinetics. As such, the labeling approach (covalent vs. chelator-based) is not biased, but rather a modular strategy is presented that facilitates radiolabeling with radioisotopes including $^{18}$F, $^{64}$Cu, and $^{90}$Y. Established methods are utilized, including a solid-phase radiolabeling approach using 4-[$^{18}$F]fluorobenzoic acid ([$^{18}$F]FBA) (48). Once in vitro and in vivo stability, affinity and selectivity of the $^{18}$F-radiolabeled peptides for the $\alpha_v\beta_6$ receptor are established, should longer radioactive half-lives be required because of increased in vivo circulation or retention in the target, alternative radioisotopes and strategies can be used. In certain embodiments, reliable metal chelators such as DOTA, NOTA, and NOTA-TCO (TCO=trans-cyclooctene) are used for longer-lived radioisotopes. For metal radiolabeling, $DOTA(OtBu)_3$-COOH or $NOTA(OtBu)_2$-COOH are coupled, followed by TFA cleavage, HPLC purification, and metal chelation in solution.

2.1.c) In Vitro Analysis (Competitive ELISA)

Competitive ELISA can be used to determine affinity and selectivity for purified integrin $\alpha_v\beta_6$. Integrin $\alpha_v\beta_3$ can be used in parallel as control to determine selectivity. The integrin is captured on a 96-well plate ($\alpha_v$-capturing antibody P2W7). For the competition experiment triplicate wells are coated with equal volumes biotinylated fibronectin (BtFn; biotinylated natural ligand for $\alpha_v\beta_6$) or vitronectin (BtVn; for $\alpha_v\beta_3$) and a serial dilution of peptide (non-radioactive analog; stock: 2 mM; final concentration range 10 pM to 100 μM) for 1 h. Controls: i) no peptide, ii) no peptide and no antibody, iii) no peptide and no Bt-ligand. Bound BtFn (or BtVn) is detected by addition of ExtrAvidin-Horseradish peroxidase, followed by tetramethylbenzidine (TMB) solution. The reaction is terminated with 1N sulfuric acid and absorbance measured at 450 nm. $IC_{50}$-values determined by plotting %-Bt ligand bound vs. peptide concentration. All compounds with $IC_{50}$<5 nM and selectivity of >1000-fold for $\alpha_v\beta_6$ over $\alpha_v\beta_3$ can move forward to cell binding studies. This approach allows for the identification of $\alpha_v\beta_6$-specific targeting peptides and eliminates those that bind to other closely related members of the integrin family such as $\alpha_v\beta_3$. Using this strategy, A20FMDV2 demonstrated high affinity (e.g., 3 nM) for immobilized $\alpha_v\beta_6$, with at least a 1000-fold selectivity over the other RGD binding integrins (40).

Description of models. In vitro studies: DX3/mTFL/ITGB6 and DX3/mTFL (both derived from the parental DX3 melanoma cell line and equivalent to DX3puroβ6 and DX3puro, respectively, with additional expression of mTFL, a thermostable variant of firefly luciferase, which allows for bioluminescence imaging [BLI] of tumors in animal studies) serve as positive and negative controls, respectively, for all in vitro assays unless otherwise stated. DX3/mTFL/ITGB6 stably express $\beta_6$ integrin under control of a CMV promoter. As $\alpha_v$ integrin (the only integrin capable of heterodimerizing with $\beta_6$) is normally expressed in the DX3 cell line, exogenous expression of $\beta_6$ results in the presence of $\alpha_v\beta_6$ on the cell surface. The integrin $\alpha_v\beta_6$ is not expressed in the DX3/mTFL (or the parental line), and both cell lines express $\alpha_v\beta_3$, $\alpha_v\beta_5$ and $\alpha_5\beta_6$, and other closely related members of the integrin family. Mouse models: The paired DX3/mTFL/ITGB6 and DX3/mTFL lines allow for in vivo examination of $\alpha_v\beta_6$-based selectivity of both the radiolabeled peptides and the potential therapeutics described above. To establish paired xenografts, anesthetized (isoflurane) mice receive bilateral, subcutaneous (SC) injections of DX3/mTFL/ITGB6 and DX3/mTFL cells ($3\times10^6$ in 100 µL serum free medium) subscapular. When paired tumors have reached 100-200 mg as determined by palpation, mice are used for either imaging or therapy studies.

2.1.d) In Vitro Analysis (Cell Binding)

Cell binding can be assessed for each radiolabeled peptide using DX3/mTFL/ITGB6 and DX3/mTFL as described above. Aliquots of the radiolabeled peptide can be incubated with a cell suspension (e.g., $3.75\times10^6$ cells/100 µl; n=4/cell line) for 1 h. Previous studies demonstrated that cell binding occurred rapidly, within the first 30 mins (39). Following centrifugation, supernatant is removed and the cell pellet washed with 0.5 mL SF-DMEM. The fraction of bound radioactivity is determined with a γ-counter. To determine the fraction of internalized radioactivity, the cells are subsequently treated with acidic wash buffer to release surface-bound activity and measured in a γ-counter. All radiolabeled peptides with >50% binding and >40% internalization and with 10-fold selectivity for DX3/mTFL/ITGB6 can move forward to serum stability studies.

2.1.e) In Vitro Analysis (Serum Stability)

Serum stability for each radiolabeled peptide can be assessed over a time period of 2 h ($^{18}$F) or 24 h ($^{64}$Cu) by incubation with serum at 37° C. (control: in PBS). Aliquots can be taken at 0.5, 1, 2 h ($^{64}$Cu: also 4, 12 and 24 h), plasma proteins precipitated with ethanol and the supernatant analyzed by HPLC to determine the percentage of intact radiolabeled peptides. All radiolabeled peptides that are >95% intact after 2 hours and meet all the above cell-binding criteria can move forward to in vivo studies.

2.1.f) Small Animal PET/CT Imaging

The paired DX3/mTFL/ITGB6 and DX3/mTFL xenograft model is described above. For each radiolabeled peptide, when tumors have reached 100-200 mg the animals are used for imaging (PET/CT) and biodistribution studies following IACUC approved protocols. For imaging studies, the radiolabeled peptides (approx. 200 µCi) are delivered via tail vein injection in anesthetized mice (isoflurane) and mice are imaged (e.g., $^{18}$F: 0-1, 2, 4 h; $^{64}$Cu: 1, 4, 24 h). Each emission scan can be accompanied by a transmission scan (for attenuation correction) and a CT scan (for anatomical reference). Image data can be binned, reconstructed, co-registered, and analyzed by drawing regions of interest (RoIs) around tumors and organs of interest (kidney, bladder, liver, heart, muscle) based on the CT reference data, and plotted as time-activity-curves. For biodistribution studies, the radiolabeled peptides (approx. 20 µCi) are injected as described above. Tissues, organs, and tumors are collected rapidly (e.g., time points for $^{18}$F: 1, 2, 4 h; $^{64}$Cu: 1, 4, 24 h), rinsed with PBS, and radioactivity measured in a γ-counter. Calibrated, decay-corrected radioactivity concentrations can be expressed as percent of injected dose per gram of sample (% ID/g). Additionally, for blocking experiments, the demonstrated $\alpha_v\beta_6$-targeting peptide [$^{19}$F]FBA-PEG$_{28}$-A20FMDV2 can be injected i.v. (30 mg/kg, 10 mg/ml in saline) ten minutes before the radiotracer; dissection and analysis can be done at the 1 h time point as described above. For evaluation of tracer stability in vivo, tumor, kidney, and urine samples are analyzed. To assess stability in tumor and kidney the radiolabeled peptides can be injected as described above. The $\alpha_v\beta_6$-positive tumor and kidneys can be harvested (1 h) and homogenized in PBS. Proteins are precipitated with ethanol, radioactivity measured and the supernatant analyzed by HPLC to determine the percentage of intact radiolabeled peptides. When available, excess urine is collected during biodistribution studies for HPLC analysis. Additionally, two sets of tumors can be embedded in freezing medium and sectioned immediately (20 µm for autoradiography, 5 µm for IHC, alternating). Autoradiography samples are exposed to a storage phosphor-screen overnight and read using a phosphorimager. IHC can be done once the radioactivity has decayed; sections are fixed (formaldehyde), blocked (3% aq. H2O2), incubated with the anti-integrin (36 antibody and peroxidase-labeled secondary antibody, followed by development with 3-amino-9-ethylcarbazole (AEC) and counterstaining with Mayer's Hematoxylin.

2.2 Albumin Binding Motifs to Improve In Vivo Pharmacokinetics

Figure 24:
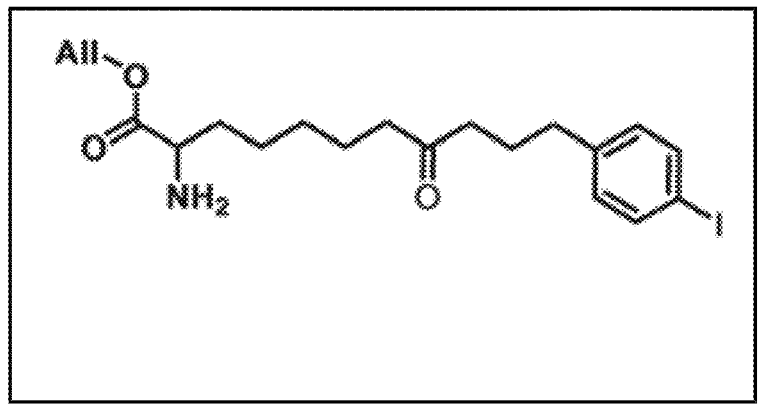
FIG. 24 shows an exemplary allyl protected albumin binder.
Figure 25:
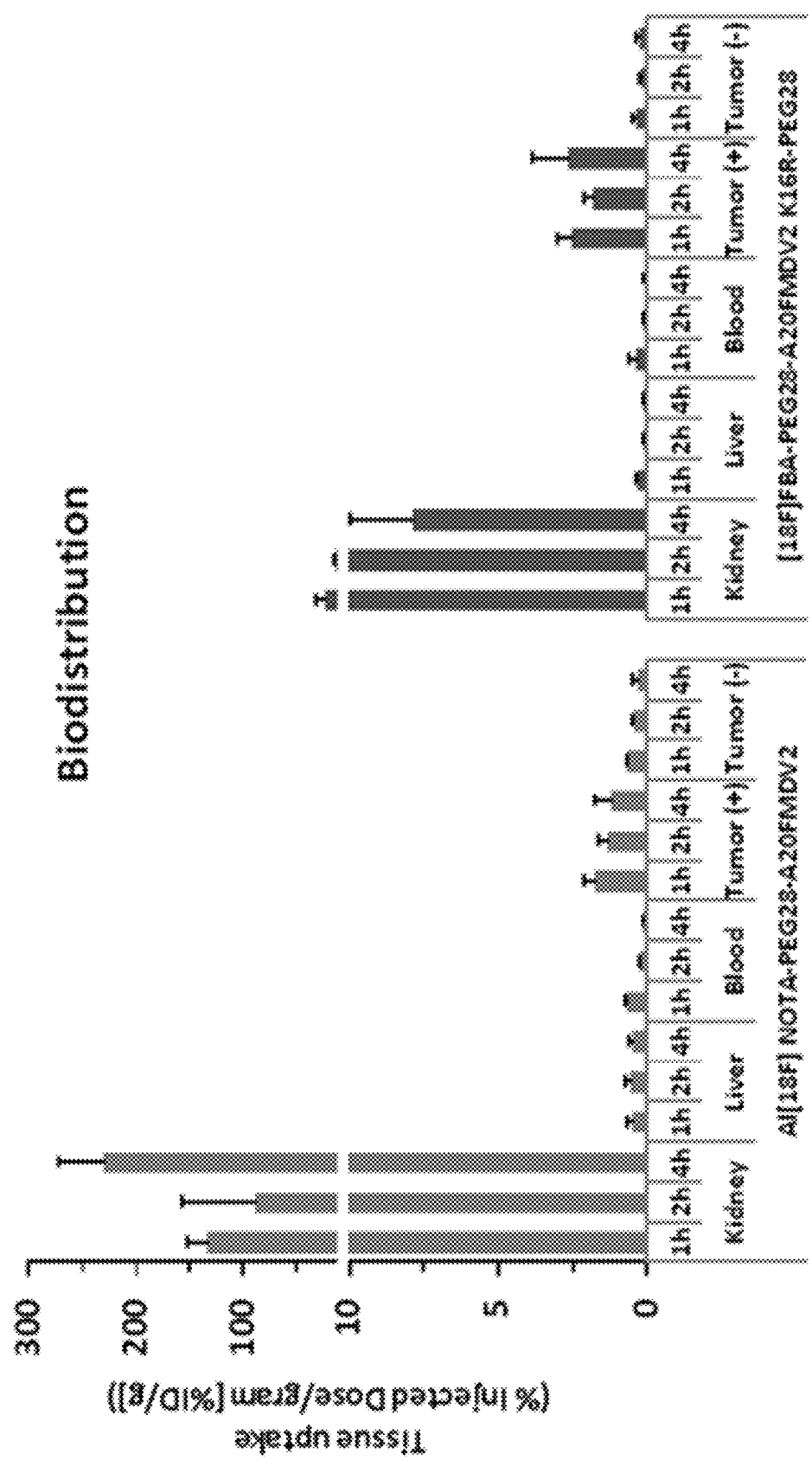
FIG. 25 shows the biodistribution data for Al[$^{18}$F] NOTA-PEG$_{28}$-A20FMDV2 and [$^{18}$F]FBA-PEG$_{28}$-A20FMDV2 (K16R)-PEG$_{28}$ at 1, 2, and 4 h post-injection (p.i.) in a paired $\alpha_v\beta_6(+)/\alpha_v\beta_6(-)$ tumor mouse model.

One drawback of the application of "homing" peptides for tumor targeting is their short in vivo half-life. Previous efforts to increase the half-life included the covalent attachment to carrier molecules such as purified albumin before administration (49, 50). Other non-covalent approaches have also been investigated; Dennis et al. described the non-covalent interaction between albumin and an antibody fragment conjugated to an albumin binding peptide (51). Here, the pharmacokinetic benefits are realized by the non-covalent interaction of the radiotracer with the albumin present in the bloodstream. In this approach not only was an increase in tumor uptake of the fragment observed but also no kidney retention. Most recently, a 4-(4-iodophenyl)butyric acid-based small molecule discovered by screening a DNA-encoded chemical library that binds HSA, was used to facilitate the first targeting of the folic acid receptor using a small folic acid conjugate (52). As described in the study by Schibli et al., when this albumin binder (FIG. 24) was conjugated to $^{177}$Lu-labeled folic acid, high tumor uptake and significantly reduced renal accumulation was observed (53, 54). This non-covalent approach can be used to improve the blood half-life of PEG$_{28}$-A20FMDV2(K16R)-PEG$_{28}$ and other analogs. The chelator-based approach to radiolabeling offers the greatest flexibility with respect to choice of radioisotope as well as ease of final purification. Additionally, the formal charge of the prosthetic-group radiolabel, believed to play a role in renal trapping, can be modified by choosing chelators with different numbers of negative charges (e.g., DOTA, NOTA, CB-TE2A). In addition to increasing the circulation time of the peptide, this approach also has the potential to reduce the problematic kidney retention observed with radiolabeled-chelate-analogs. Al[$^{18}$F]-NOTA-PEG$_{28}$-A20FMDV2 showed kidney uptake at 4 h of 229% ID/g vs. [$^{18}$F]FBA-PEG$_{28}$-A20FMDV2(K16R)-PEG$_{28}$ which at 4 h was only 7.87% ID/g (FIG. 25).

In certain instances, the iodine in 4-(4-iodophenyl)butyric acid is replaced with groups such as methyl or bromine, and/or the alkyl chain is shortened, as the affinity of the albumin binder to albumin has been shown to be fine-tunable. In other instances, a mono-cysteine modification of the peptide is introduced as single cysteine residues have been shown to form a temporary disulfide bond with Cys34 of albumin, aiding in tumor targeting of peptide tracers (55).

2.2.a) Synthesis

Figure 26:
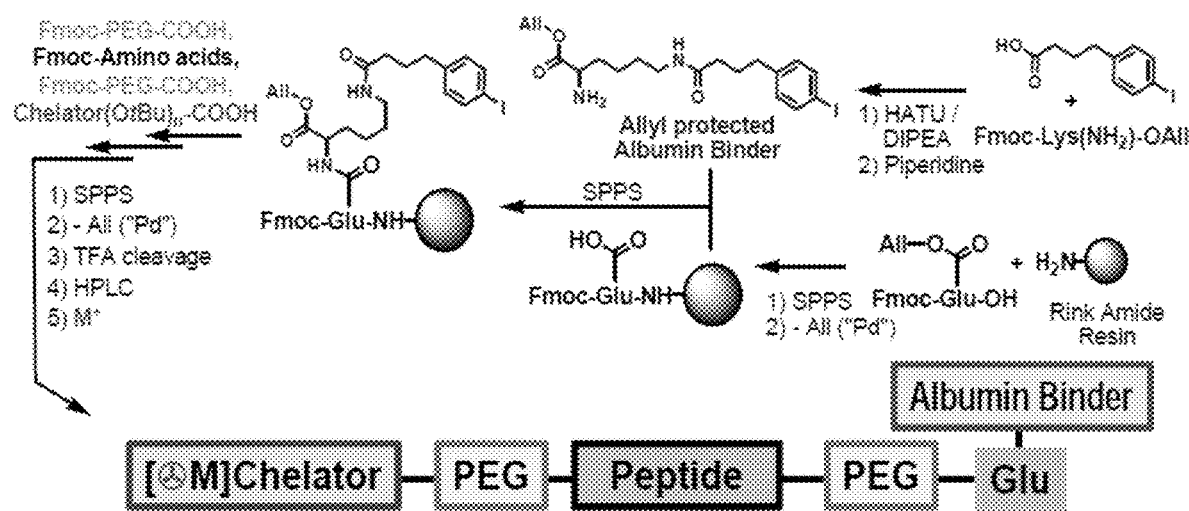
FIG. 26 is Scheme 1 showing the stepwise assembly of radiolabeled-albumin binder modified peptide. Shown is a scheme for a chelator-binding peptide. For solid-phase radiolabeling (e.g., with [$^{18}$F]FBA), the prosthetic group can be coupled to the free N-terminus prior to TFA cleavage and radio-HPLC purification.
Figure 27:
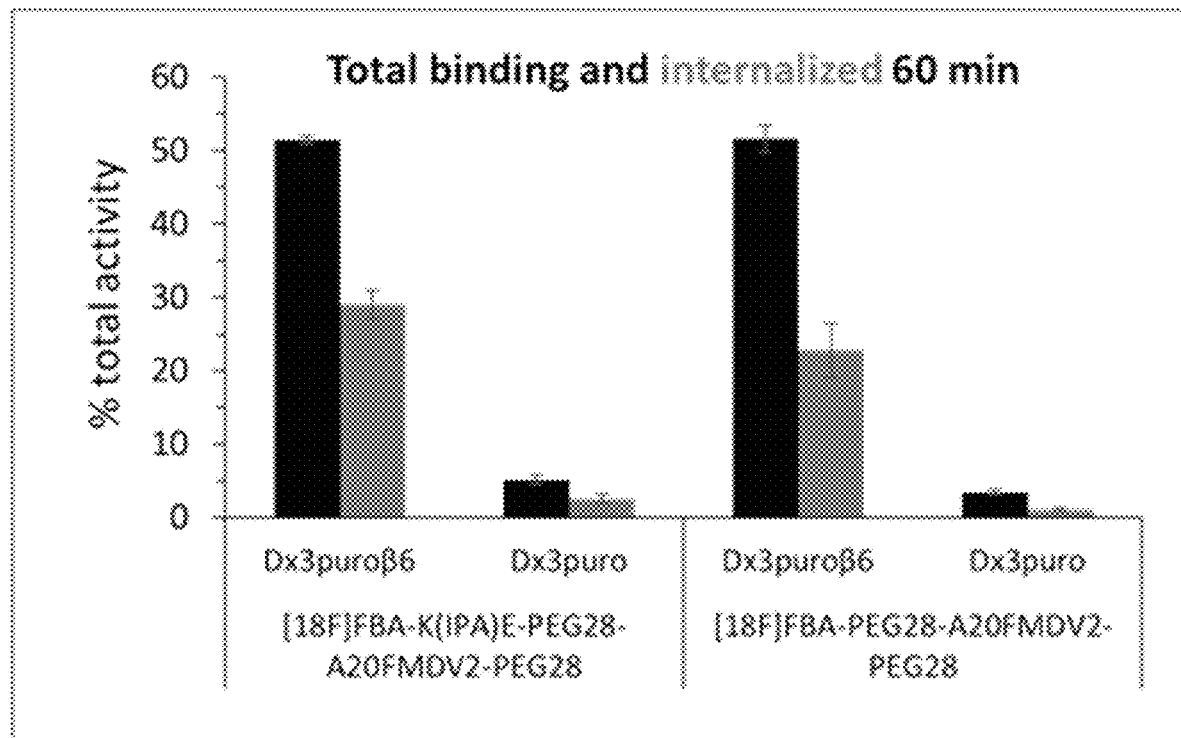
FIG. 27 shows the binding to and internalization into integrin $\alpha_v\beta_6$-expressing DX3puroβ6 cells and the $\alpha_v\beta_6$-negative DX3puro control. Data shown are average (filled bars)±standard deviation (lines) for each radiotracer (n=4/cell line and condition).
Figure 28:
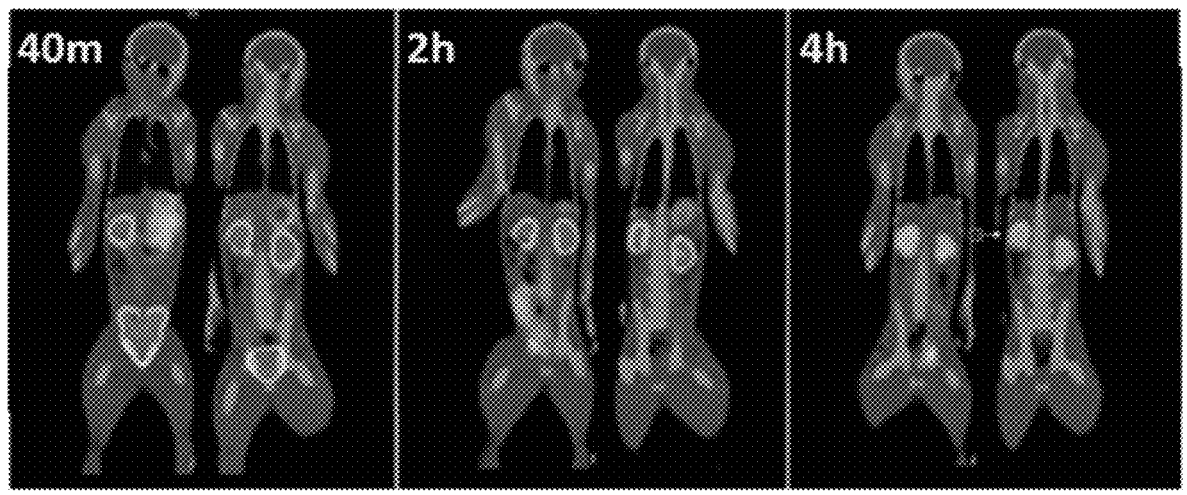
FIG. 28 shows confocal PET/CT images of scans obtained with [$^{18}$F]FBA-PEG$_{28}$-A20FMDV2(K16R)-PEG$_{28}$ in healthy rhesus monkeys. Animals were imaged side-by-side in the supine position at designated times post-injection (p.i.).

The albumin binder can be assembled using Fmoc chemistry (Scheme 1 in FIG. 26) from 4-(4-iodophenyl)butyric acid (IPA) and Fmoc-Lys-OAll. Following Fmoc removal, the allyl protected albumin binder (FIG. 24) can be coupled to the side-chain of the first amino acid (Fmoc-Glu(OH)—) on solid phase, followed by standard peptide assembly. (The allyl-protection can be removed from the albumin binder prior to the trifluoroacetic acid (TFA) cleavage). For radio-metal labeling, chelators (DOTA, NOTA) are introduced as mono-unprotected acids, followed by acids, followed by cleavage, HPLC purification and solution-phase radiolabeling (Scheme 1 in FIG. 26). For solid phase-radiolabeling (e.g., with [$^{18}$F]FBA), the prosthetic group can be coupled to the free N-terminus (instead of the chelator) prior to cleavage, followed by radio-HPLC purification.

Studies with an albumin-binding group, termed K(IPA)E (i.e., ε-(4-(4-iodophenyl)butyl amide)lysine-glutamic acid), introduced on the N-terminus of the bi-terminally PEGylated A20FMDV2 peptide (i.e., FBA-K(IPA)E-PEG$_{28}$-NAVPNLRGDLQVLAQKVART-PEG$_{28}$; SEQ ID NO:30) showed (in ELISA) high affinity for the target (IC$_{50}$=1 nM), comparable to that of PEGylated A20FMDV2 not bearing K(IPA)E (IC50=2 nM). Target specificity and selectivity were also shown in cell-based binding and internalization assays using integrin $\alpha_v\beta_6$-expressing DX3puroβ6 cells and the $\alpha_v\beta_6$-negative DX3puro control (FIG. 27). Both the K(IPA)E-bearing radiotracer and its K(IPA)E-free control bound at 52% to DX3puroβ6 cells; 56% of bound radioactivity was internalized for the K(IPA)E bearing radiotracer (vs 44% of the control). By comparison, binding and internalization for both radiotracers was low in the $\alpha_v\beta_6$-negative DX3puro control.

2.2.b) In Vitro Analysis (Protein Binding Assay)

An ultrafiltration assay is used to determine the binding of the radiolabeled-albumin binder-peptide using previously described methods. Centrifree ultrafiltration devices can be used to separate free radiolabeled peptide from the plasma albumin-bound fraction at the end of the incubation period. Filtrates can be measured in a γ-counter and percent binding determined. Size-exclusion HPLC can be done on blood plasma samples incubated with the peptide (37° C.; 5, 15, 30, 60 m) to assess binding kinetics. All other in vitro and in vivo screening may proceed as described in Sections 1.2.b), 1.2.c) and 2.1 above.

2.2.c) Non-Human Primate Studies

The impact of multimerization and the addition of the albumin binding motif can be clearly quantified in vitro and in vivo and compounds that have high affinity (e.g., <1 nM), good selectivity for $\alpha_v\beta_6$ (e.g., over 1000 times higher affinity over other integrins) along with good in vivo behavior and significantly improved in vivo stability can be identified. Other criteria such as total tumor uptake, rapid clearance from organs such as kidneys, speed of synthesis, simplicity, site-specific labeling, radiochemical yields and specific activities can be taken into consideration for further selection of compounds to be advanced for further evaluation in non-human primates (NHP) such as rhesus monkeys. In order to assess the biodistribution and safety of the optimized peptides, NHP studies can be performed. NHP provide the necessary and predictive translational and preclinical models because of reproductive, developmental, physiologic, genetic, and immunologic similarities when compared to humans. For these studies, 2 lead peptides identified based on $\alpha_v\beta_6$-affinity and selectivity can be selected, and in vivo $\alpha_v\beta_6$ (+)-tumor-targeting and retention and clearance from non-tumor tissues can be assessed in 4 rhesus monkeys (2 males and 2 females) using established techniques. Four rhesus monkeys (*Macaca mulatta*) are included as two pairs (one male, one female each) for each of the peptides tested after extensive studies in mice. This approach allows the study of male/female pairs simultaneously, eliminating confounding variables while conserving animal numbers. These studies also allow animals to be imaged simultaneously.

Whole body dosimetry can be determined. Animals are fasted overnight, then sedated with telazol/ketamine for these procedures using standardized protocols. They are placed supine on the PET/CT scanning bed, injected with the radiolabeled peptide intravenously (IV) (both injected simultaneously) and imaged for 30 min, then repeated at 2 and 4 h p.i. Blood (peripheral vessel; ~2 ml) and urine samples (ultrasound-guided cystocentesis; ~1 mL) are collected at each time point for HPLC analysis. Oxygen saturation is monitored with a pulse oximeter during the imaging and a circulating water-heated pad used to maintain body temperature. After imaging, the animals are placed in a designated metabolism room for radioactive monitoring, and then returned to their regular housing once cleared. Chosen from the wealth of murine and primate data generated, the lead imaging agent can be selected to strike the most favorable balance of $\alpha_v\beta_6$-targeted tumor uptake and retention (mouse model) and favorable overall pharmacokinetics, notably renal clearance (primate imaging). FIG. 28 shows coronal PET/CT images of scans of [$^{18}$F]FBA-PEG$_{28}$-A20FMDV2(K16R)-PEG$_{28}$ in healthy rhesus monkeys.

Summary

This example demonstrates the design, synthesis, and evaluation of novel $\alpha_v\beta_6$ integrin-targeting molecular imaging agents and therapeutic strategies. The prevalence of this receptor on cancers, its association with metastatic potential and negative correlation to patient survival and the increasing reports in the literature citing $\alpha_v\beta_6$ as a target for imaging and therapy make these novel molecular imaging agents and therapeutic strategies timely and highly clinically relevant.

REFERENCES

1. Ahmed et al., Alpha(v)beta(6) integrin-A marker for the malignant potential of epithelial ovarian cancer. The journal of histochemistry and cytochemistry. 2002; 50(10): 1371-80.
2. Elayadi et al., A peptide selected by biopanning identifies the integrin alphavbeta6 as a prognostic biomarker for nonsmall cell lung cancer. Cancer research. 2007; 67(12): 5889-95.
3. Liu et al., Integrin alphavbeta6 as a novel marker for diagnosis and metastatic potential of thyroid carcinoma. Head & neck oncology. 2013; 5(1):7.
4. Jones et al., ADAM 10 is over expressed in oral squamous cell carcinoma and contributes to invasive behaviour through a functional association with alphavbeta6 integrin. FEBS letters. 2013; 587(21):3529-34.
5. Zhuang et al., Clinical significance of integrin alphavbeta6 expression effects on gastric carcinoma invasiveness and progression via cancer-associated fibroblasts. Medical oncology. 2013; 30(3): 580.
6. Vogetseder et al., alphav-Integrin isoform expression in primary human tumors and brain metastases. International journal of cancer Journal international du cancer. 2013; 133(10):2362-71.
7. Ahmed et al., αvβ6 Integrin-A Marker for the Malignant Potential of Epithelial Ovarian Cancer. Journal of Histochemistry & Cytochemistry. 2002; 50(10):1371-9.
8. Ahmed et al., Association between alphavbeta6 integrin expression, elevated p42/44 kDa MAPK, and plasminogen-dependent matrix degradation in ovarian cancer. Journal of cellular biochemistry. 2002; 84(4): 675-86.
9. Kawashima et al., Expression of alphav integrin family in gastric carcinomas: increased alphavbeta6 is associated with lymph node metastasis. Pathology, research and practice. 2003; 199(2):57-64.
10. Hsiao et al., Cyclic alphavbeta6-targeting peptide selected from biopanning with clinical potential for head and neck squamous cell carcinoma. Head & neck. 2010; 32(2):160-72.
11. Bates, The alphaVbeta6 integrin as a novel molecular target for colorectal cancer. Future oncology. 2005; 1(6): 821-8.
12. Bandyopadhyay et al., Defining the role of integrin alphavbeta6 in cancer. Current drug targets. 2009; 10(7): 645-52.
13. Thomas et al., $\alpha v \beta 6$ integrin in wound healing and cancer of the oral cavity. Journal of Oral Pathology & Medicine. 2006; 35(1):1-10.
14. Allen et al., Altered Microenvironment Promotes Progression of Preinvasive Breast Cancer: Myoepithelial Expression of alphavbeta6 Integrin in DCIS Identifies High-risk Patients and Predicts Recurrence. Clinical cancer research. 2014; 20(2):344-57.
15. Dutta et al., Integrin $\alpha v \beta 6$ promotes an osteolytic program in cancer cells by upregulating MMP2. Cancer research. 2014.
16. Prudkin et al., Epithelial-to-mesenchymal transition in the development and progression of adenocarcinoma and squamous cell carcinoma of the lung. Modern pathology. 2009; 22(5):668-78.
17. Annes et al., Integrin alphaVbeta6-mediated activation of latent TGF-beta requires the latent TGF-beta binding protein-1. The Journal of cell biology. 2004; 165(5):723-34.
18. Bates et al., Transcriptional activation of integrin beta6 during the epithelial-mesenchymal transition defines a novel prognostic indicator of aggressive colon carcinoma. The Journal of clinical investigation. 2005; 115(2):339-47.
19. Berghoff et al., Invasion patterns in brain metastases of solid cancers. Neuro-Oncology. 2013; 15(12):1664-72.
20. Peng et al., Integrin alphavbeta6 and transcriptional factor Ets-1 act as prognostic indicators in colorectal cancer. Cell & bioscience. 2014; 4(1):53.
21. Moore et al., Therapeutic targeting of integrin alphavbeta6 in breast cancer. Journal of the National Cancer Institute. 2014; 106(8).
22. Berghoff et al., alphavbeta3, alphavbeta5 and alphavbeta6 integrins in brain metastases of lung cancer. Clinical & experimental metastasis. 2014; 31(7):841-51.
23. Niu et al., Protein expression of eIF4E and integrin alphavbeta6 in colon cancer can predict clinical significance, reveal their correlation and imply possible mechanism of interaction. Cell & bioscience. 2014; 4:23.
24. Sun et al., Interleukin-8 promotes cell migration through integrin alphavbeta6 upregulation in colorectal cancer. Cancer letters. 2014; 354(2):245-53.
25. Wang et al., SDF-1/CXCR4 axis promotes directional migration of colorectal cancer cells through upregulation of integrin alphavbeta6. Carcinogenesis. 2014; 35(2):282-91.
26. Bates, Colorectal cancer progression: integrin alphavbeta6 and the epithelial-mesenchymal transition (EMT). Cell cycle. 2005; 4(10):1350-2.
27. Elez et al., Abituzumab combined with cetuximab plus irinotecan versus cetuximab plus irinotecan alone for patients with KRAS wild-type metastatic colorectal cancer: the randomised phase I/II POSEIDON trial. Annals of oncology: official journal of the European Society for Medical Oncology/ESMO. 2014.
28. Nelson, DCIS prognostic markers: a few new candidates emerge. Journal of the National Cancer Institute. 2010; 102(9):588-90.
29. Sipos et al., Immunohistochemical screening for beta6-integrin subunit expression in adenocarcinomas using a novel monoclonal antibody reveals strong up-regulation in pancreatic ductal adenocarcinomas in vivo and in vitro. Histopathology. 2004; 45(3):226-36.
30. Siegel et al., Cancer statistics, 2014. CA: a cancer journal for clinicians. 2014; 64(1):9-29.
31. Chari, Detecting early pancreatic cancer: problems and prospects. Seminars in oncology. 2007; 34(4):284-94.
32. Pelaez-Luna et al., Resectability of presymptomatic pancreatic cancer and its relationship to onset of diabetes: a retrospective review of CT scans and fasting glucose values prior to diagnosis. The American journal of gastroenterology. 2007; 102(10):2157-63.
33. McGuire et al., Biopanning of phage displayed peptide libraries for the isolation of cell-specific ligands. Methods in molecular biology. 2009; 504:291-321.
34. Gray et al., From Phage Display to Nanoparticle Delivery: Functionalizing Liposomes with Multivalent Peptides Improves Targeting to a Cancer Biomarker. Bioconjugate Chemistry. 2012; 24(1):85-96.
35. Miao et al., An engineered knottin peptide labeled with 18F for PET imaging of integrin expression. Bioconjug Chem. 2009; 20(12):2342-7.
36. Hackel et al., 18F-fluorobenzoate-labeled cystine knot peptides for PET imaging of integrin alphavbeta6. Journal of nuclear medicine. 2013; 54(7):1101-5.
37. Gagnon et al., High-throughput in vivo screening of targeted molecular imaging agents. Proceedings of the National Academy of Sciences of the United States of America. 2009; 106(42): 17904-9.
38. Gray et al., Combinatorial Peptide libraries: mining for cell-binding peptides. Chemical reviews. 2014; 114(2): 1020-81.
39. Hausner et al., Targeted in vivo imaging of integrin alphavbeta6 with an improved radiotracer and its relevance in a pancreatic tumor model. Cancer research. 2009; 69(14):5843-50.
40. Hausner et al., Use of a peptide derived from foot-and-mouth disease virus for the noninvasive imaging of human cancer: generation and evaluation of 4-[18F]fluorobenzoyl A20FMDV2 for in vivo imaging of integrin alphavbeta6 expression with positron emission tomography. Cancer research. 2007; 67(16):7833-40.
41. Hausner et al., In vitro and in vivo evaluation of the effects of aluminum [(1)(8)F]fluoride radiolabeling on an integrin alphavbeta(6)-specific peptide. Nuclear medicine and biology. 2014; 41(1):43-50.
42. Hausner et al., Evaluation of an integrin alphavbeta6-specific peptide labeled with [18F]fluorine by copper-free, strain-promoted click chemistry. Nuclear medicine and biology. 2013; 40(2):233-9.
43. Hausner et al., Evaluation of [64Cu]Cu-DOTA and [64Cu]Cu-CB-TE2A chelates for targeted positron emission tomography with an alphavbeta6-specific peptide. Molecular imaging. 2009; 8(2): 111-21.
44. Hausner et al., In vivo positron emission tomography (PET) imaging with an alphavbeta6 specific peptide radiolabeled using 18F-"click" chemistry: evaluation and comparison with the corresponding 4-[18F]fluorobenzoyl- and 2-[18F]fluoropropionyl-peptides. Journal of medicinal chemistry. 2008; 51(19):5901-4.
45. Semmler et al., Molecular Imaging II. Preface. Handbook of experimental pharmacology. 2008 (185 Pt 2):vii-ix.
46. Li et al., (64)Cu-labeled tetrameric and octameric RGD peptides for small-animal PET of tumor alpha(v)beta(3) integrin expression. Journal of nuclear medicine. 2007; 48(7):1162-71.
47. Zhou et al., Radiolabeled Cyclic RGD Peptides as Radiotracers for Imaging Tumors and Thrombosis by SPECT. Theranostics. 2011; 1:58-82.
48. White et al., Optimization of the solid-phase synthesis of [18F] radiolabeled peptides for positron emission tomography. Applied radiation and isotopes: including data, instrumentation and methods for use in agriculture, industry and medicine. 2012; 70(12):2720-9.
49. Dou et al., Expression, purification, and characterization of recombinant human serum albumin fusion protein with two human glucagon-like peptide-1 mutants in *Pichia pastoris*. Protein expression and purification. 2008; 61(1): 45-9.
50. Smith et al., Prolonged in vivo residence times of antibody fragments associated with albumin. Bioconjug Chem. 2001; 12(5):750-6.
51. Nguyen et al., The pharmacokinetics of an albumin-binding Fab (AB.Fab) can be modulated as a function of affinity for albumin. Protein engineering, design & selection: PEDS. 2006; 19(7):291-7.
52. Dumelin et al., A portable albumin binder from a DNA-encoded chemical library. Angewandte Chemie. 2008; 47(17):3196-201.
53. Muller et al., DOTA conjugate with an albumin-binding entity enables the first folic acid-targeted 177Lu-radionuclide tumor therapy in mice. Journal of nuclear medicine. 2013; 54(1):124-31.
54. Fischer et al., Improved PET imaging of tumors in mice using a novel (18) F-folate conjugate with an albumin-binding entity. Molecular imaging and biology. 2013; 15(6):649-54.
55. Pang et al., A free cysteine prolongs the half-life of a homing peptide and improves its tumor-penetrating activity. Journal of controlled release. 2014; 175:48-53.
56. Ellerby et al., Anti-cancer activity of targeted pro-apoptotic peptides. Nature medicine. 1999; 5(9):1032-8.
57. Barbu et al., An Antimicrobial Peptidomimetic Induces Mucorales Cell Death through Mitochondria-Mediated Apoptosis. PLoS ONE. 2013; 8(10):e76981.
58. Arap et al., Targeting the prostate for destruction through a vascular address. Proceedings of the National Academy of Sciences of the United States of America. 2002; 99(3):1527-31.
59. Fantin et al., A bifunctional targeted peptide that blocks HER-2 tyrosine kinase and disables mitochondrial function in HER-2-positive carcinoma cells. Cancer research. 2005; 65(15):6891-900.
60. Karjalainen et al., Targeting neuropilin-1 in human leukemia and lymphoma. Blood. 2011; 117(3):920-7.
61. Bertrand et al., Cancer nanotechnology: The impact of passive and active targeting in the era of modern cancer biology. Advanced Drug Delivery Reviews. 2013(0).
62. Von Hoff et al., Increased Survival in Pancreatic Cancer with nab-Paclitaxel plus Gemcitabine. New England Journal of Medicine. 2013; 369(18):1691-703.
63. Friedman et al., The smart targeting of nanoparticles. Current pharmaceutical design. 2013; 19(35):6315-29.
64. Luo et al., Well-defined, size-tunable, multifunctional micelles for efficient paclitaxel delivery for cancer treatment. Bioconjug Chem. 2010; 21(7):1216-24.
65. Li et al., A novel size-tunable nanocarrier system for targeted anticancer drug delivery. Journal of Controlled Release. 2010; 144(3):314-23.
66. Waldherr et al., Tumor response and clinical benefit in neuroendocrine tumors after 7.4 GBq (90)Y-DOTATOC. Journal of nuclear medicine. 2002; 43(5):610-6.
67. Bodei et al., Receptor radionuclide therapy with 90Y-[DOTA]0-Tyr3-octreotide (90Y-DOTATOC) in neuroendocrine tumours. Eur J Nucl Med Mol Imaging. 2004; 31(7):1038-46.
68. Van Essen et al., Peptide Receptor Radionuclide Therapy with radiolabelled somatostatin analogues in patients with somatostatin receptor positive tumours. Acta oncologica. 2007; 46(6): 723-34.
69. Norenberg et al., 213Bi-[DOTAO, Tyr3]octreotide peptide receptor radionuclide therapy of pancreatic tumors in a preclinical animal model. Clinical cancer research. 2006; 12(3 Pt 1): 897-903.
70. Imhof et al., Response, survival, and long-term toxicity after therapy with the radiolabeled somatostatin analogue [90Y-DOTA]-TOC in metastasized neuroendocrine cancers. Journal of clinical oncology. 2011; 29(17):2416-23.
71. Rolleman et al., Safe and effective inhibition of renal uptake of radiolabelled octreotide by a combination of lysine and arginine. Eur J Nucl Med Mol Imaging. 2003; 30(1):9-15.
72. Kunikowska et al., Clinical results of radionuclide therapy of neuroendocrine tumours with 90Y-DOTATATE and tandem 90Y/177Lu-DOTATATE: which is a better therapy option? Eur J Nucl Med Mol Imaging. 2011; 38(10):1788-97.

Example 4. Bi-Terminal PEGylated Peptides with Improved Stability, Radiolabeling Yields, and Lipophilicity for $\alpha_v\beta_6$-Targeted Molecular Imaging and Therapy This example illustrates that bi-terminal PEGylation using a shorter PEG moiety such as $PEG_{11}$ (i.e., polyethylene glycol of 11 repeating units) was able to confer superior in vitro characteristics to an 8 amino acid peptide that binds to $\alpha_v\beta_6$ integrin (i.e., RSDLTPLF; SEQ ID NO:4) by improving its stability in serum, radiolabeling yields, and lipophilicity. Although the parent peptide, H-RSDLTPLFNH$_2$; SEQ ID NO:4), has a high affinity of 7 nM and is 100 times more selective for $\alpha_v\beta_6$ over $\alpha_v\beta_3$, serum stability studies of this peptide revealed poor in vitro stability. As such, this example demonstrates that a bi-terminal PEGylated version of this peptide advantageously provides high selectively for $\alpha_v\beta_6$ integrin and high serum stability for in vivo imaging and therapy.

I. Materials and Methods

Materials

All chemicals were purchased from Sigma Aldrich (St. Louis Mo.), Acros (New Jersey), Fluka (St. Louis Mo.), and Fisher Scientific (Waltham, Mass.) unless otherwise specified. NovaSyn TGR resin was purchased from Novabiochem (La Jolla, Calif.). 9-fluorenylmethyoxycarbonyl (Fmoc) amino acids and peptide synthesis reagents were purchased from Novabiochem and GLS-China (Shanghai, China). Polyethylene glycol of 11 repeating units ($PEG_{11}$) was purchased from Polypure (Oslo, Norway). All amino acids used were L-amino acids.

Manual solid-phase peptide synthesis was performed using standard Fmoc chemistry in 1 mL or 5 mL fritted reactor vials purchased from Breakwood Enterprises (Akron, Ohio) and Fisher Scientific. Reverse-phase high performance liquid chromatography (RP-HPLC) was performed using either Beckman-Coulter (Brea, Calif.) chromatography systems with diode array UV detectors at 220 nm and 254 nm, along with the 32Karat software package or the Ultimate 3000 RP-HPLC system by Dionex (Sunnyvale, Calif.) with diode array UV detectors, with the Chromeleon software package. Purification and analysis were performed using Jupiter C-12 columns (250×460 mm, 4 micron, Phenomenex) with mobile phases consisting of 0.05% trifluoroacetic acid (TFA) in water (solvent A) and 100% acetonitrile (solvent B). Products were eluted off the columns using a linear gradient of 9% solvent B for two minutes and increasing over 30 minutes to 81% solvent B with a constant flow rate of 1.5 mL/minute. Mass spectrometry (MS) of the purified compounds was obtained using an ABI 4700 high-resolution matrix assisted laser desorption/ionization time-of-flight (MALDI-TOF) system (Applied Biosystems, Foster City, Calif.).

[$^{18}$F]fluoride for radiolabeling was produced by the $^{18}$O (p,n) $^{18}$F reaction using an 11 MeV Siemens RDS 111 negative ion cyclotron in-house at the Center for Molecular and Genomic Imaging (Davis, Calif.), or purchased from PETNET Solutions (Sacramento, Calif.). Radioactivity was measured using a Capintec dose calibrator (Capintec Inc, Ramsey, N.J.). HPLC gold 168 (Beckman-Coulter) in series with a Gabistar Radiation Detector (Raytest, Straubenhardt, Germany) was used to measure the purity and radiochemical purity of the samples respectively. The detectors were connected in series, resulting in a slight difference in retention times observed for radioactive compounds and their corresponding cold standards.

Affinity of each peptide was assessed ELISA on Nunc Maxisorp Flat-bottom 96 well plates (affymetrix ebioscience, San Diego, Calif.). Integrin alpha V antibody P2W7 was purchased from Novus Biologicals (Littleton, Colo.). Bovine serum albumin (BSA) was purchased from VWR (Randor, Pa.) and TMB one solution was purchased from Promega (Madison, Wis.). $\alpha_v\beta_6$ integrin was purchased from R&D systems (Minneapolis, Minn.). Protein biotinylation kit was purchased from Amersham plc (Amersham, UK) while competing natural ligand fibronectin was purchased from Invitrogen (Carlsbad, Calif.). Affinity was measured in absorbance units by the Thermo Multiscan Plate reader with associated Ascent Software (Thermofisher, Waltham, Mass.).

Solid-Phase Synthesis of NH$_2$-Peptides

Peptide synthesis was performed manually using standard Fmoc solid-phase techniques (Table 2) (Chan et al., (2003) *Fmoc Solid Phase Peptide Synthesis. A Practical Approach*. Oxford University Press). Novasyn TGR resin (300 mg) was weighed out and transferred into a 5 ml reactor vial. N, N-dimethylformamide (DMF) was added to the reactor vial for 1.5 hours to allow the resins to swell and then drained over vacuum. Amino acid coupling was performed by adding 3 equiv. of O-(7-azabenzotriazol-1-yl)-N, N, N, N'-tetramethyluronium hexafluorophosphate (HATU) and (Fmoc)-protected amino acids, and 6 equiv. N, N-diisopropylethelamine (DIPEA) to the reactor vial and coupled for 1.5 hours on an automatic rotator.

TABLE 2

List of peptides synthesized. Peptides synthesized without [$^{19}$F]FBA (left column), peptides synthesized with FBA (right column).

| NH$_2$-peptides (SEQ ID NOS: 4, 31-36) | [$^{19}$F]FBA peptides (SEQ ID NOS: 37-43) |
|---|---|
| H-RSDLTPLF-NH$_2$ | FBA-RSDLTPLF-NH$_2$ |
| Boc-RSDLTPLFK(NH$_2$)-NH$_2$ | Boc-RSDLTPLFK(FBA)-NH$_2$ |
| H-RSDLTPLFK(Boc)-NH$_2$ | FBA-RSDLTPLFK(Boc)-NH$_2$ |
| H-PEG$_{11}$-RSDLTPLF-NH$_2$ | FBA-PEG$_{11}$-RSDLTPLF-NH$_2$ |
| H-RSDLTPLF-PEG$_{11}$-NH$_2$ | FBA-RSDLTPLF-PEG$_{11}$-NH$_2$ |
| H-PEG$_{11}$-RSDLTPLF-PEG$_{11}$-NH$_2$ | FBA-PEG$_{11}$-RSDLTPLF-PEG$_{11}$-NH$_2$ |
| c(RSDLTPLFE)K(IvdDe)-NH$_2$ | c(RSDLTPLFE)K(FBA)-NH$_2$ |

Coupling reactions were monitored by picrylsulfonic acid (PSA) test for all amino acids except for proline in which the chloranil test was used (Chan et al., 2003). A sample of the resin beads was placed onto a ceramic test plate, a drop of PSA test solution consisting of 100 DMF, 10 µL DIPEA, and one drop of PSA was added to the sample. In the case of a secondary amine, the chloranil test was performed after washing with DMF (3×); a drop of chloranil solution consisting of 53 mg of p-tetrachlorobenzoquinone and 50 µL of acetaldehyde in 2.5 mL of DMF (Chan et al., 2003). The presence of unreacted free amines yields red colored beads for the PSA test; blue for the chloranil test. After complete coupling reactions the beads were rinsed with DMF (3×) and drained. Fmoc removal was achieved using 20% piperidine in DMF for 15 minutes (2×). The resin was subsequently washed with DMF (3×), Methanol (3×), and DMF (3×) followed by PSA test or chloranil test. The process for coupling an amino acid was repeated until the desired peptide sequence was completed.

In the case of Boc-RSDLTPLFK(NH$_2$)—NH$_2$ (SEQ ID NO:31), Fmoc-Lys(ivDde)-OH was initially coupled to the resin by adding Fmoc-Lys(ivDde)-OH (3 equiv.), HATU (2.99 equiv.), and DIPEA (6 equiv.) in DMF and coupled with the conditions described for solid-phase peptide synthesis. Coupling of the remaining sequence used amino acids with standard protecting groups, except for the addition of arginine, Boc-Arg(Pbf)-OH was used in place of Fmoc-Arg(Pbf)-OH to yield a free N-terminal amine after cleavage from the resin. After elongation of the sequence was completed, deprotection of the 1-(4,4-dimethyl-2,6-dioxocyclohex-1-ylidene)isovaleryl (ivDde) protecting group on Lysine was performed by mixing the peptide with 60 µL of hydrazine in 2.94 mL of DMF for 15 minutes (2×) (Conroy et al., (2008) Efficient use of the Dmab protecting group: applications for the solid-phase synthesis of N-linked glycopeptides. Organic & Biomolecular Chemistry 7(11): 2255-2258). The resin was rinsed with DMF (3×), MeOH (3×), and DMF (3×) and tested with PSA solution to determine presence of a free amine.

In the case of H-RSDLTPLFK(Boc)-NH2 (SEQ ID NO:32), Fmoc-Lys(Boc)-OH was initially coupled to the resin by adding Fmoc-Lys(Boc)-OH (3 equiv.), HATU (2.99 equiv.), and DIPEA (6 equiv.) in DMF and coupled with the conditions described for solid-phase peptide synthesis. The remaining couplings used amino acids with standard protecting groups.

For the synthesis of H-RSDLTPLF-PEG$_{11}$-NH$_2$ (SEQ ID NO:34) and H-PEG$_{11}$-RSDLTPLF-PEG$_{11}$-NH$_2$ (SEQ ID NO:35), Fmoc-PEG$_{11}$-OH was initially coupled to the resin by adding Fmoc-PEG$_{11}$-OH (1.1 equiv.), HATU (1.1 equiv.), and DIPEA (2 equiv.) in DMF and placed on an automatic rotator for 16 hours, followed by a second coupling for 6 hours. Coupling reactions were monitored by PSA test. After complete coupling reactions the beads were rinsed with DMF (3×) and drained. Fmoc removal was performed. The remaining sequence was completed by coupling the amino acids with standard protecting groups. The N-terminal PEGylation for H-PEG$_{11}$-RSDLTPLF-NH$_2$ (SEQ ID NO:33) and H-PEG$_{11}$-RSDLTPLF-PEG$_{11}$-NH$_2$ (SEQ ID NO:35) were performed after the successful coupling and Fmoc deprotection of the N-terminal arginine. Fmoc-PEG$_{11}$-OH was coupled to the peptide on resin (peptidyl resin) by adding Fmoc-PEG$_{11}$-OH (1.1 equiv.), HATU (1.1 equiv.), and DIPEA (2 equiv.) in DMF and placed on an automatic rotator for 16 hours, followed by a second coupling for 6 hours. Coupling reactions were monitored by picrylsulfonic acid (PSA) test.

Synthesis and cyclization of c(RSDLTPLFE)K (SEQ ID NO:53) was achieved with solid-phase peptide synthesis. Synthesis of c(RSDLTPLFE)K-NH$_2$ (SEQ ID NO:53) was achieved by first coupling Fmoc-Lys(ivDde)-OH to the resin by adding Fmoc-Lys(ivDde)-OH (3 equiv.), HATU (2.99 equiv.), and DIPEA (6 equiv.) in DMF and coupled with the conditions described for solid-phase peptide synthesis. Afterwards, Fmoc-Glu(OAll)-OH was coupled by the addition of Fmoc-Glu(OAll)-OH (3 equiv.), HATU (2.99 equiv.), and DIPEA (6 equiv.) in DMF. The remaining couplings used amino acids with standard protecting groups. After the sequence was completely assembled, the resin was dried via lyophilizer overnight. The peptidyl resin was rinsed and swelled in dichloromethane (DCM). The Allyl side-chain of glutamic acid was deprotected by adding 20 equivalents of phenylsilane and 0.5 equivalents of tetrakis(triphenylphosphine)palladium(0) in roughly 2-3 mL of DCM.

The phenylsilane/tetrakis(triphenyphosphine)palladium (0) solution was briefly bubbled with nitrogen, pipetted into the reaction vessel to add to the peptidyl resin, and placed on the rotator for 30 minutes (2×). Afterwards the peptidyl resin was washed with 1% DIPEA in DMF (v/v) (3×), 100% DMF (3×), 5% diethyldithiocarbamic acid (wt/v) sodium salt in DMF (3×), and 100% DMF (3×) (Chan et al., 2003). The peptidyl resin was then washed with MeOH (3×) and DMF (3×). The Fmoc protecting group was removed. To cyclize the peptide, HATU (0.99 equiv.) and DIPEA (2.0 equiv.) was mixed with 2 mL of DMF, added to the peptidyl resin and placed onto the rotator for 16 hours. Complete coupling was measured by PSA test. Following cyclization, the side-chain of (ivDde) was removed by mixing the peptidyl resin with 2% hydrazine solution in DMF for 15 minutes (2×). The peptidyl resin was rinsed with DMF (3×), MeOH (3×), and DMF (3×) and tested with PSA solution to determine the presence of a free amine.

To test the purity, samples of the peptides were cleaved off the resin (10 mg) and side-chain protecting groups removed by use of trifluoracetic acid (TFA)/1, 2-ethanedithiol/TIPS/ water in 94:2.5:1:2.5 (v/v/v/v) for 3 hours. Post cleavage work-up consisted of evaporating TFA by a low pressure air stream followed by adding 1 mL of water. The crude peptide was then dissolved in water and ethyl ether, gently mixed and the ether layer was removed. The mixing and removal of ether was performed (3×) with the crude peptide isolated into the water layer. The water layer was lyophilized. Analytical purification was achieved by RP-HPLC over a linear gradient of solvent B for two minutes; increasing from 9% to 81% solvent B over 30 minutes. The products were collected, lyophilized and the mass of the product confirmed using MALDI-TOF.

Synthesis of [$^{19}$F]FBA Peptides

After completion of the NH$_2$-peptide sequences, [$^{19}$F] FBA (cold FBA) was site specifically conjugated to each peptide (Table 2). 10 mg of each of the peptidyl resin were coupled with [$^{19}$F]FBA (10 equiv.), HATU (20 equiv.), and DIPEA (40 equiv.) for 1.5 hours. Peptides were then cleaved. The products were analyzed by RP-HPLC and mass confirmed by MALDI-TOF.

ELISA of [$^{19}$F]FBA Peptides for Integrin $\alpha_v\beta_6$

The affinity of each [$^{19}$F]FBA peptide towards $\alpha_v\beta_6$ and $\alpha_v\beta_3$ were compared by competitive binding ELISA (Gagnon et al., (2009) High-throughput in vivo screening of targeted molecular imaging agents. Proceedings of the National Academy of Sciences 106(42):17904-17909). The peptides were allowed to compete for 1 h with biotinylated fibronectin, a natural ligand for $\alpha_v\beta_6$; or biotinylated vitronectin, when competing against $\alpha_v\beta_3$. Briefly, a 96-well plate was coated with 50 μL/well of 5 μg/mL P2W7 in phosphate buffered saline (PBS) at 37° C. for 1 h. The plate was washed three times with PBS followed by treatment with PBS containing 5% bovine serum albumin (BSA; fraction V; w/v) and 1% Tween 20 (v/v) at 4° C. for 16 h to block nonspecific binding. The plate was washed with PBS and coated with 50 μL/well integrin in wash buffer (WaB) for 1 h and then washed three times with WaB. WaB consisted of a solution of 2 mmol/L Tris buffer (pH 7.6), 150 mmol/L sodium chloride, 1 mmol/L manganese chloride, and 0.1% Tween 20 (v/v) in deionized water. Triplicate wells were coated with 50 μL/well of a mixture of equal volumes of biotinylated fibronectin (BtFn) for $\alpha_v\beta_6$, or biotinylated vitronectin (BtVn) for $\alpha_v\beta_3$, in conjugate buffer, consisting of 1% BSA (fraction V; w/v) in WaB, and a serial dilution of peptide stock (2 mmol/L; 10% DMSO (v/v) in water) from 1 μM to 1 pM. Wells containing no peptide, no peptide and no antibody, or no peptide and no ligand served as controls. The plate was incubated for 1 h at room temperature and washed three times with WaB before ExtrAvidin-horseradish peroxidase conjugate was added (50 μL/well, 1:1,000 dilution in conjugate buffer) at room temperature for 1 h. After washing with WaB, bound BtFn or BtVn was detected by addition of TMB (50 μL/well) and incubation for 10 to 15 min. The reaction was terminated by adding 50 μL/well 1N sulfuric acid and absorbance was measured at 450 nm (yellow color of acidified oxidized TMB, indicating fibronectin binding). Calculations of IC$_{50}$ values are based on data analysis with Prism software (GraphPad Software).

Solid-Phase Radiolabeling of $\alpha_v\beta_6$ Targeting Peptides with [$^{18}$F]FBA Solid-phase radiolabeling techniques were adapted from methods published previously (Hausner et al., (2009) Targeted In vivo imaging of integrin $\alpha_v\beta_6$ with an improved radiotracer and its relevance in a pancreatic tumor model, Cancer Research, 69:5343). [$^{18}$F]fluoride (0.6-2.8 Ci) was produced by the cyclotron and delivered onto an ion exchange trap and release column (ORTG, Oakdale, Tenn.). The [$^{18}$F]fluoride was then eluted into a 5 mL conical vial with 2 mL of a 4,7,13,16,21,24-hexaoxa-1,-10-diazabicyclo [8.8.8]hexacosane (K222) and potassium carbonate (K$_2$CO$_3$) solution (100 mg K222 in 9.4 mL of ACN, 20 mg K$_2$CO$_3$ in 0.6 mL H$_2$O). Residual water was removed by evaporation at 100° C. using a nitrogen stream and dried by azeotropic distillation with the addition of 1 mL of ACN (3×). [$^{18}$F]FBA precursor solution (ethyl 4-(trimethylammoniumtriflate) benzoate, 5 mg, in 0.5 mL anhydrous DMSO) was added to the conical vial (15 minutes, 100° C.), and followed by 1.0 mL of 0.5N sodium hydroxide (NaOH) and heated at 100° C. for 10 minutes. The solution was then aspirated into a syringe containing 2 mL of 1N hydrochloric acid (HCL) and 6 mL of H$_2$O. The product was trapped onto a C-18 SepPak column (Waters, Milford, Mass.) and washed with 5 mL of H$_2$O and eluted with 2.2 mL of ACN into a 5 mL conical vial containing 50 µL of DMF. Remaining solvents were evaporated leaving [$^{18}$F]FBA in DMF.

[$^{18}$F]FBA (500 mCi) was coupled to each peptidyl resin using solid-phase coupling techniques. The peptidyl resin (3-5 mg) was placed into a 1 mL fritted syringe and swollen for 1 h in DMF prior to radiolabeling. DMF was expelled from the each peptide syringe and 0.5-1.0 Ci of [$^{18}$F]FBA in DMF were drawn up into each of the peptides syringes to couple to the resin-bound peptides. HATU (15-30 equiv. in 30 µL DMF) and DIPEA (30-60 equiv. in 20 µL of DMF) was then drawn up into the syringe and reacted for 30 minutes at room temperature. Post coupling of the [$^{18}$F]FBA the peptidyl resin was washed thoroughly with DMF (3×), MeOH (3×), and air (3×) and radioactivity was recorded. Final products were cleaved from the resin by addition of 250 µL TFA/TIPs/water 95:2.5:2.5 (v/v/v) for 15 minutes (2×). Radioactivity was measured by a Capintec dose calibrator and recorded at the start of synthesis, after coupling, and after TFA evaporation (end of synthesis). Cleavage mixtures were then evaporated under nitrogen and the final products were reconstituted in a mixture of 0.5 mL HPLC solvent A/ACN 50/50 (v/v). The total synthesis time before HPLC and the radioactivity of the final product were recorded. Purifications were performed using radio-RP-HPLC with previously described conditions for RP-HPLC. Each HPLC purified [$^{18}$F]FBA peptide was then trapped onto a C18 SepPak plus (conditioned with 10 mL EtOH abs, 10 mL water, 3×10 mL air). The SepPak was washed with 5 mL water and 20 mL of air, followed by 250 uL EtOH abs and 20 mL of air. The [$^{18}$F]FBA peptide was then eluted off the SepPak with 1 mL of EtOH abs/glacial acetic acid 100:1, dried (50° C., 25 minutes), and then formulated in 1 mL PBS.

Serum Stability of [$^{18}$F]FBA Peptides

Peptide susceptibility to proteases in mouse serum was determined. Formulated [$^{18}$F]FBA peptide (100 µCi) was incubated with 1 mL of mouse serum for 1 hour at 37° C. A 100 µL aliquot was taken at 1 hour and transferred into an Eppendorf containing 500 µL EtOH abs (4° C.) to precipitate serum proteins. The sample was briefly mixed and chilled for 3 minutes on dry ice, followed by centrifugation at 10,000 g for 2.5 minutes. 100 µL of the supernatant was then mixed with 700 µL of HPLC solvent A (0.05% TFA/water) and 20 µL glacial acetic acid (HOAc) and analyzed by radio-RP-HPLC.

Distribution Coefficient of $\alpha_v\beta_6$ Targeting Peptides

The distribution coefficient (log D) measures the lipophilicity of compound in an ionized solution. The formulated [$^{18}$F]FBA peptide was diluted into PBS to a concentration of 4 µCi/mL to form the radiolabeled peptide stock solution. Aliquots of 50 µL of the radiolabeled peptide stock solution were transferred into an Eppendorf tube (1.5 mL). 450 µL of PBS (hydrophilic layer) and 500 µL of n-octanol (lipophilic layer) were added. The Eppendorf was vortexed for 3 minutes (experiment carried out in quadruplicate). Samples were centrifuged at 10,000 rpm for 6 minutes forming two separate layers consisting of the top layer (n-octanol) and bottom layer (PBS). 100 µL of each layer were pipetted and the radioactivity in each layer was measured and recorded by a gamma counter. The log D is calculated from the equation:

$$\log D = \text{Log}\left(\frac{\text{Counts per minute of Octanol}}{\text{Counts per minute of } PBS}\right).$$

II. Results

ELISA of [$^{19}$F]FBA Peptides

The affinity for both $\alpha_v\beta_6$ and $\alpha_v\beta_3$ for [$^{19}$F]FBA peptide sequences were measured with ELISA. The IC$_{50}$ of the peptides for $\alpha_v\beta_6$ ranged from 1.97 nM (H-RSDLTPLFK([$^{19}$F]FBA)-NH$_2$; SEQ ID NO:44) to >300 nM (c(RSDLTPLFE)K([$^{19}$F]FBA)-NH$_2$ (SEQ ID NO:43) (Table 3).

TABLE 3

IC$_{50}$ values in nM of [$^{19}$F]FBA peptides from ELISA against $\alpha_v\beta_6$, calculated by PRISM.

| Sequence (SEQ ID NOS: 37, 44, 45, 40-43, respectively) | IC$_{50}$ |
|---|---|
| [$^{19}$F]FBA-RSDLTPLF-NH$_2$ | 7 nM |
| H-RSDLTPLFK([$^{19}$F]FBA)-NH$_2$ | 34 nM |
| [$^{19}$F]FBA-RSDLTPLFK(NH$_2$)-NH$_2$ | 1.97 nM |
| [$^{19}$F]FBA-PEG$_{11}$-RSDLTPLF-NH$_2$ | 40 nM |
| [$^{19}$F]FBA-RSDLTPLF-PEG$_{11}$-NH$_2$ | 40 nM |
| [$^{19}$F]FBA-PEG$_{11}$-RSDLTPLF-PEG$_{11}$-NH$_2$ | 25 nM |
| c(RSDLTPLFE)K([$^{19}$F]FBA)-NH$_2$ | >300 nM |

The IC$_{50}$ of all peptides for $\alpha_v\beta_3$ were >100 µM. Selectivity of the [$^{19}$F]FBA peptides for $\alpha_v\beta_6$ over $\alpha_v\beta_3$ ranged from 300 to 10,000 fold in favor of $\alpha_v\beta_6$. The ELISA of the [$^{19}$F]FBA peptides showed high affinity for $\alpha_v\beta_6$ with an IC$_{50}$ in the low, single to double digit, nanomolar range, with the exception of c(RSDLTPLFE)K([$^{19}$F]FBA)-NH$_2$ (SEQ ID NO:43).

Solid-Phase Radiolabeling of $\alpha_v\beta_6$ Targeting Peptides with [$^{18}$F]FBA

[$^{18}$F]FBA was synthesized with a final purity >95% purity. [$^{18}$F]FBA were synthesized in 80.5±12% yield and confirmed to be >95% purity by radio RP-HPLC. [$^{18}$F]FBA peptides were synthesized with radiolabeling yields ranging from 6.8±1.0% to 65.9±5.5% after decay correction from start of [$^{18}$F]FBA coupling to end of TFA evaporation (Table 4).

TABLE 4

[$^{18}$F]FBA peptides and their radiolabeling yields decay corrected to the start of [$^{18}$F]FBA coupling.

| Peptide Sequence (SEQ ID NOS: 46-52) | Radiolabeling Yield |
|---|---|
| [$^{18}$F]FBA-RSDLTPLF-NH$_2$ | 9.2 ± 4.1% |
| H-RSDLTPLFK([$^{18}$F]FBA)-NH$_2$ | 32.6 ± 1.0% |
| [$^{18}$F]FBA-RSDLTPLFK(NH$_2$)-NH$_2$ | 22.4 ± 0.3% |
| [$^{18}$F]FBA-PEG$_{11}$-RSDLTPLF-NH$_2$ | 17.0 ± 7.1% |
| [$^{18}$F]FBA-RSDLTPLF-PEG$_{11}$-NH$_2$ | 42.2 ± 5.5% |
| [$^{18}$F]FBA-PEG$_{11}$-RSDLTPLF-PEG$_{11}$-NH$_2$ | 65.9 ± 5.5% |
| c(RSDLTPLFE)K([$^{18}$F]FBA)-NH | 6.8 ± 1.0% |

The addition of a PEG$_{11}$ increased the radiolabeling yields by 2 to 7 times. With PEG$_{11}$ at the N-terminus on [$^{18}$F]FBA-PEG$_{11}$-RSDLTPLF (SEQ ID NO:49) nearly doubled the radiolabeling yields from 9.2% to 17%, while with PEG$_{11}$ at the C-terminus increased the radiolabeling yields four-fold from 9.2% to 42.2%. The bi-PEGylated peptide [$^{18}$F]FBA-PEG$_{11}$-RSDLTPLF-PEG$_{11}$-NH$_2$ (SEQ ID NO:51) increased the radiolabeling yield seven-fold from 9.2% to 65.9%. Without being bound by any particular theory, it is believed that by adding PEG units, the free amine is extended further from the resin, potentially making it more accessible for [$^{18}$F]FBA, thus increasing radiolabeling yields.

Serum Stability of [$^{18}$F]FBA Peptides

The level of intact peptide was measured for each of the [$^{18}$F]FBA peptides after incubation in mouse serum for 1 hour (Table 5). The unmodified peptide [$^{18}$F]FBA-RSDLTPLF-NH$_2$ (SEQ ID NO:46) showed 66% intact in mouse serum after 1 hour. Overall, the percentage of intact [$^{18}$F]FBA peptides ranged from 18.6 to 99.7%.

TABLE 5

[$^{18}$F]FBA peptides and their 1 hour serum stability measured by radio RP-HPLC.

| Peptide Sequence (SEQ ID NOS: 46-52) | Serum Stability |
|---|---|
| [$^{18}$F]FBA-RSDLTPLF-NH$_2$ | 66.0% |
| H-RSDLTPLFK([$^{18}$F]FBA)-NH$_2$ | 18.6% |
| [$^{18}$F]FBA-RSDLTPLFK(NH$_2$)-NH$_2$ | 95.2% |
| [$^{18}$F]FBA-PEG$_{11}$-RSDLTPLF-NH$_2$ | 94.6% |
| [$^{18}$F]FBA-RSDLTPLF-PEG$_{11}$-NH$_2$ | 99.1% |
| [$^{18}$F]FBA-PEG$_{11}$-RSDLTPLF-PEG$_{11}$-NH$_2$ | 99.7% |
| c(RSDLTPLFE)K([$^{18}$F]FBA)-NH | 98.4% |

The first modification, NH$_2$-RSDLTPLFK([$^{18}$F]FBA)-NH$_2$ (SEQ ID NO:47), showed worse results as the peptide degraded to 18.6% after 1 h in mouse serum. The exposed N-terminus is susceptible to enzymes such as amino and endo-peptidases, resulting in rapid peptide degradation. For the [$^{18}$F]FBA labeled N-terminus in [$^{18}$F]FBA-RSDLTPLFK(NH$_2$)—NH$_2$ (SEQ ID NO:48), nearly no degradation of the peptide by proteases was observed with 95.2% of the peptide intact after 1 hour in mouse serum.

Adding lysine on the C-terminus of H-RSDLTPLF-NH$_2$ (SEQ ID NO:4) appears to play a role in reducing protease recognition of the peptide sequence, potentially allowing the peptide to remain largely intact. Similarly, PEGylation on either the N or C-terminus, or bi-PEGylation saw significant improvements in serum stability with serum stabilities of 94.6%, 99.1%, and 99.7%, respectively. Adding PEG$_{11}$ on the N or C-terminus played a role in preventing protease interaction; thus bi-PEGylated [$^{18}$F]FBA-PEG$_{11}$-RSDLTPLF-PEG$_{11}$-NH$_2$ (SEQ ID NO:51) further perpetuated the trend by having the largest percentage of intact peptide after incubating in mouse serum for 1 hour.

Distribution Coefficient of $\alpha_v\beta_6$ Targeting Peptides

The lipophilicity of each of the radiolabeled peptides was measured for each modification. The log D ranged from ~1.86±0.26 to 0.45±0.03 (Table 6). The base peptide [$^{18}$F]FBA-RSDLTPLF-NH$_2$ (SEQ ID NO:46) had an initial log D value of 0.45, revealing a slight lipophilicity. Peptides that are lipophilic are often associated with hepatobiliary clearance, resulting in in vivo images with higher signal in the abdomen (Hosseinimehr et al., (2012) Liver uptake of radiolabeled targeting proteins and peptides: considerations for targeting peptide conjugated design, Drug Discovery Today 17(21-22):1224-32). All of the modifications reduced the lipophilicity, the least being c(RSDLTPLFE)K([$^{18}$F]FBA)-NH$_2$ (SEQ ID NO:52) with a log D of 0.02, to the highest being from bi-PEGylation with a log D of −1.86. The reduction of lipophilicity has several potential pharmacokinetic advantages such as a shift from hepatobiliary clearance to renal clearance and allowing for the desirable rapid, renal excretion, potentially reducing the abdominal background for in vivo imaging (Hosseinimehr et al., 2012).

TABLE 6

LogD values for [$^{18}$F]FBA peptides.

| Peptide Sequence (SEQ ID NOS: 46-52) | LogD |
|---|---|
| [$^{18}$F]FBA-RSDLTPLF-NH$_2$ | 0.45 ± 0.03 |
| H-RSDLTPLFK([$^{18}$F]FBA)-NH$_2$ | −0.49 ± 0.09 |
| [$^{18}$F]FBA-RSDLTPLFK(NH$_2$)-NH$_2$ | −1.44 ± 0.10 |
| [$^{18}$F]FBA-PEG$_{11}$-RSDLTPLF-NH$_2$ | −1.18 ± 0.22 |
| [$^{18}$F]FBA-RSDLTPLF-PEG$_{11}$-NH$_2$ | −1.29 ± 0.09 |
| [$^{18}$F]FBA-PEG$_{11}$-RSDLTPLF-PEG$_{11}$-NH$_2$ | −1.86 ± 0.26 |
| c(RSDLTPLFE)K([$^{18}$F]FBA)-NH$_2$ | 0.02 ± 0.04 |

In conclusion, this example demonstrates that a bi-terminal PEGylated peptide of the present invention having the structure PEG$_{11}$-RSDLTPLF-PEG$_{11}$ (SEQ ID NO:35) advantageously provides high selectively for $\alpha_v\beta_6$ integrin and improved serum stability, radiolabeling yields, and lipophilicity when compared to the parent peptide sequence, a cyclic version of the peptide, and individual N- or C-terminal PEGylated versions of the peptide.

All publications, patents, and patent applications cited in this specification are herein incorporated by reference as if each individual publication, patent, or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A conjugate comprising:
   (a) a peptide that binds to an integrin, wherein the peptide comprises the amino acid sequence RSDLTPLF$X_7$ (SEQ ID NO:4), wherein $X_7$ is absent or is any amino acid;
   (b) a first polyethylene glycol (PEG) moiety covalently attached to the amino-terminus of the peptide; and
   (c) a second PEG moiety covalently attached to the carboxyl-terminus of the peptide.

2. The conjugate of claim 1, wherein $X_7$ is absent.

3. The conjugate of claim 1, wherein $X_7$ is K.

4. The conjugate of claim 1, wherein the peptide is between 8 and about 45 amino acids in length.

5. The conjugate of claim 1, wherein the peptide is between 8 and about 25 amino acids in length.

6. The conjugate of claim 1, wherein the peptide is about 21 or more amino acids in length.

7. The conjugate of claim 1, wherein the first PEG moiety and the second PEG moiety each have a molecular weight of less than about 3000 daltons (Da).

8. The conjugate of claim 7, wherein the first PEG moiety and the second PEG moiety are independently selected from the group consisting of $PEG_{11}$, $PEG_{12}$ (PEG 800), PEG28 (PEG 1500), and $(PEG_{28})_2$ (PEG 1500×2).

9. The conjugate of claim 1, wherein the first PEG moiety and the second PEG moiety are the same.

10. The conjugate of claim 9, wherein the first PEG moiety and the second PEG moiety are both $PEG_{11}$.

11. The conjugate of claim 1, wherein the first PEG moiety and the second PEG moiety are monodisperse PEG moieties having a defined chain length.

12. The conjugate of claim 11, wherein the monodisperse PEG moieties have greater than about 95% oligomer purity.

13. The conjugate of claim 1, wherein the conjugate further comprises an imaging agent or a therapeutic agent covalently attached to the peptide, the first PEG moiety, or the second PEG moiety,
wherein the imaging agent is selected from the group consisting of a radionuclide, biotin, a fluorophore, a fluorescent protein, an antibody, horseradish peroxidase, alkaline phosphatase, and combinations thereof, and
wherein the therapeutic agent is selected from the group consisting of a radionuclide, a pro-apoptotic peptide, a nanoparticle, a chemotherapeutic agent, a nanodroplet, a liposomal drug, a cytokine, and combinations thereof.

14. The conjugate of claim 13, wherein the imaging agent is a radionuclide selected from the group consisting of $^{11}C$, $^{13}N$, $^{15}O$, $^{18}F$, $^{19}F$, $^{61}Cu$, $^{64}Cu$, $^{67}Cu$, $^{68}Ga$, $^{111}In$, $^{124}I$, $^{125}I$, $^{131}I$.

15. The conjugate of claim 13, wherein the imaging agent is a radionuclide attached via a prosthetic group to the peptide, the first PEG moiety, or the second PEG moiety, wherein the prosthetic group is selected from the group consisting of a benzoyl group, fluoropropionic acid, pyridine, dipyridyl-tetrazine, trans-cyclooctene, and combinations thereof.

16. The conjugate of claim 13, wherein the therapeutic agent is a radionuclide selected from the group consisting of $^{90}Y$ and $^{177}Lu$.

17. The conjugate of claim 13, wherein the therapeutic agent is a radionuclide attached via a chelating agent to the peptide, the first PEG moiety, or the second PEG moiety.

18. The conjugate of claim 13, wherein the pro-apoptotic peptide comprises $D(KLAKLAK)_2$.

19. The conjugate of claim 13, wherein the pro-apoptotic peptide is attached via a glycine linker to the peptide, the first PEG moiety, or the second PEG moiety.

20. The conjugate of claim 13, wherein the nanoparticle comprises $PEG^{5K}CA_8$ loaded with a chemotherapeutic agent.

21. The conjugate of claim 13, wherein the chemotherapeutic agent is paclitaxel (PTX), gemcitabine, or combinations thereof.

22. The conjugate of claim 1, wherein the conjugate further comprises an albumin binding motif covalently attached to the peptide, the first PEG moiety, or the second PEG moiety.

23. The conjugate of claim 22, wherein the albumin binding motif is 4-(4-iodophenyl)butyric acid.

24. A composition comprising a conjugate of claim 1 or a plurality thereof.

25. A kit for imaging or therapy, the kit comprising:
(a) a conjugate of claim 1; and
(b) directions for use of the conjugate in imaging or therapy.

26. A method for the in vivo imaging of a target tissue, the method comprising:
(a) administering to a subject in need of such imaging, a conjugate of claim 1, wherein an imaging agent is covalently attached to the peptide, the first PEG moiety, or the second PEG moiety; and
(b) detecting the conjugate to determine where the conjugate is concentrated in the subject,
wherein the imaging agent is selected from the group consisting of a radionuclide, biotin, a fluorophore, a fluorescent protein, an antibody, horseradish peroxidase, alkaline phosphatase, and combinations thereof.

27. The method of claim 26, wherein the target tissue is a cancerous tissue or an organ.

28. The method of claim 26, wherein the imaging agent is a radionuclide, and wherein radiation from the radionuclide is used to determine where the conjugate is concentrated in the subject.

29. A method for treating an integrin-mediated disease or disorder in a subject in need thereof, the method comprising:
administering to the subject a therapeutically effective amount of a conjugate of claim 1, wherein a therapeutic agent is covalently attached to the peptide, the first PEG moiety, or the second PEG moiety,
wherein the therapeutic agent is selected from the group consisting of a radionuclide, a pro-apoptotic peptide, a nanoparticle, a chemotherapeutic agent, a nanodroplet, a liposomal drug, a cytokine, and combinations thereof, and
wherein the disease or disorder is selected from the group consisting of cancer, an inflammatory disease, an autoimmune disease, chronic fibrosis, chronic obstructive pulmonary disease (COPD), lung emphysema, and chronic wounding skin disease.

30. The method of claim 29, wherein the disease or disorder is an $\alpha_v\beta_6$ integrin-mediated disease or disorder.

* * * * *

SEQUENCE LISTING

```
<160> NUMBER OF SEQ ID NOS: 53

<210> SEQ ID NO 1
<211> LENGTH: 6
<212> TYPE: PRT
<213> ORGANISM: Artificial Sequence
<220> FEATURE:
<223> OTHER INFORMATION: synthetic amino acid sequence
<220> FEATURE:
<221> NAME/KEY: MOD_RES
<222> LOCATION: (3)..(3)
<223> OTHER INFORMATION: Xaa is hydroxyproline

<400> SEQUENCE: 1

Gly Phe Xaa Gly Glu Arg
1               5
```

```
<210> SEQ ID NO 2
<211> LENGTH: 7
<212> TYPE: PRT
<213> ORGANISM: Artificial Sequence
<220> FEATURE:
<223> OTHER INFORMATION: synthetic alpha-five beta-six integrin-binding
      peptide
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu or Ile

<400> SEQUENCE: 2

Arg Gly Asp Leu Xaa Xaa Xaa
1               5

<210> SEQ ID NO 3
<211> LENGTH: 10
<212> TYPE: PRT
<213> ORGANISM: Artificial Sequence
<220> FEATURE:
<223> OTHER INFORMATION: synthetic alpha-five beta-six integrin-binding
      peptide
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu or Ile
<220> FEATURE:
<221> NAME/KEY: MISC_FEATURE
<222> LOCATION: (10)..(10)
<223> OTHER INFORMATION: Xaa is Lys or Arg

<400> SEQUENCE: 3

Arg Gly Asp Leu Xaa Xaa Xaa Ala Gln Xaa
1               5                   10

<210> SEQ ID NO 4
<211> LENGTH: 9
<212> TYPE: PRT
<213> ORGANISM: Artificial Sequence
<220> FEATURE:
<223> OTHER INFORMATION: synthetic alpha-five beta-six integrin-binging
      protein
<220> FEATURE:
<221> NAME/KEY: MISC_FEATURE
<222> LOCATION: (9)..(9)
<223> OTHER INFORMATION: Xaa is absent or any amino acid

<400> SEQUENCE: 4

Arg Ser Asp Leu Thr Pro Leu Phe Xaa
1               5

<210> SEQ ID NO 5
<211> LENGTH: 20
<212> TYPE: PRT
<213> ORGANISM: Artificial Sequence
<220> FEATURE:
<223> OTHER INFORMATION: synthetic alpha-five beta-six integrin-binding
      protein A20FMDV2 or A20FMDV2 K16R
<220> FEATURE:
<221> NAME/KEY: MISC_FEATURE
<222> LOCATION: (16)..(16)
<223> OTHER INFORMATION: Xaa is Lys (A20FMDV2) or Arg (A20FMDV2 K16R)
```

```
<400> SEQUENCE: 5

Asn Ala Val Pro Asn Leu Arg Gly Asp Leu Gln Val Leu Ala Gln Xaa
1               5                   10                  15

Val Ala Arg Thr
            20

<210> SEQ ID NO 6
<211> LENGTH: 14
<212> TYPE: PRT
<213> ORGANISM: Artificial Sequence
<220> FEATURE:
<223> OTHER INFORMATION: synthetic proapoptotic heptapeptide dimer

<400> SEQUENCE: 6

Lys Leu Ala Lys Leu Ala Lys Lys Leu Ala Lys Leu Ala Lys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic alpha-five beta-six integrin-binding
      peptide
<220> FEATURE:
<221> NAME/KEY: MISC_FEATURE
<222> LOCATION: (5)..(6)
<223> OTHER INFORMATION: Xaa is any helix-promoting amino acid; Xaa is
      preferably Glu, Ala, Leu, Met, Gln, Lys, Arg, Val, Ile, His, Thr,
      Trp, Phe, or Asp
<220> FEATURE:
<221> NAME/KEY: MISC_FEATURE
<222> LOCATION: (8)..(10)
<223> OTHER INFORMATION: Xaa is any helix-promoting amino acid; Xaa is
      preferably Glu, Ala, Leu, Met, Gln, Lys, Arg, Val, Ile, His, Thr,
      Trp, Phe, or Asp

<400> SEQUENCE: 7

Arg Gly Asp Leu Xaa Xaa Leu Xaa Xaa Xaa
1               5                   10

<210> SEQ ID NO 8
<211> LENGTH: 4
<212> TYPE: PRT
<213> ORGANISM: Artificial Sequence
<220> FEATURE:
<223> OTHER INFORMATION: synthetic alpha-helix peptide
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Leu or Ile

<400> SEQUENCE: 8

Leu Xaa Xaa Xaa
1

<210> SEQ ID NO 9
<211> LENGTH: 30
<212> TYPE: PRT
<213> ORGANISM: Artificial Sequence
<220> FEATURE:
<223> OTHER INFORMATION: synthetic alpha-five beta-six integrin-binding
      peptide
<220> FEATURE:
<221> NAME/KEY: MISC_FEATURE
<222> LOCATION: (5)..(6)
```

```
<223> OTHER INFORMATION: Xaa is any helix-promoting amino acid; Xaa is
      preferably Glu, Ala, Leu, Met, Gln, Lys, Arg, Val, Ile, His, Thr,
      Trp, Phe, or Asp
<220> FEATURE:
<221> NAME/KEY: MISC_FEATURE
<222> LOCATION: (8)..(10)
<223> OTHER INFORMATION: Xaa is any helix-promoting amino acid; Xaa is
      preferably Glu, Ala, Leu, Met, Gln, Lys, Arg, Val, Ile, His, Thr,
      Trp, Phe, or Asp
<220> FEATURE:
<221> NAME/KEY: MISC_FEATURE
<222> LOCATION: (11)..(30)
<223> OTHER INFORMATION: Xaa is 1 to 20 amino acids; 19 may be present
      or absent.  Xaa is any helix-promoting amino acid; Xaa is
      preferably Glu, Ala, Leu, Met, Gln, Lys, Arg, Val, Ile, His, Thr,
      Trp, Phe, or Asp

<400> SEQUENCE: 9

Arg Asp Gly Leu Xaa Xaa Leu Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

<210> SEQ ID NO 10
<211> LENGTH: 80
<212> TYPE: PRT
<213> ORGANISM: Artificial Sequence
<220> FEATURE:
<223> OTHER INFORMATION: synthetic alpha-five beta-six integrin-binding
      peptide
<220> FEATURE:
<221> NAME/KEY: MISC_FEATURE
<222> LOCATION: (1)..(35)
<223> OTHER INFORMATION: Xaa is 1 to 35 amino acids, 34 amino acids may
      be present or absent
<220> FEATURE:
<221> NAME/KEY: MISC_FEATURE
<222> LOCATION: (1)..(35)
<223> OTHER INFORMATION: Xaa is amino acids which enhance hydrophobic
      interactions with the helix LXXL and enhance RGD domain for
      binding
<220> FEATURE:
<221> NAME/KEY: MISC_FEATURE
<222> LOCATION: (40)..(41)
<223> OTHER INFORMATION: Xaa is any amino acid
<220> FEATURE:
<221> NAME/KEY: MISC_FEATURE
<222> LOCATION: (43)..(45)
<223> OTHER INFORMATION: Xaa is any amino acid
<220> FEATURE:
<221> NAME/KEY: MISC_FEATURE
<222> LOCATION: (46)..(80)
<223> OTHER INFORMATION: Xaa is 1 to 35 amino acids, 34 amino acids may
      be present or absent
<220> FEATURE:
<221> NAME/KEY: MISC_FEATURE
<222> LOCATION: (46)..(80)
<223> OTHER INFORMATION: Xaa is a helix-promoting amino acid

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Arg Gly Asp Leu Xaa Xaa Leu Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80
```

```
<210> SEQ ID NO 11
<211> LENGTH: 20
<212> TYPE: PRT
<213> ORGANISM: Artificial Sequence
<220> FEATURE:
<223> OTHER INFORMATION: synthetic alpha-five beta-six integrin binding
      peptide (A20LAP)

<400> SEQUENCE: 11

Gly Phe Thr Thr Gly Arg Arg Gly Asp Leu Ala Thr Ile His Gly Met
1               5                   10                  15

Asn Arg Pro Phe
            20

<210> SEQ ID NO 12
<211> LENGTH: 20
<212> TYPE: PRT
<213> ORGANISM: Artificial Sequence
<220> FEATURE:
<223> OTHER INFORMATION: synthetic alpha-five beta-six integrin-binding
      protein (A20FMDV1)

<400> SEQUENCE: 12

Tyr Thr Ala Ser Ala Arg Gly Asp Leu Ala His Leu Thr Thr Thr His
1               5                   10                  15

Ala Arg His Leu
            20

<210> SEQ ID NO 13
<211> LENGTH: 20
<212> TYPE: PRT
<213> ORGANISM: Artificial Sequence
<220> FEATURE:
<223> OTHER INFORMATION: synthetic peptide FBA-PEG28-A20FMDV2-PEG28
      imaging probe with A20FMDV2 (SEQ ID NO:5) core
<220> FEATURE:
<221> NAME/KEY: MOD_RES
<222> LOCATION: (1)..(1)
<223> OTHER INFORMATION: Xaa is fluorobenzoic acid (FBA) linked to
      polyethylene glycol (PEG)28 conjugated to Asn
<220> FEATURE:
<221> NAME/KEY: MISC_FEATURE
<222> LOCATION: (16)..(16)
<223> OTHER INFORMATION: Xaa is Lys or Arg
<220> FEATURE:
<221> NAME/KEY: MOD_RES
<222> LOCATION: (20)..(20)
<223> OTHER INFORMATION: Xaa is Thr conjugated to polyethylene glycol
      (PEG)28

<400> SEQUENCE: 13

Xaa Ala Val Pro Asn Leu Arg Gly Asp Leu Gln Val Leu Ala Gln Xaa
1               5                   10                  15

Val Ala Arg Xaa
            20

<210> SEQ ID NO 14
<211> LENGTH: 20
<212> TYPE: PRT
<213> ORGANISM: Artificial Sequence
<220> FEATURE:
<223> OTHER INFORMATION: synthetic 18F-FBA-A20FMDV2 imaging probe with
      A20FMDV2 (SEQ ID NO:5) core
<220> FEATURE:
<221> NAME/KEY: MOD_RES
<222> LOCATION: (1)..(1)
<223> OTHER INFORMATION: Xaa is fluorine-18 (radio)labeled fluorobenzoic
      acid (FBA) conjugated to Asn
<220> FEATURE:
```

```
<221> NAME/KEY: MISC_FEATURE
<222> LOCATION: (16)..(16)
<223> OTHER INFORMATION: Xaa is Lys or Arg

<400> SEQUENCE: 14

Xaa Ala Val Pro Asn Leu Arg Gly Asp Leu Gln Val Leu Ala Gln Xaa
1               5                   10                  15

Val Ala Arg Thr
            20

<210> SEQ ID NO 15
<211> LENGTH: 20
<212> TYPE: PRT
<213> ORGANISM: Artificial Sequence
<220> FEATURE:
<223> OTHER INFORMATION: synthetic peptide 18F-FBA-PEG28-A20FMDV2
      imaging probe with A20FMDV2 (SEQ ID NO:5) core
<220> FEATURE:
<221> NAME/KEY: MOD_RES
<222> LOCATION: (1

```
<221> NAME/KEY: MISC_FEATURE
<222> LOCATION: (16)..(16)
<223> OTHER INFORMATION: Xaa is Lys or Arg
<220> FEATURE:
<221> NAME/KEY: MOD_RES
<222> LOCATION: (20)..(20)
<223> OTHER INFORMATION: Xaa is Thr conjugated to polyethylene glycol
      (PEG)28

<400> SEQUENCE: 17

Xaa Ala Val Pro Asn Leu Arg Gly Asp Leu Gln Val Leu Ala Gln Xaa
1               5                   10                  15

Val Ala Arg Xaa
            20

<210> SEQ ID NO 18
<211> LENGTH: 20
<212> TYPE: PRT
<213> ORGANISM: Artificial Sequence
<220> FEATURE:
<223> OTHER INFORMATION: synthetic peptide 18F-FBA-A20FMDV2-PEG28
      imaging prob

```
<210> SEQ ID NO 20
<211> LENGTH: 20
<212> TYPE: PRT
<213> ORGANISM: Artificial Sequence
<220> FEATURE:
<223> OTHER INFORMATION: synthetic peptide FBA-PEG28-A20FMDV2 imaging
      probe with A20FMDV2 (SEQ ID NO:5) core
<220> FEATURE:
<221> NAME/KEY: MOD_RES
<222> LOCATION: (1)..(1)
<223> OTHER INFORMATION: Xaa is fluorobenzoic acid (FBA) linked to
      polyethylene glycol (PEG)28 conjugated to Asn
<220> FEATURE:
<221> NAME/KEY: MISC_FEATURE
<222> LOCATION: (16)..(16)
<223> OTHER INFORMATION: Xaa is Lys or Arg

<400> SEQUENCE: 20

Xaa Ala Val Pro Asn Leu Arg Gly Asp Leu Gln Val Leu Ala Gln Xaa
1               5                   10                  15

Val Ala Arg Thr
            20

<210> SEQ ID NO 21
<211> LENGTH: 20
<212> TYPE: PRT
<213> ORGANISM: Artificial Sequence
<220> FEATURE:
<223> OTHER INFORMATION: synthetic peptide PEG28-A20FMDV2 K16R-PEG28
      imaging probe with A20FMDV2 K16R (SEQ ID NO:5) core
<220> FEATURE:
<221> NAME/KEY: MOD_RES
<222> LOCATION: (1

```
<222> LOCATION: (17)..(17)
<223> OTHER INFORMATION: Xaa is polyethylene glycol (PEG)28 conjugated
      to Asn
<220> FEATURE:
<221> NAME/KEY: MISC_FEATURE
<222> LOCATION: (32)..(32)
<223> OTHER INFORMATION: Xaa is Lys or Arg
<220> FEATURE:
<221> NAME/KEY: MOD_RES
<222> LOCATION: (36)..(36)
<223> OTHER INFORMATION: Xaa is Thr conjugated to polyethylene glycol
      (PEG)28

<400> SEQUENCE: 22

Lys Leu Ala Lys Leu Ala Lys Lys Leu Ala Lys Leu Ala Lys Gly Xaa
1               5                   10                  15

Xaa Ala Val Pro Asn Leu Arg Gly Asp Leu Gln Val Leu Ala Gln Xaa
            20                  25                  30

Val Ala Arg Xaa
        35

<210> SEQ ID NO 23
<211> LENGTH: 37
<212> TYPE: PRT
<213> ORGANISM: Artificial Sequence
<220> FEATURE:
<223> OTHER INFORMATION: synthetic peptide PEG28-A20MFDV2-GG-
      D(KLAKLAK)2-K
<220> FEATURE:
<221> NAME/KEY: MOD_RES
<222> LOCATION: (1)..(1)
<223> OTHER INFORMATION: Xaa is polyethylene glycol (PEG)28 conjugated
      to Asn
<220> FEATURE:
<221> NAME/KEY: MISC_FEATURE
<222> LOCATION: (16)..(16)
<223> OTHER INFORMATION: Xaa is Lys or Arg
<220> FEATURE:
<221> NAME/KEY: MISC_FEATURE
<222> LOCATION: (21)..(22)
<223> OTHER INFORMATION: Gly-Gly (GG) linker
<220> FEATURE:
<221> NAME/KEY: MISC_FEATURE
<222> LOCATION: (36)..(36)
<223> OTHER INFORMATION: Lys linked to terminal Lys at position 37

<400> SEQUENCE: 23

Xaa Ala Val Pro Asn Leu Arg Gly Asp Leu Gln Val Leu Ala Gln Xaa
1               5                   10                  15

Val Ala Arg Thr Gly Gly Lys Leu Ala Lys Leu Ala Lys Lys Leu Ala
            20                  25                  30

Lys Leu Ala Lys Lys
        35

<210> SEQ ID NO 24
<211> LENGTH: 37
<212> TYPE: PRT
<213> ORGANISM: Artificial Sequence
<220> FEATURE:
<223> OTHER INFORMATION: synthetic peptide D(KLAKLAK)2-GG-PEG28-
      A20FMDV2-K
<220> FEATURE:
<221> NAME/KEY: MISC_FEATURE
<222> LOCATION: (15)..(16)
<223> OTHER INFORMATION: Gly-Gly (GG) linker
<220> FEATURE:
<221> NAME/KEY: MOD_RES
<222> LOCATION: (16)..(16)
<223> OTHER INFORMATION: Xaa is Gly linked to PEG28
<220> FEATURE:
<221> NAME/KEY: MOD_RES
```

```
<222> LOCATION: (17)..(17)
<223> OTHER INFORMATION: Xaa is polyethylene glycol (PEG)28 conjugated
      to Asn
<220> FEATURE:
<221> NAME/KEY: MISC_FEATURE
<222> LOCATION: (32)..(32)
<223> OTHER INFORMATION: Xaa is Lys or Arg
<220> FEATURE:
<221> NAME/KEY: MISC_FEATURE
<222> LOCATION: (36)..(36)
<223> OTHER INFORMATION: Thr linked to terminal Lys at position 37

<400> SEQUENCE: 24

Lys Leu Ala Lys Leu Ala Lys Lys Leu Ala Lys Leu Ala Lys Gly Xaa
1               5                   10                  15

Xaa Ala Val Pro Asn Leu Arg Gly Asp Leu Gln Val Leu Ala Gln Xaa
            20                  25                  30

Val Ala Arg Thr Lys
            35

<210> SEQ ID NO 25
<211> LENGTH: 20
<212> TYPE: PRT
<213> ORGANISM: Artificial Sequence
<220> FEATURE:
<223> OTHER INFORMATION: synthetic peptide 90Y-DOTA-PEG28-
      A20FMDV2(K16R)-PEG28
<220> FEATURE:
<221> NAME/KEY: MOD_RES
<222> LOCATION: (1)..(1)
<223> OTHER INFORMATION: Xaa is yttrium 90 (radio

```
<400> SEQUENCE: 26

Xaa Ala Val Pro Asn Leu Arg Gly Asp Leu Gln Val Leu Ala Gln Xaa
1               5                   10                  15

Val Ala Arg Xaa
            20

<210> SEQ ID NO 27
<211> LENGTH: 20
<212> TYPE: PRT
<213> ORGANISM: Artificial Sequence
<220> FEATURE:
<223> OTHER INFORMATION: synthetic peptide PEG28-A20FMDV2(K16R)-PEG28-
      PEG5K-CA8-PTX
<220> FEATURE:
<221> NAME/KEY: MOD_RES
<222> LOCATION: (1)..(1)
<223> OTHER INFORMATION: Xaa is polyethylene glycol (PEG)28 conjugated
      to Asn
<220> FEATURE:
<221> NAME/KEY: MISC_FEATURE
<222> LOCATION: (16)..(16)
<223> OTHER INFORMATION: Xaa is Lys or Arg
<220> FEATURE:
<221> NAME/KEY: MOD_RES
<222> LOCATION: (20)..(20)
<223> OTHER INFORMATION: Xaa is Thr conjugated to polyethylene glycol
      (PEG)28 conjugated to polyethylene glycol (PEG5000) cholic acid
      (CA8) loaded with paclitaxel (PTX)

<400> SEQUENCE: 27

Xaa Ala Val Pro Asn Leu Arg Gly Asp Leu Gln Val Leu Ala Gln Xaa
1               5                   10                  15

Val Ala Arg Xaa
            20

<210> SEQ ID NO 28
<211> LENGTH: 20
<212> TYPE: PRT
<213> ORGANISM: Artificial Sequence
<220> FEATURE:
<223> OTHER INFORMATION: synthetic peptide alkynyl-PEG28-A20FMDV2(K16R)-
      PEG28
<220> FEATURE:
<221> NAME/KEY: MOD_RES
<222> LOCATION: (1)..(1)
<223> OTHER INFORMATION: Xaa is alkynyl linked polyethylene glycol
      (PEG)28 conjugated to Asn
<220> FEATURE:
<221> NAME/KEY: MISC_FEATURE
<222> LOCATION: (16)..(16)
<223> OTHER INFORMATION: Xaa is Lys or Arg
<220> FEATURE:
<221> NAME/KEY: MOD_RES
<222> LOCATION: (20)..(20)
<223> OTHER INFORMATION: Xaa is Thr conjugated to polyethylene glycol
      (PEG)28

<400> SEQUENCE: 28

Xaa Ala Val Pro Asn Leu Arg Gly Asp Leu Gln Val Leu Ala Gln Xaa
1               5                   10                  15

Val Ala Arg Xaa
            20

<210> SEQ ID NO 29
<211> LENGTH: 20
<212> TYPE: PRT
<213> ORGANISM: Artificial Sequence
<220> FEATURE:
<223> OTHER INFORMATION: synthetic peptide PEG28-A20FMDV2(K16R)-PEG28-
      PEG5K-CA8
```

```
<220> FEATURE:
<221> NAME/KEY: MOD_RES
<222> LOCATION: (1)..(1)
<223> OTHER INFORMATION: Xaa is polyethylene glycol (PEG)28 conjugated
      to Asn
<220> FEATURE:
<221> NAME/KEY: MISC_FEATURE
<222> LOCATION: (16)..(16)
<223> OTHER INFORMATION: Xaa is Lys or Arg
<220> FEATURE:
<221> NAME/KEY: MOD_RES
<222> LOCATION: (20)..(20)
<223> OTHER INFORMATION: Xaa is Thr conjugated to polyethylene glycol
      (PEG)28 conjugated to polyethylene glycol (PEG5000) cholic acid
      (CA8)

<400> SEQUENCE: 29

Xaa Ala Val Pro Asn Leu Arg Gly Asp Leu Gln Val Leu Ala Gln Xaa
1               5                   10                  15

Val Ala Arg Xaa
            20

<210> SEQ ID NO 30
<211> LENGTH: 20
<212> TYPE: PRT
<213> ORGANISM: Artificial Sequence
<220> FEATURE:
<223> OTHER INFORMATION: synthetic peptide FBA-K(IPA)E-PEG28-
      NAVPNLRGDLQVLAQKVART-PEG28
<220> FEATURE:
<221> NAME/KEY: MOD_RES
<222> LOCATION: (1)..(1)
<223> OTHER INFORMATION: Xaa is fluorobenzoic acid (FBA) linked to
      epsilon-(4-(4-iodophenyl)butyl amide)lysine-glutamic acid)
      polyethylene glycol (PEG)28 conjugated to Asn
<220> FEATURE:
<221> NAME/KEY: MOD_RES
<222> LOCATION: (20)..(20)
<223> OTHER INFORMATION: Xaa is Thr conjugated to polyethylene glycol
      (PEG)28

<400> SEQUENCE: 30

Xaa Ala Val Pro Asn Leu Arg Gly Asp Leu Gln Val Leu Ala Gln Lys
1               5                   10                  15

Val Ala Arg Xaa
            20

<210> SEQ ID NO 31
<211> LENGTH: 9
<212> TYPE: PRT
<213> ORGANISM: Artificial Sequence
<220> FEATURE:
<223> OTHER INFORMATION: synthetic peptide Boc-RSDLTPLFK(NH2)-NH2
<220> FEATURE:
<221> NAME/KEY: MOD_RES
<222> LOCATION: (1)..(1)
<223> OTHER INFORMATION: Xaa is tert-butyloxycarbonyl (Boc) conjugated
      to Arg
<220> FEATURE:
<221> NAME/KEY: MOD_RES
<222> LOCATION: (9)..(9)
<223> OTHER INFORMATION: Xaa is Lys linked to a free N-terminal amine

<400> SEQUENCE: 31

Xaa Ser Asp Leu Thr Pro Leu Phe Xaa
1               5

<210> SEQ ID NO 32
<211> LENGTH: 9
<212> TYPE: PRT
<213> ORGANISM: Artificial Sequence
```

```
<220> FEATURE:
<223> OTHER INFORMATION: synthetic peptide RSDLTPLFK(Boc)-NH2
<220> FEATURE:
<221> NAME/KEY: MOD_RES
<222> LOCATION: (9)..(9)
<223> OTHER INFORMATION: Xaa is Lys conjugated to tert-butyloxycarbonyl
      (Boc) linked to a free N-terminal amine

<400> SEQUENCE: 32

Arg Ser Asp Leu Thr Pro Leu Phe Xaa
1               5

<210> SEQ ID NO 33
<211> LENGTH: 8
<212> TYPE: PRT
<213> ORGANISM: Artificial Sequence
<220> FEATURE:
<223> OTHER INFORMATION: synthetic peptide PEG11-RSDLTPLF-NH2
<220> FEATURE:
<221> NAME/KEY: MOD_RES
<222> LOCATION: (1)..(1)
<223> OTHER INFORMATION: Xaa is polyethylene glycol (PEG)11 conjugated
      to Arg

<400> SEQUENCE: 33

Xaa Ser Asp Leu Thr Pro Leu Phe
1               5

<210> SEQ ID NO 34
<211> LENGTH: 8
<212> TYPE: PRT
<213> ORGANISM: Artificial Sequence
<220> FEATURE:
<223> OTHER INFORMATION: synthetic peptide RSDLTPLF- PEG11-NH2
<220> FEATURE:
<221> NAME/KEY: MOD_RES
<222> LOCATION: (8)..(8)
<223> OTHER INFORMATION: Xaa is Phe conjugated to polyethylene glycol
      (PEG)11

<400> SEQUENCE: 34

Arg Ser Asp Leu Thr Pro Leu Xaa
1               5

<210> SEQ ID NO 35
<211> LENGTH: 8
<212> TYPE: PRT
<213> ORGANISM: Artificial Sequence
<220> FEATURE:
<223> OTHER INFORMATION: synthetic peptide PEG11-RSDLTPLF-PEG11-NH2
<220> FEATURE:
<221> NAME/KEY: MOD_RES
<222> LOCATION: (1)..(1)
<223> OTHER INFORMATION: Xaa is polyethylene glycol (PEG)11 conjugated
      to Arg
<220> FEATURE:
<221> NAME/KEY: MOD_RES
<222> LOCATION: (8)..(8)
<223> OTHER INFORMATION: Xaa is Phe conjugated to polyethylene glycol
      (PEG)11

<400> SEQUENCE: 35

Xaa Ser Asp Leu Thr Pro Leu Xaa
1               5

<210> SEQ ID NO 36
<211> LENGTH: 10
<212> TYPE: PRT
<213> ORGANISM: Artificial Sequence
<220> FEATURE:
<223> OTHER INFORMATION: synthetic peptide c(RSDLTPLFE)K(IvdDe)-NH2
```

```
<220> FEATURE:
<221> NAME/KEY: MISC_FEATURE
<222> LOCATION: (1)..(9)
<223> OTHER INFORMATION: residues undergo cyclization
<220> FEATURE:
<221> NAME/KEY: MOD_RES
<222> LOCATION: (10)..(10)
<223> OTHER INFORMATION: Xaa is Lys with protecting group
      1-(4,4-dimethyl-2,6-dioxocyclohex-1-ylidene)isovaleryl (ivDde)
      linked to a free N-terminal amine

<400> SEQUENCE: 36

Arg Ser Asp Leu Thr Pro Leu Phe Glu Xaa
1               5                   10

<210> SEQ ID NO 37
<211> LENGTH: 8
<212> TYPE: PRT
<213> ORGANISM: Artificial Sequence
<220> FEATURE:
<223> OTHER INFORMATION: synthetic peptide 19F-FBA-RSDLTPLF
<220> FEATURE:
<221> NAME/KEY: MOD_RES
<222> LOCATION: (1)..(1)
<223> OTHER INFORMATION: Xaa is fluorine-19 (radio)labeled fluorobenzoic
      acid (FBA) conjugated to Arg

<400> SEQUENCE: 37

Xaa Ser Asp Leu Thr Pro Leu Phe
1               5

<210> SEQ ID NO 38
<211> LENGTH: 9
<212> TYPE: PRT
<213> ORGANISM: Artificial Sequence
<220> FEATURE:
<223> OTHER INFORMATION: synthetic peptide Boc-RSDLTPLFK(19F-FBA)-NH2
<220> FEATURE:
<221> NAME/KEY: MOD_RES
<222> LOCATION: (1)..(1)
<223> OTHER INFORMATION: Xaa is tert-butyloxycarbonyl (Boc) conjugated
      to Arg
<220> FEATURE:
<221> NAME/KEY: MOD_RES
<222> LOCATION: (9)..(9)
<223> OTHER INFORMATION: Xaa is Lys conjugated fluorine-19
      (radio)labeled fluorobenzoic acid (FBA) linked to a free
      N-terminal amine

<400> SEQUENCE: 38

Xaa Ser Asp Leu Thr Pro Leu Phe Xaa
1               5

<210> SEQ ID NO 39
<211> LENGTH: 9
<212> TYPE: PRT
<213> ORGANISM: Artificial Sequence
<220> FEATURE:
<223> OTHER INFORMATION: synthetic peptide 19F-FBA-RSDLTPLFK(Boc)NH2
<220> FEATURE:
<221> NAME/KEY: MOD_RES
<222> LOCATION: (1)..(1)
<223> OTHER INFORMATION: Xaa is fluorine-19 (radio)labeled fluorobenzoic
      acid (FBA) conjugated to Arg
<220> FEATURE:
<221> NAME/KEY: MOD_RES
<222> LOCATION: (9)..(9)
<223> OTHER INFORMATION: Xaa is Lys with protecting group
      tert-butyloxycarbonyl (Boc) linked to a free N-terminal amine

<400> SEQUENCE: 39

Xaa Ser Asp Leu Thr Pro Leu Phe Xaa
```

-continued

```
<210> SEQ ID NO 40
<211> LENGTH: 8
<212> TYPE: PRT
<213> ORGANISM: Artificial Sequence
<220> FEATURE:
<223> OTHER INFORMATION: synthetic peptide 19F-FBA-(PEG)11-RSDLTPLF-NH2
<220> FEATURE:
<221> NAME/KEY: MOD_RES
<222> LOCATION: (1)..(1)
<223> OTHER INFORMATION: Xaa is fluorine-19 (radio)labeled fluorobenzoic
      acid (FBA) conjugated to polyethylene glycol (PEG)11 conjugated to
      Arg

<400> SEQUENCE: 40

Xaa Ser Asp Leu Thr Pro Leu Phe
1               5

<210> SEQ ID NO 41
<211> LENGTH: 8
<212> TYPE: PRT
<213> ORGANISM: Artificial Sequence
<220> FEATURE:
<223> OTHER INFORMATION: synthetic peptide 19F-FBA-RSDLTPLF-(PEG)11-NH2
<220> FEATURE:
<221> NAME/KEY: MOD_RES
<222> LOCATION: (1)..(1)
<223> OTHER INFORMATION: Xaa is fluorine-19 (radio)labeled fluorobenzoic
      acid (FBA) conjugated to Arg
<220> FEATURE:
<221> NAME/KEY: MOD_RES
<222> LOCATION: (8)..(8)
<223> OTHER INFORMATION: Xaa is Phe conjugated to polyethylene glycol
      (PEG)11

<400> SEQUENCE: 41

Xaa Ser Asp Leu Thr Pro Leu Xaa
1               5

<210> SEQ ID NO 42
<211> LENGTH: 8
<212> TYPE: PRT
<213> ORGANISM: Artificial Sequence
<220> FEATURE:
<223> OTHER INFORMATION: synthetic peptide 19F-FBA-PEG11-RSDLTPLF-PEG11-
      NH2
<220> FEATURE:
<221> NAME/KEY: MOD_RES
<222> LOCATION: (1)..(1)
<223> OTHER INFORMATION: Xaa is fluorine-19 (radio)labeled fluorobenzoic
      acid (FBA) conjugated to polyethylene glycol (PEG)11 conjugated to
      Arg
<220> FEATURE:
<221> NAME/KEY: MOD_RES
<222> LOCATION: (8)..(8)
<223> OTHER INFORMATION: Xaa is Phe conjugated to polyethylene glycol
      (PEG)11

<400> SEQUENCE: 42

Xaa Ser Asp Leu Thr Pro Leu Xaa
1               5

<210> SEQ ID NO 43
<211> LENGTH: 10
<212> TYPE: PRT
<213> ORGANISM: Artificial Sequence
<220> FEATURE:
<223> OTHER INFORMATION: synthetic peptide c(RSDLTPLFE)K(19F-FBA)-NH2
<220> FEATURE:
<221> NAME/KEY: MISC_FEATURE
<222> LOCATION: (1)..(9)
```

```
<223> OTHER INFORMATION: residues undergo cyclization
<220> FEATURE:
<221> NAME/KEY: MOD_RES
<222> LOCATION: (10)..(10)
<223> OTHER INFORMATION: Xaa is Lys linked to fluorine-19 (radio)labeled
      fluorobenzoic acid (FBA)
<220> FEATURE:
<221> NAME/KEY: MOD_RES
<222> LOCATION: (10)..(10)
<223> OTHER INFORMATION: Xaa is Lys linked to fluorine-19 (radio)labeled
      fluorobenzoic acid (FBA) linked to a free N-terminal amine

<400> SEQUENCE: 43

Arg Ser Asp Leu Thr Pro Leu Phe Glu Xaa
1               5                   10

<210> SEQ ID NO 44
<211> LENGTH: 9
<212> TYPE: PRT
<213> ORGANISM: Artificial Sequence
<220> FEATURE:
<223> OTHER INFORMATION: synthetic peptide RSDLTPLFK(19F-FBA)-NH2
<220> FEATURE:
<221> NAME/KEY: MOD_RES
<222> LOCATION: (9)..(9)
<223> OTHER INFORMATION: Xaa is Lys conjugated fluorine-19
      (radio)labeled fluorobenzoic acid (FBA) linked to a free
      N-terminal amine

<400> SEQUENCE: 44

Arg Ser Asp Leu Thr Pro Leu Phe Xaa
1               5

<210> SEQ ID NO 45
<211> LENGTH: 9
<212> TYPE: PRT
<213> ORGANISM: Artificial Sequence
<220> FEATURE:
<223> OTHER INFORMATION: synthetic peptide (19F-FBA)-RSDLTPLFK(NH2)-NH2
<220> FEATURE:
<221> NAME/KEY: MOD_RES
<222> LOCATION: (1)..(1)
<223> OTHER INFORMATION: Xaa is fluorine-19 (radio)labeled fluorobenzoic
      acid (FBA) conjugated to Arg
<220> FEATURE:
<221> NAME/KEY: MOD_RES
<222> LOCATION: (9)..(9)
<223> OTHER INFORMATION: Xaa is Lys linked to a free N-terminal amine

<400> SEQUENCE: 45

Xaa Ser Asp Leu Thr Pro Leu Phe Xaa
1               5

<210> SEQ ID NO 46
<211> LENGTH: 8
<212> TYPE: PRT
<213> ORGANISM: Artificial Sequence
<220> FEATURE:
<223> OTHER INFORMATION: synthetic peptide 18F-FBA-RSDLTPLF
<220> FEATURE:
<221> NAME/KEY: MOD_RES
<222> LOCATION: (1)..(1)
<223> OTHER INFORMATION: Xaa is fluorine-18 (radio)labeled fluorobenzoic
      acid (FBA) conjugated to Arg

<400> SEQUENCE: 46

Xaa Ser Asp Leu Thr Pro Leu Phe
1               5

<210> SEQ ID NO 47
<211> LENGTH: 9
```

```
<212> TYPE: PRT
<213> ORGANISM: Artificial Sequence
<220> FEATURE:
<223> OTHER INFORMATION: synthetic peptide RSDLTPLFK(18F-FBA)-NH2
<220> FEATURE:
<221> NAME/KEY: MOD_RES
<222> LOCATION: (9)..(9)
<223> OTHER INFORMATION: Xaa is Lys conjugated fluorine-18
      (radio)labeled fluorobenzoic acid (FBA) linked to a free
      N-terminal amine

<400> SEQUENCE: 47

Arg Ser Asp Leu Thr Pro Leu Phe Xaa
1               5

<210> SEQ ID NO 48
<211> LENGTH: 9
<212> TYPE: PRT
<213> ORGANISM: Artificial Sequence
<220> FEATURE:
<223> OTHER INFORMATION: synthetic peptide (18F-FBA)-RSDLTPLFK(NH2)-NH2
<220> FEATURE:
<221> NAME/KEY: MOD_RES
<222> LOCATION: (1)..(1)
<223> OTHER INFORMATION: Xaa is fluorine-18 (radio)labeled fluorobenzoic
      acid (FBA) conjugated to Arg
<220> FEATURE:
<221> NAME/KEY: MOD_RES
<222> LOCATION: (9)..(9)
<223> OTHER INFORMATION: Xaa is Lys linked to a free N-terminal amine

<400> SEQUENCE: 48

Xaa Ser Asp Leu Thr Pro Leu Phe Xaa
1               5

<210> SEQ ID NO 49
<211> LENGTH: 8
<212> TYPE: PRT
<213> ORGANISM: Artificial Sequence
<220> FEATURE:
<223> OTHER INFORMATION: synthetic peptide 18F-FBA-PEG11-RSDLTPLF-NH2
<220> FEATURE:
<221> NAME/KEY: MOD_RES
<222> LOCATION: (1)..(1)
<223> OTHER INFORMATION: Xaa is fluorine-18 (radio)labeled fluorobenzoic
      acid (FBA) conjugated to polyethylene glycol (PEG)11 conjugated to
      Arg

<400> SEQUENCE: 49

Xaa Ser Asp Leu Thr Pro Leu Phe
1               5

<210> SEQ ID NO 50
<211> LENGTH: 8
<212> TYPE: PRT
<213> ORGANISM: Artificial Sequence
<220> FEATURE:
<223> OTHER INFORMATION: synthetic peptide 18F-FBA-RSDLTPLF-(PEG)11-NH2
<220> FEATURE:
<221> NAME/KEY: MOD_RES
<222> LOCATION: (1)..(1)
<223> OTHER INFORMATION: Xaa is fluorine-18 (radio)labeled fluorobenzoic
      acid (FBA) conjugated to Arg
<220> FEATURE:
<221> NAME/KEY: MOD_RES
<222> LOCATION: (8)..(8)
<223> OTHER INFORMATION: Xaa is Phe conjugated to polyethylene glycol
      (PEG)11

<400> SEQUENCE: 50

Xaa Ser Asp Leu Thr Pro Leu Xaa
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: synthetic peptide 18F-FBA-PEG11-RSDLTPLF-PEG11-
      NH2
<220> FEATURE:
<221> NAME/KEY: MOD_RES
<222> LOCATION: (1)..(1)
<223> OTHER INFORMATION: Xaa is fluorine-18 (radio)labeled fluorobenzoic
      acid (FBA) conjugated to polyethylene glycol (PEG)11 conjugated to
      Arg
<220> FEATURE:
<221> NAME/KEY: MOD_RES
<222> LOCATION: (8)..(8)
<223> OTHER INFORMATION: Xaa is Phe conjugated to polyethylene glycol
      (PEG)11

<400> SEQUENCE: 51

Xaa Ser Asp Leu Thr Pro Leu Xaa
1               5

<210> SEQ ID NO 52
<211> LENGTH: 10
<212> TYPE: PRT
<213> ORGANISM: Artificial Sequence
<220> FEATURE:
<223> OTHER INFORMATION: synthetic peptide c(RSDLTPLFE)K(18F-FBA)-NH2
<220> FEATURE:
<221> NAME/KEY: MISC_FEATURE
<222> LOCATION: (1)..(9)
<223> OTHER INFORMATION: residues undergo cyclization
<220> FEATURE:
<221> NAME/KEY: MOD_RES
<222> LOCATION: (10)..(10)
<223> OTHER INFORMATION: Xaa is Lys linked to fluorine-18 (radio)labeled
      fluorobenzoic acid (FBA)

<400> SEQUENCE: 52

Arg Ser Asp Leu Thr Pro Leu Phe Glu Xaa
1               5                   10

<210> SEQ ID NO 53
<211> LENGTH: 10
<212> TYPE: PRT
<213> ORGANISM: Artificial Sequence
<220> FEATURE:
<223> OTHER INFORMATION: synthetic peptide c(RSDLTPLFE)K
<220> FEATURE:
<221> NAME/KEY: MISC_FEATURE
<222> LOCATION: (1)..(9)
<223> OTHER INFORMATION: residues under cyclization

<400> SEQUENCE: 53

Arg Ser Asp Leu Thr Pro Leu Phe Glu Lys
1               5                   10
```